United States Patent
Furukawa et al.

(10) Patent No.: US 9,283,164 B2
(45) Date of Patent: Mar. 15, 2016

(54) COSMETIC AND TOPICAL SKIN PREPARATION COMPRISING HIGHER ALCOHOL-MODIFIED SILICONE

(75) Inventors: Haruhiko Furukawa, Chiba (JP); Akito Hayashi, Ichihara (JP); Tomohiro Iimura, Sodegaura (JP)

(73) Assignee: DOW CORNING TORAY CO., LTD., Chiyoda-Ku, Tokyo (JP)

( * ) Notice: Subject to any disclaimer, the term of this patent is extended or adjusted under 35 U.S.C. 154(b) by 293 days.

(21) Appl. No.: 13/643,416

(22) PCT Filed: Apr. 27, 2011

(86) PCT No.: PCT/JP2011/060790
§ 371 (c)(1),
(2), (4) Date: Jan. 3, 2013

(87) PCT Pub. No.: WO2011/136389
PCT Pub. Date: Nov. 3, 2011

(65) Prior Publication Data
US 2013/0116340 A1 May 9, 2013

(30) Foreign Application Priority Data
Apr. 28, 2010 (JP) ................. 2010-104555

(51) Int. Cl.
*A61K 8/58* (2006.01)
*A61Q 5/12* (2006.01)
(Continued)

(52) U.S. Cl.
CPC .............. *A61K 8/585* (2013.01); *A61K 8/891* (2013.01); *A61K 8/892* (2013.01); *A61K 8/897* (2013.01); *A61Q 19/00* (2013.01)

(58) Field of Classification Search
CPC ........ A61K 8/585; A61K 8/891; A61K 8/892; A61K 8/897; A61Q 19/00

USPC .................. 514/772; 556/449; 424/70.12
See application file for complete search history.

(56) References Cited

U.S. PATENT DOCUMENTS

| 4,910,013 A | 3/1990 | Kanamaru et al. |
| 4,980,167 A | 12/1990 | Harashima et al. |

(Continued)

FOREIGN PATENT DOCUMENTS

| EP | 0351297 A1 | 1/1990 |
| EP | 0475130 A2 | 3/1992 |

(Continued)

OTHER PUBLICATIONS

Viscosity: retrieved from inernet: http://physics.info/viscosity/. Retrieved on Mar. 24, 2015.*

(Continued)

*Primary Examiner* — Ernst V Arnold
*Assistant Examiner* — Hong Yu
(74) *Attorney, Agent, or Firm* — Howard & Howard Attorneys PLLC

(57) ABSTRACT

A cosmetic and a topical skin preparation comprising a higher alcohol-modified silicone (A) with the following general formula (1) wherein $R^1$ is, e.g., an alkyl group; P is a monovalent organic group that contains the Si—O bond or is a long-chain monovalent hydrocarbyl group; at least one Q is a higher alcohol modifying group (—(C10-C30)—OH); and (m1+m2+m3) is a number in the range from 0 to 55 and most favorably (m1+m2+m3) is 1.

(1)

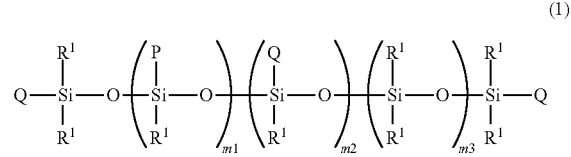

9 Claims, 1 Drawing Sheet

(51) Int. Cl.
*A61K 8/891* (2006.01)
*A61K 8/892* (2006.01)
*A61K 8/897* (2006.01)
*A61Q 19/00* (2006.01)

(56) References Cited

U.S. PATENT DOCUMENTS

| | | | |
|---|---|---|---|
| 5,063,051 | A | 11/1991 | Grollier et al. |
| 5,104,643 | A | 4/1992 | Grollier et al. |
| 5,470,551 | A * | 11/1995 | Dubief et al. ............ 424/70.12 |
| 5,530,084 | A | 6/1996 | Ihara et al. |
| 5,628,989 | A | 5/1997 | Harashima et al. |
| 5,654,362 | A | 8/1997 | Schulz, Jr. et al. |
| 5,939,478 | A | 8/1999 | Beck et al. |
| 5,981,680 | A | 11/1999 | Petroff et al. |
| 6,238,656 | B1 | 5/2001 | Morita et al. |
| 6,280,748 | B1 | 8/2001 | Morita et al. |
| 6,353,076 | B1 | 3/2002 | Barr et al. |
| 6,551,352 | B2 * | 4/2003 | Clerc et al. .................. 623/1.2 |
| 7,473,756 | B2 | 1/2009 | Hofacker |
| 7,482,419 | B2 | 1/2009 | Caprasse et al. |
| 7,612,051 | B2 | 11/2009 | Kamei et al. |
| 2001/0046507 | A1 | 11/2001 | Dietz et al. |
| 2009/0163648 | A1 | 6/2009 | Muenzmay et al. |

FOREIGN PATENT DOCUMENTS

| | | | |
|---|---|---|---|
| EP | 2072553 | A2 | 6/2009 |
| JP | 57192310 | A | 11/1982 |
| JP | 62216635 | A | 9/1987 |
| JP | 1106811 | A | 4/1989 |
| JP | 2167212 | A | 6/1990 |
| JP | 2243612 | A | 9/1990 |
| JP | 4164015 | A | 6/1992 |
| JP | 6136128 | A | 5/1994 |
| JP | 07-062102 | * | 3/1995 ........... C08G 77/392 |
| JP | 07-157489 | A | 6/1995 |
| JP | 08-012524 | A | 1/1996 |
| JP | 08-012546 | A | 1/1996 |
| JP | 8012545 | A | 1/1996 |
| JP | 09-241511 | A | 9/1997 |
| JP | 10-036219 | A | 2/1998 |
| JP | 11193331 | A | 7/1999 |
| JP | 2000038450 | A | 2/2000 |
| JP | 2000063225 | A | 2/2000 |
| JP | 2000281523 | A | 10/2000 |
| JP | 2000-309509 | A | 11/2000 |
| JP | 2001512164 | A | 8/2001 |
| JP | 2002-038013 | A | 2/2002 |
| JP | 2007532754 | A | 11/2007 |
| WO | WO 03/101412 | A2 | 12/2003 |
| WO | WO 2009/071662 | A2 | 6/2009 |

OTHER PUBLICATIONS

Silicones: retrieved from inernet: http://www.essentialchemicalindustry.org/polymers/silicones.html. Retrieved on Mar. 24, 2015.*

Mudge: Fatty alcohols—a review of therir natural synthesis and environmental distribution, Nov., 2005, retrieved frominternet: http://www.aciscience.org/docs/fatty_alcohols_mudge_2005.pdf. Retrieved on Mar. 24, 2015.*

Triton CG-110 surfactant: retrieved from internet: http://msdssearch.dow.com/PublishedLiteratureDOWCOM/dh_0893/0901b80380893847.pdf?filepath=surfactants/pdfs/noreg/119-01873.pdf&fromPage=GetDoc. Retrieved on Mar. 24, 2015.*

English language abstract for JP 1106811 extracted from the espacenet.com database on Jan. 15, 2013, 14 pages.

English language abstract for JP 2167212 extracted from the espacenet.com database on Jan. 15, 2013, 18 pages.

English language abstract for JP 2243612 extracted from the espacenet.com database on Jan. 15, 2013, 8 pages.

English language abstract for JP 4164015 extracted from the espacenet.com database on Jan. 15, 2013, 8 pages.

English language abstract and machine-assisted English translation for JP 07-157489 extracted from the PAJ database on Jan. 15, 2013, 23 pages.

English language abstract and machine-assisted English translation for JP 08-012524 extracted from the PAJ database on Jan. 15, 2013, 28 pages.

English language abstract for JP 8012545 extracted from the espacenet.com database on Jan. 15, 2013, 7 pages.

English language abstract and machine-assisted English translation for JP 08-012546 extracted from the PAJ database on Jan. 15, 2013, 26 pages.

English language abstract and machine-assisted English translation for JP 09-241511 extracted from the PAJ database on Jan. 15, 2013, 29 pages.

English language abstract and machine-assisted English translation for JP 10-036219 extracted from the PAJ database on Jan. 15, 2013, 37 pages.

English language abstract for JP 11193331 extracted from the espacenet.com database on Jan. 18, 2013, 15 pages.

English language abstract for JP 57192310 extracted from the espacenet.com database on Jan. 15, 2013, 8 pages.

English language abstract for JP 6136128 extracted from the espacenet.com database on Jan. 15, 2013, 48 pages.

English language abstract for JP 62216635 extracted from the espacenet.com database on Jan. 15, 2013, 10 pages.

English language abstract for JP 2000038450 extracted from the espacenet.com database on Jan. 18, 2013, 10 pages.

English language abstract for JP 2000063225 extracted from the espacenet.com database on Jan. 18, 2013, 15 pages.

English language abstract for JP 2000281523 extracted from the espacenet.com database on Jan. 18, 2013, 21 pages.

English language abstract and machine-assisted English translation for JP 2000-309509 extracted from the PAJ database on Jan. 15, 2013, 47 pages.

English language abstract not available for JP 2001512164; however, see English language equivalent U.S. Pat. No. 6,353,076. Orginal Document extracted from the espacenet.com database on Jan. 18, 2013, 65 pages.

English language abstract for JP 2002-038013 extracted from the espacenet.com database on Jan. 15, 2013, 19 pages.

English language abstract not available for JP 2007532754; however, see English language equivalent U.S. Pat. No. 7,482,419. Orginal document extracted from the espacenet.com database on Jan. 18, 2013, 39 pages.

English language abstract for EP 0351297 extracted from espacenet.com database on Apr. 8, 2013, 13 pages.

English language abstract for EP 2072553 extracted from espacenet.com database on Apr. 8, 2013, 17 pages.

International Search Report for Application PCT/JP2011/060790 dated Jan. 30, 2013, 5 pages.

* cited by examiner

COSMETIC AND TOPICAL SKIN PREPARATION COMPRISING HIGHER ALCOHOL-MODIFIED SILICONE

RELATED APPLICATIONS

This application is the National Stage of International Patent Application No. PCT/JP2011/060790, filed on Apr. 27, 2011, which claims priority to and all the advantages of Japanese Patent Application No. JP2010-104555, filed on Apr. 28, 2010, the content of which is incorporated herein by reference.

TECHNICAL FIELD

The present invention relates to a higher alcohol-modified silicone that has a special structure and to a cosmetic and a topical skin preparation that contain this higher alcohol-modified silicone and more particularly to a cosmetic and a topical skin preparation that have a suede-like material feel, as obtained when a silicone elastomer powder is dispersed in an oil, and that exhibit an excellent higher alcohol blendability. The present invention further relates to a cosmetic and a topical skin preparation that have a gel structure that incorporates a higher alcohol-modified silicone and to an oil-in-water emulsion-type cosmetic and an oil-in-water emulsion-type topical skin preparation that employ this higher alcohol-modified silicone as an emulsifying agent or as a co-emulsifying agent.

BACKGROUND ART

Organopolysiloxane derivatives can mitigate the stickiness and oily feel exhibited by a cosmetic and for this reason are proactively incorporated as an oil for cosmetic applications. Polydimethylsiloxanes, on the other hand, have also frequently been beset by problems arising from their structural features, for example, a poor absorbability/compatibility with the skin and an inadequate sense of moistness. Many types of organic-modified silicones have been introduced in order to solve these problems. Alcohol-modified silicones and carbinol-modified silicones are typical of the organic-modified silicones that have been introduced, and their use in hair cosmetics, hair dyes, and so forth has been proposed (for example, Patent Documents 1, 2, 3, and 4). However, these alcohol-modified silicones in all instances have a structure in which the hydroxyl group is bonded across, for example, a short-chain alkylene group that has fewer than 6 carbon atoms, and this has led to problems such as an unsatisfactory compatibility with the oily ingredients, such as higher alcohols, that are typically incorporated in cosmetics, crystallization of the higher alcohols and so forth in the blended state, and an impaired tactile feel.

Patent Document 5, on the other hand, discloses a cosmetic that incorporates a powder composition comprising a powder and a silicone compound that has an alcoholic hydroxyl group. In one example of the alcoholic hydroxyl group, a silicone compound is proposed that has a structure in which one hydroxyl group is bonded to silicon across an alkylene group that has 11 carbon atoms. However, this patent document does not specifically disclose a short-chain polysiloxane that has one alcoholic hydroxyl group at the terminus of the aforementioned alkylene group and that has a degree of polymerization of not more than 55 for the chain length of the siloxane chain, and in particular does not specifically disclose a silicone compound that has a short-chain polysiloxane structure such as a disiloxane or trisiloxane. In addition, these structures are neither described nor suggested. Thus, the novel higher alcohol-modified silicone according to the present invention is not specifically disclosed in Patent Document 5.

The incorporation of the powder composition in cosmetics is also disclosed in Patent Document 5, but Patent Document 5 does not describe the incorporation in cosmetics of an alcoholic hydroxyl group-containing silicone compound that has the specific structure described above and does not teach that a suede-like material feel is imparted to cosmetics by the incorporation of such a silicone compound. Similarly, Patent Document 5 in no way teaches or suggests that an alcoholic hydroxyl group-containing silicone with the specific structure described above improves the blendability of higher alcohols or that a uniform blend system may be obtained through the corresponding inhibition of higher alcohol crystallization.

An alcohol-modified organopolysiloxane in which the hydroxyl group is bonded to silicon across a long-chain alkylene group is known as a reactant (Patent Documents 6 and 7). However, while these documents do describe the use in cosmetic applications of the esterification reaction products of alcohol-modified organopolysiloxanes, they neither describe nor suggest the incorporation of these alcohol-modified organopolysiloxanes in cosmetics. Moreover, while these documents disclose an alcohol-modified organopolysiloxane in which the hydroxyl group is bonded across an alkylene group having fewer than 6 carbon atoms and an alcohol-modified organopolysiloxane in which the hydroxyl group is bonded across a $C_{11}$ alkylene group, the selection from therebetween of an alcohol-modified organopolysiloxane in which the hydroxyl group is bonded across a $C_{11}$ alkylene group is in no way described or suggested. Furthermore, there is no teaching or suggestion of any kind that these alcohol-modified organopolysiloxanes can impart a suede-like use sensation to cosmetics or that they can improve the blendability of higher alcohols and thereby prevent their crystallization.

While a "higher alcohol-modified silicone" has frequently been proposed as an example of a silicone oil for use in cosmetic applications, the "higher alcohol-modified silicone" in these documents in no way serves to identify or specifically describe the silicone, and these documents do not specifically describe a silicone having a carbinol group bonded across a $C_{10-30}$ divalent hydrocarbyl group as in the present invention (Patent Documents 8 and 9). While these documents do propose the use of a "higher alcohol-modified silicone" in cosmetic applications, an improvement in the use sensation or the compatibility with oily ingredients such as higher alcohols is in no way described or suggested, nor is the selection of a short-chain polysiloxane for the main chain of the carbinol group-containing silicone in any way described or suggested.

Accordingly, while the incorporation of a higher alcohol-modified silicone in cosmetics is already known, it is clear that—with regard to a higher alcohol-modified silicone that has the specific structure as in the present invention in which the carbinol group therein is bonded across a $C_{10-30}$ divalent hydrocarbyl group—the advantages and blending characteristics of such a higher alcohol-modified silicone with respect to cosmetics are entirely unexplored and are unknown.

Otherwise, it is known in the cosmetics sector that a gel structure is formed by a higher alcohol/water/surfactant system (for example, Nonpatent Document 1). However, conventional gel structures cannot stable incorporate silicones, which have an excellent tactile feel, due to compatibility problems, and improvements in this regard have been desired. In addition, when a silicone or nonpolar oil component is incorporated in a gel structure, the higher alcohol forming the gel structure may end up crystallizing with elapsed time, which can have a negative effect on the tactile feel, and improvement here has also been desired.

PATENT DOCUMENTS

[Patent Document 1] JP 57-192310 A
[Patent Document 2] JP 01-106811 A
[Patent Document 3] JP 04-164015 A
[Patent Document 4] JP 2000-309509 A
[Patent Document 5] JP 2002-038013 A
[Patent Document 6] JP 06-136128 A
[Patent Document 7] JP 07-157489 A
[Patent Document 8] JP 62-216635 A
[Patent Document 9] JP 02-167212 A

NONPATENT DOCUMENTS

[Nonpatent Document 1] Shoji FUKUSHIMA, *The Physical Chemistry of Cetyl Alcohol*, Chapter 6, pages 76-88 (Fragrance Journal Ltd.).

SUMMARY OF INVENTION

Technical Problems to be Solved

The present invention was pursued in order to solve the problems identified above. An object of the present invention is to provide a cosmetic and a topical skin preparation that incorporate an organic-modified silicone that, unlike the heretofore known organic-modified silicones, imparts a suede-like material feel to the cosmetic and topical skin preparation and exhibits an excellent blend stability with respect to various cosmetics. A further object of the present invention is to provide a cosmetic and a topical skin preparation that, when a higher alcohol is incorporated therein together with this organic-modified silicone, exhibit an improved blend stability and as a consequence can exhibit an excellent use sensation due to an inhibition of crystallization of the higher alcohol with elapsed time. A further object of the present invention is to provide a cosmetic and a topical skin preparation that—based on the replacement of a portion of the higher alcohol fraction in a gel structure that is formed by a higher alcohol/water/surfactant system, i.e., through the co-use of the higher alcohol and the aforementioned organic-modified silicone—can form a more stable gel structure than for the heretofore known organic-modified silicones. An additional object of the present invention is to provide a cosmetic and a topical skin preparation, and particularly an oil-in-water emulsion-type cosmetic/topical skin preparation, in which various oils and particularly silicones can be stably emulsified and which have an excellent tactile feel.

Solution to Problems

As a result of intensive investigations in order to solve the problems identified above, the present inventors discovered that these problems could be solved by a cosmetic and a topical skin preparation that contain a higher alcohol-modified silicone (A) that is represented by the following general formula (1), that has a relatively short polysiloxane main chain and specifically has a polysiloxane main chain wherein the number of disiloxane units constituting the main chain is in the range from 0 to 55, and that has at least one higher alcohol modifying group bonded to the silicon across a $C_{10-30}$ divalent hydrocarbyl group. The present invention was achieved based on this discovery. Modified silicones that lacked the specified higher alcohol modifying group and modified silicones that had this higher alcohol modifying group but in which the number of disiloxane units constituting the main chain exceeded the limit indicated above, not only were unable to manifest a suede-like material feel, but were also unable to adequately realize an excellent affinity for higher alcohols. In particular, this suede-like material feel is a tactile feel that has not heretofore been obtained with silicone-type oils and is extremely useful for cosmetics and topical skin preparations.

general formula (1):

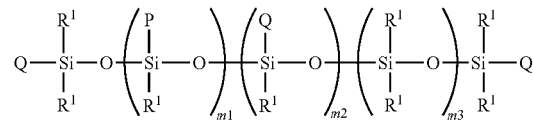

(1)

Each $R^1$ in the preceding formula is independently a $C_{1-10}$ alkyl group, $C_{6-10}$ aryl group, or the —OH group and each P is independently a monovalent organic group that contains at least one Si—O bond or is a $C_{11-30}$ long-chain monovalent hydrocarbyl group wherein all or a portion of the carbon-bonded hydrogen atoms therein may be substituted by a halogen atom.

Each Q in the preceding formula is independently a group selected from $R^1$, P, and higher alcohol modifying groups with the following general formula (2) and at least one of all the Q groups is the general formula (2) higher alcohol modifying group bonded to the silicon atom across a $C_{10-30}$ divalent hydrocarbyl group. In particular, when m2=0, at least one of the Q groups is this higher alcohol modifying group.

general formula (2):

wherein R is a $C_{10-30}$ divalent hydrocarbyl group that may contain a heteroatom m1, m2, and m3 are each numbers in the range from 0 to 55 and the relationship (m1+m2+m3) is a number in the range from 0 to 55.

The present inventors also discovered that the previously described problems can be very favorably solved by having the higher alcohol-modified silicone (A) be a higher alcohol-modified silicone having the trisiloxane structure shown by the general formula provided below. The present invention was also achieved based on this discovery.

general formula (1-1-1):

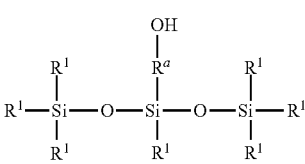

(1-1-1)

wherein $R^1$ is the same group as defined above and $R^a$ is a $C_{10-30}$ alkylene group or an arylene group.

The present inventors also discovered that by incorporating the previously described novel higher alcohol-functional silicone in a water-in-oil emulsion-type cosmetic, an oil-based cosmetic, or a topical skin preparation, a suede-like tactile feel, which is a material feel corresponding to that obtained when a silicone elastomer powder is dispersed in an oil and which has not been obtained up to now, can be imparted to various cosmetics and topical skin preparations. The present invention was also achieved based on this discovery.

The present inventors further discovered that the previously described novel higher alcohol-modified silicone, because it has a long-chain alkylene group, can be simply and easily blended in various cosmetics and topical skin preparations. In particular, it was discovered that, through the co-incorporation of the previously described higher alcohol-functional silicone together with a $C_{10-30}$ higher alcohol, higher alcohol crystallization can be inhibited and stable cosmetics and topical skin preparations can be obtained as a result. The present invention was also achieved based on this discovery.

Similarly, the present inventors discovered that the previously described higher alcohol-modified silicone is useful as a surfactant or co-surfactant for cosmetics and topical skin preparations and in particular discovered that the resulting gel structure exhibits an excellent stability and tactile feel when this higher alcohol-modified silicone is added to the gel structure formed by a higher alcohol/water/surfactant system. The present invention was also achieved based on this discovery.

Thus, the first subject matter of the present invention is a cosmetic and a topical skin preparation comprising a higher alcohol-modified silicone that is represented by general formula (1), supra, and that has at least one higher alcohol modifying group bonded to the silicone across a $C_{10-30}$ divalent hydrocarbyl group. This higher alcohol-modified silicone most preferably is a higher alcohol-modified silicone having the trisiloxane structure given by general formula (1-1-1) above.

The second subject matter of the present invention is a cosmetic and a topical skin preparation characteristically comprising 10 to 1000 mass parts of at least one $C_{10-30}$ higher alcohol per 100 mass parts of the previously described higher alcohol-modified silicone and a method of producing this cosmetic and topical skin preparation.

The third subject matter of the present invention is a cosmetic and a topical skin preparation in which a system comprising the higher alcohol-modified silicone/at least one $C_{10-30}$ higher alcohol/water/at least one surfactant forms a gel structure.

The fourth subject matter of the present invention is a cosmetic and a topical skin preparation, and particularly an oil-in-water emulsion-type cosmetic and topical skin preparation, that use the higher alcohol-modified silicone.

The fifth subject matter of the present invention is the previously described cosmetic and topical skin preparation that further contain a silicone resin.

The sixth subject matter of the present invention is the previously described cosmetic and topical skin preparation that further contain a silicone elastomer.

The seventh subject matter of the present invention relates to a favorable method of producing the previously described cosmetic and topical skin preparation and specifically is a method of producing the cosmetic and the topical skin preparation that characteristically comprises:

a step of heating a system that incorporates 100 mass parts of at least one higher alcohol-modified silicone (A) with general formula (1) and 10 to 1000 mass parts of at least one $C_{10-30}$ higher alcohol (B), at from 50° C. to 150° C.

Advantageous Effects of Invention

The present invention can provide a cosmetic and a topical skin preparation that contain a novel higher alcohol-modified silicone that, unlike the heretofore known organic-modified silicones, can impart a suede-like material feel to the cosmetic and topical skin preparation and that exhibits an excellent stability when blended in various cosmetics and topical skin preparations. When blended together with a higher alcohol, the higher alcohol-modified silicone according to the present invention improves the higher alcohol's blend stability and inhibits crystallization of the higher alcohol with elapsed time and can thereby provide a cosmetic and a topical skin preparation that can realize an excellent use sensation; a method of producing such a cosmetic and topical skin preparation is also provided. Through the co-incorporation of the higher alcohol-modified silicone according to the present invention with a higher alcohol, a cosmetic and a topical skin preparation can be provided in which, in comparison to the heretofore known organic-modified silicones, the gel structure formed by a higher alcohol/water/surfactant system exhibits greater stability. In addition, the use of the higher alcohol-modified silicone according to the present invention makes possible the stable emulsification of various oils and in particular of silicones and thereby makes possible the introduction of a cosmetic and a topical skin preparation—and particularly an oil-in-water emulsion-type cosmetic and topical skin preparation—that have an excellent tactile feel.

BEST MODE FOR CARRYING OUT THE INVENTION

Figure 1:
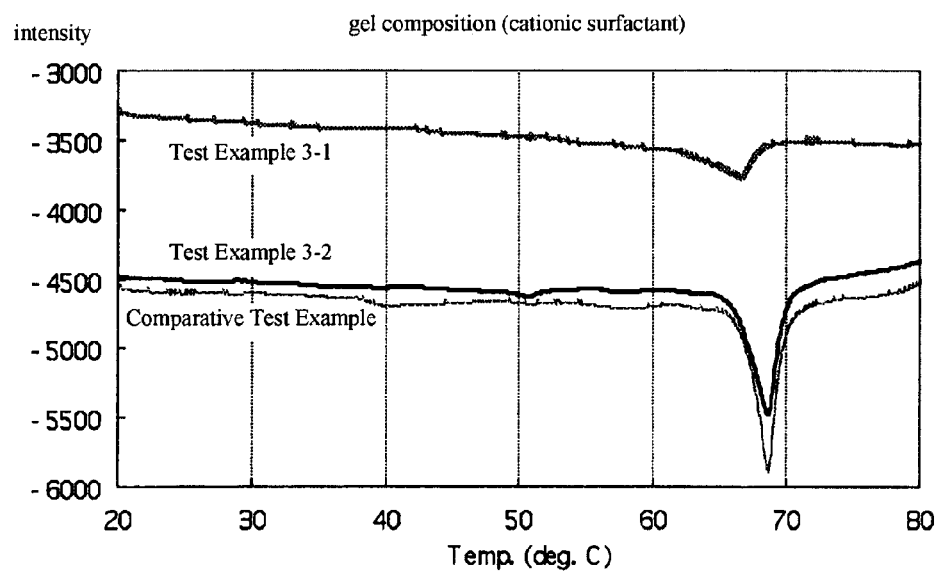
FIG. 1 gives the results of differential scanning calorimetric (DSC) measurements on Test Examples 3-1 and 3-2 and their comparative test example: "Gel composition comprising a cationic surfactant (stearyltrimethylammonium chloride)/cetanol/water"

The cosmetic and the topical skin preparation according to the present invention characteristically contain a higher alcohol-modified silicone that is represented by general formula (1) below, that is a polysiloxane in which the main chain thereof has a relatively low degree of polymerization, and that has, in side chain or terminal position on the polysiloxane, a higher alcohol modifying group bonded across a $C_{10-30}$ divalent hydrocarbyl group to silicon.

general formula (1):

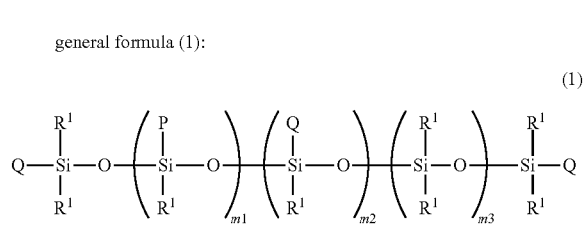

(1)

The silicon-bonded higher alcohol modifying group, which is a characteristic feature of the higher alcohol-modified silicone according to the present invention, will be described first.

The higher alcohol modifying group is constituted of a divalent hydrocarbyl group in which a terminal of Q is bonded to a silicon atom in the polysiloxane main chain and in which one hydroxyl group, that is, a higher alcoholic hydroxyl group, is bonded at the other terminal, i.e., Si—R—OH wherein R is a $C_{10-30}$ divalent hydrocarbyl group that may contain a heteroatom.

The divalent hydrocarbyl group constituting the higher alcohol modifying group is a divalent hydrocarbyl group that may contain a heteroatom and may be straight chain or branched, but which must have only one higher alcoholic hydroxyl group (—OH) at a terminal other than the terminal bonded to the silicon and which does not encompass divalent functional groups that have a plurality of hydrophilic groups (hydroxyl groups), such as glycerol-modified groups and saccharide-modified groups. In addition, it does not encompass divalent functional groups that have two or more polyether bonds such as polyoxyalkylene groups.

This $C_{10-30}$ divalent hydrocarbyl group is favorably exemplified by branched and straight-chain $C_{10-30}$ alkylene groups and by arylene groups. In addition, the higher alcohol modifying group bonded to silicon across the $C_{10-30}$ divalent hydrocarbyl group is particularly favorably the functional group represented by —$C_nH_{2n}$—OH. n in this formula is a number in the range from 10 to 30, preferably is a number in the range from 10 to 20, and particularly preferably is a number in the range from 10-15. The higher alcohol modifying group can be specifically exemplified by the hydroxydecyl group, hydroxyundecyl group, hydroxydodecyl group, and hydroxytridecyl group.

The higher alcohol modifying group bonded to the silicon across a $C_{10-30}$ divalent hydrocarbyl group may have a structure in which two or more divalent hydrocarbyl groups are linked by a heteroatom-containing linking group —X—, for example, —R—X—R—OH. The linking group X can be specifically exemplified by a heteroatom-containing linking group selected from the ether bond (—O—), ester bonds (—COO—, —OCO—), and amide bonds (—CONH—, NHCO). This structure, however, does not encompass divalent functional groups that have two or more polyether bonds, such as polyoxyalkylene groups.

The silicon-bonded higher alcohol modifying group under consideration has a chemical structure analogous to the higher alcohols that are generally used in cosmetics, e.g., stearyl alcohol, behenyl alcohol, and so forth, and exhibits very similar properties from the standpoint of hydrophilicity/lipophilicity, and as a consequence exhibits an excellent affinity for higher alcohols in particular and can impart the properties to the higher alcohol-modified silicone as a whole of an emulsifying agent or co-emulsifying agent with a low hydrophilic/lipophilic balance. When the divalent hydrocarbyl group constituting the higher alcohol modifying group contains a plurality of hydrophilic functional groups, for example, 2 or more hydroxyl groups, or when the number of carbon atoms is less than the previously indicated lower limit, this results in a decline in the affinity with higher alcohols having 8 or more carbon atoms and particularly with $C_{10-30}$ higher alcohols and can thereby worsen the blend stability and can have a negative effect on the ability to prevent the crystallization of higher alcohols, infra, and on the gelation performance. In addition, when the number of carbons in the divalent hydrocarbyl group constituting the higher alcohol modifying group exceeds the previously indicated upper limit, this modifying group takes on an excessively large hydrophobicity (lipophilicity) and the affinity with higher alcohol may then be inadequate.

The bonding position for the higher alcohol modifying group under consideration may be side chain position or terminal position on the polysiloxane main chain, and the higher alcohol-modified silicone may have a structure in which two or more higher alcohol modifying groups are bonded in each molecule. The structure may be one in which the two or more higher alcohol modifying groups are bonded only in side chain position on the polysiloxane main chain, only in terminal position, or in both side chain position and terminal position. Viewed from the perspective of providing the higher alcohol-modified silicone according to the present invention with the properties that derive from the higher alcohol modifying group, the modification rate with the previously described higher alcohol modifying group, see below, is preferably in the range from 1 to 50 mol % of the total functional groups bonded to the polysiloxane main chain and particularly preferably is in the range from 2.5 to 45 mol % of the total functional groups bonded to the polysiloxane main chain. The modification rate by the higher alcohol modifying group, expressed in mol %, is given by the following formula.

modification rate (mol %)=(number of higher alcohol modifying groups bonded to silicon per molecule)/{6+2×(m1+m2+m3)}×100

Taking as an example a higher alcohol-modified silicone that is a trisiloxane having one higher alcohol modifying group, one of the eight silicon-bonded functional groups is modified by a higher alcohol group, and the modification rate by the higher alcohol modifying group is therefore 12.5%.

The structure of the higher alcohol-modified silicone according to the present invention is specifically described herebelow.

The higher alcohol-modified silicone according to the present invention is given by the previously indicated general formula (1), wherein each $R^1$ independently is a $C_{1-10}$ alkyl group or an aryl group; each P is independently a monovalent organic group that contains at least one Si—O bond or is a $C_{11-30}$ long-chain monovalent hydrocarbyl group wherein all or a portion of the carbon-bonded hydrogen atoms therein may be substituted by halogen; each Q is independently a group selected from $R^1$, P, and higher alcohol modifying groups with the following general formula (2) in which bonding to the silicon atom occurs across a $C_{10-30}$ divalent hydrocarbyl group; when m2=0, at least one Q is the general formula (2) higher alcohol modifying group bonded to the silicon atom across a $C_{10-30}$ divalent hydrocarbyl group; and m1, m2, and m3 are each numbers in the range from 0 to 55 and satisfy a relationship wherein (m1+m2+m3) is a number in the range from 0 to 55.

general formula (2):

wherein R is a $C_{10-30}$ divalent hydrocarbyl group that may contain a heteroatom The $C_{1-10}$ alkyl group, aryl group, and hydroxyl group (—OH) encompassed by $R^1$ can be specifically exemplified by alkyl groups such as methyl, ethyl, propyl, butyl, pentyl, hexyl, heptyl, octyl, decyl, and so forth; cycloalkyl groups such as cyclopentyl, cyclohexyl, and so forth; aryl groups such as phenyl, tolyl, and so forth; and the hydroxyl group (—OH). At least a portion of the carbon-bonded hydrogen atoms in these groups may be replaced by a halogen atom, e.g., fluorine, or by an organic group that contains, for example, the epoxy group, an acyl group, the carboxyl group, an amino group, a methacryl group, or the mercapto group.

Each P is independently a monovalent organic group that contains at least one Si—O bond or is a $C_{11-30}$ long-chain monovalent hydrocarbyl group wherein all or a portion of the carbon-bonded hydrogen atoms therein may be substituted by halogen, and can be exemplified by a group selected from $C_{11-30}$ alkyl, $C_{11-30}$ aralkyl, polysiloxane chains having a structure in which branching occurs from the polysiloxane main chain, and highly branched polysiloxane functional groups having a carbosiloxane dendrimer structure (also called a "siloxane dendrimer"). These functional groups are highly hydrophobic and through their introduction into side chain or terminal position on the higher alcohol-modified silicone according to the present invention they can improve the affinity of oleophilic compounds with the higher alcohol-modified silicone according to the present invention; they are also useful because they make possible adjustment of the polarity of the molecule as a whole and make possible the design of a molecular structure that can function as a surfactant or co-surfactant.

The $C_{11-30}$ long-chain alkyl group can be specifically exemplified by undecyl, dodecyl, tridecyl, and so forth; all or a portion of the carbon-bonded hydrogen atoms in these alkyl groups may be substituted by a halogen atom, e.g., the fluorine atom and so forth; and, considering the properties, such as the hydrophobicity, of such halogenated alkyl groups, a long-chain alkyl group having a non-straight chain structure, e.g., branched or cyclic, may also be selected. The preceding also applies to the $C_{11-30}$ long-chain aralkyl groups. The long-chain alkyl group or long-chain aralkyl group encompassed by the functional group P can be introduced into the polysiloxane chain by addition reacting the corresponding unsaturated hydrocarbon having a carbon-carbon double bond at the molecular chain terminal, e.g., an alkene and so forth, with a silicon-bonded hydrogen atom.

The monovalent organic group that contains at least one Si—O bond can be exemplified by a group selected from polysiloxane chains that have a structure that branches from the polysiloxane main chain and highly branched silylalkyl groups that have a carbosiloxane dendrimer structure (also called a "siloxane dendrimer"). Examples at a more specific level are the functional groups given by the following general formulas (2-1) to (2-4).

general formula (2-1):

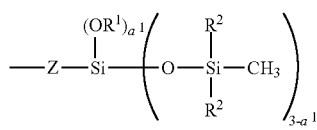
(2-1)

general formula (2-2):

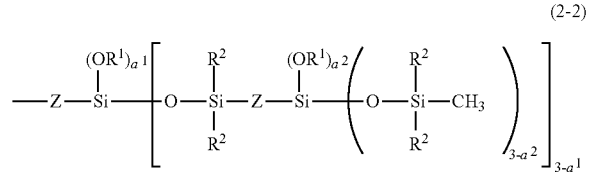
(2-2)

In formulas (2-1) and (2-2), $R^1$ is the same group as defined above, $R^2$ is a $C_{1-6}$ alkyl group or is the phenyl group, and $a^1$ and $a^2$ are each independently numbers in the range from 0 to 3. Each Z is independently a divalent organic group and can be specifically exemplified by divalent organic groups formed by an addition reaction between a silicon-bonded hydrogen atom and a functional group that has an unsaturated hydrocarbyl group at its terminal, e.g., an alkenyl group or a carboxylate ester group such as the acryloxy group and methacryloxy group; however, there is no limitation to these functional groups and a suitable selection can be made in correspondence to the procedure for introducing the silylalkyl group. In particular, a preferred example of a silylalkyl group having a carbosiloxane dendrimer structure is represented by formula (2-1) wherein $a^1$ is 0 and Z is preferably a $C_{2-10}$ alkylene group introduced by the reaction of an alkenyl group with a silicon-bonded hydrogen atom or is preferably a divalent organic group introduced by a reaction between a silicon-bonded hydrogen atom and an unsaturated carboxylate ester group.

general formula (2-3):

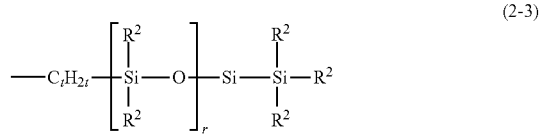
(2-3)

general formula (2-4):

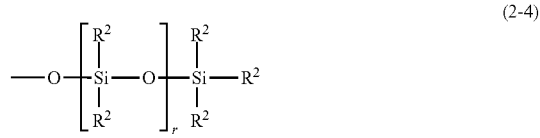
(2-4)

$R^2$ in general formulas (2-3) and (2-4) is the same group as defined above and r is a number in the range from 1 to 30. t in formula (2-3) is a number in the range from 2 to 10. Viewed from the perspective of the tactile feel of the higher alcohol-modified silicone according to the present invention and its blendability with higher alcohols, r is preferably a number in the range from 1 to 20 and particularly preferably is a number in the range from 1 to 10.

Each Q is a group independently selected from $R^1$, P, and higher alcohol modifying groups bonded to the silicon across the previously described $C_{10-30}$ divalent hydrocarbyl group, wherein when m2=0, at least one Q is a higher alcohol modifying groups bonded to the silicon across a $C_{10-30}$ divalent hydrocarbyl group. That is, the higher alcohol-modified silicone according to the present invention may have a structure in which the previously described higher alcohol modifying group, which is an essential functional group, is bonded only in terminal position on the polysiloxane main chain.

The higher alcohol modifying group bonded to silicon across a $C_{10-30}$ divalent hydrocarbyl group and represented by general formula (2) is as described above. In addition, the modification rate by this higher alcohol modifying group is preferably in the range from 1 to 50 mol % of the total functional groups bonded to the polysiloxane main chain and, considering the technical effects of the present invention, is particularly preferably in the range from 3 to 45 mol % of the total functional groups bonded to the polysiloxane main chain.

A characteristic feature of the higher alcohol-modified silicone according to the present invention is that the polysiloxane chain constituting the main chain has a relatively low degree of polymerization. Specifically, m1, m2, and m3 in general formula (1) are each numbers in the range from 0 to 55 and satisfy a relationship wherein (m1+m2+m3) is a number in the range from 0 to 55.

Viewed from the perspective of the suede-like tactile feel and affinity with higher alcohol that are manifested when the higher alcohol-modified silicone is incorporated in a cosmetic or topical skin preparation, preferably m1, m2, and m3 are each numbers in the range from 0 to 30 and (m1+m2+m3) is a number in the range from 0 to 30 and particularly preferably m1, m2, and m3 are each numbers in the range from 0 to 25 and (m1+m2+m3) is a number in the range from 0 to 25.

(m1+m2+m3) is most favorably 0 or 1 for the higher alcohol-modified silicone according to the present invention, in which case the higher alcohol-modified silicone according to the present invention takes the form of a higher alcohol-modified silicone that has a disiloxane or trisiloxane structure for its main chain.

On the other hand, when (m1+m2+m3) in the higher alcohol-modified silicone with general formula (1) exceeds the previously indicated upper limit and particularly when a long-chain polysiloxane structure is present in which the degree of polymerization exceeds 60, the use sensation generated in the cosmetic and topical skin preparation by the polysiloxane moiety and the effects deriving from its chemical structure become so substantial that the characteristic effects of the present invention are not satisfactorily realized in the cosmetic and topical skin preparation. In specific terms, a smooth use sensation deriving from the polysiloxane moiety is strongly elaborated upon incorporation in a cosmetic or topical skin preparation, and as a consequence the characteristic use sensation of a suede-like body that is realized by the introduction of the higher alcohol modifying group becomes inadequate. Furthermore, since the main chain polysiloxane moiety will then assume a large proportion of the molecule as a whole, it may not be possible to satisfactorily achieve the technical effects of affinity with higher alcohols and an inhibition of higher alcohol crystallization for the blend. In the case of a higher alcohol/water/surfactant system, the affinity with higher alcohols will also be reduced and the surface-active effect also becomes inadequate and the formation of a stable gel structure may then not be possible.

As indicated above, the technical effects of the present invention are realized by the combination of the introduction of the higher alcohol modifying group with the use of a special chain length for the polysiloxane chain constituting the main chain, and given this goal the higher alcohol-modified silicone incorporated in the cosmetic and topical skin preparation is desirably at least one higher alcohol-modified silicone given by the following general formulas (1-1), (1-2), and (1-3).

general formula (1-1):

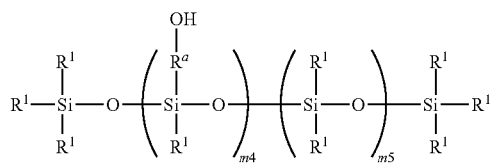

(1-1)

The higher alcohol-modified silicone with the preceding general formula (1-1) has the higher alcohol modifying group in side chain position, and $R^1$ in this formula is the same group as defined above and favorably is all methyl or phenyl. In addition, $R^a$ is a branched or straight-chain $C_{10\text{-}30}$ alkylene group or an arylene group and preferably is a $C_{10\text{-}20}$ alkylene group such as, for example, undecylene. m4 is a number in the range from 1 to 30; m5 is a number in the range from 0 to 29; and (m4+m5) is a number in the range from 1 to 30. (m4+m5) is preferably a number in the range from 1 to 25 and m4 is preferably from 1 to 15 and m5 is preferably from 0 to 24. m4=1 and m5=0 is most preferred in the present invention and provides the trisiloxane-type structure shown by general formula (1-1-1) below.

general formula (1-2):

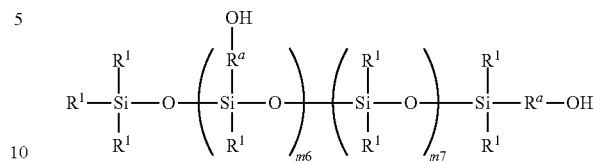

(1-2)

The higher alcohol-modified silicone given by the preceding general formula (1-2) has the higher alcohol modifying group at one terminal or at one terminal and in side chain position. $R^1$ in the formula is the same group as defined above and favorably is all methyl or phenyl. $R^a$ is a branched or straight-chain $C_{10\text{-}30}$ alkylene group or an arylene group and preferably is a $C_{10\text{-}20}$ alkylene group such as, for example, undecylene. m6 is a number in the range from 0 to 30; m7 is a number in the range from 0 to 30; and (m6+m7) is a number in the range from 0 to 30. (m6+m7) is particularly preferably a number in the range from 0 to 25.

general formula (1-3):

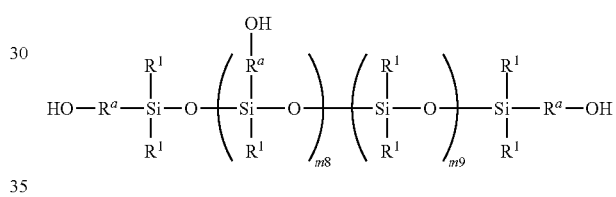

(1-3)

The higher alcohol-modified silicone given by the preceding general formula (1-3) has the higher alcohol modifying group at both terminals or at both terminals and in side chain position. $R^1$ in the formula is the same group as defined above and favorably is all methyl or phenyl. $R^a$ is a branched or straight-chain $C_{10\text{-}30}$ alkylene group or an arylene group and preferably is a $C_{10\text{-}20}$ alkylene group such as, for example, undecylene. m8 is a number in the range from 0 to 30; m9 is a number in the range from 0 to 30; and (m8+m9) is a number in the range from 0 to 30. (m8+m9) is particularly preferably a number in the range from 0 to 25.

The higher alcohol-modified silicone given by the following general (1-1-1) and having a trisiloxane structure is most preferred for the higher alcohol-modified silicone according to the present invention.

general formula (1-1-1):

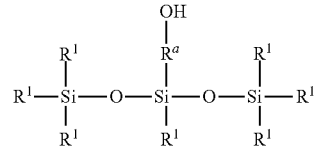

(1-1-1)

The higher alcohol-modified silicone given by the preceding general formula (1-1-1) is a trisiloxane that has the higher alcohol modifying group in side chain position. $R^1$ in the formula is the same group as defined above and favorably is all methyl or phenyl. $R^a$ is a branched or straight-chain $C_{10\text{-}30}$ alkylene group or an arylene group and preferably is a $C_{10-20}$ alkylene group such as, for example, undecylene.

The higher alcohol-modified silicones given by general formulas (1-1), (1-2), (1-3), and (1-1-1) are particularly preferred for use in the present invention from the standpoint of particularly good technical effects—i.e., a distinctive suede-like use sensation and an affinity with higher alcohols and an inhibition of their crystallization—when incorporated in a cosmetic or topical skin preparation and from the standpoint of the formation of a very stable gel structure by higher alcohol/water/surfactant systems. This gel structure is a gel structure in which a network structure or mesh structure comprising a higher alcohol/higher alcohol-modified silicone/surfactant is swollen by water and is thermally stable and, when incorporated in a cosmetic or topical skin preparation, exhibits a distinctive or characteristic use sensation. In addition, through the dissolution of a water-soluble component with the water, this water-soluble component can be stably supported in the gel structure.

The higher alcohol-modified silicones given by general formulas (1-1), (1-2), (1-3), and (1-1-1)—because they have a favorably short polysiloxane chain wherein the number of diorganosiloxane units constituting the main chain is not more than 30 and preferably not more than 25—exhibit the effects of the previously described higher alcohol modifying group and, in addition to this, through their function as an emulsifying agent/co-emulsifying agent/dispersion stabilizer for oleophilic compounds such as oils and so forth, offer the advantage given their ability to form stable emulsions of being stably blendable in various formulations and cosmetic products and in quasidrug formulations and particularly topical skin preparations. Furthermore, since they undergo orientation at the surface of various powders and can thereby impart a suitable water repellency, they can be used to treat the surface of powders for application to cosmetics and topical skin preparations; they exhibit a good compatibility with various powders and can improve the blend stability and uniform dispersibility of various powders in cosmetics. In the case of use for surface treatment, the surface treatment is preferably carried out using the higher alcohol-modified silicone at from 0.1 to 10 mass parts per 100 mass parts of the powder. In addition, the powder surface treatment is preferably also performed in combination with another, known surface treatment. This surface treatment can be exemplified by treatment with a methylhydrogenpolysiloxane, silicone resin, metal soap, silane coupling agent, inorganic oxide such as silica or titanium oxide, or a fluorine compound such as a perfluoroalkylsilane or perfluoroalkyl phosphate ester salt.

In addition, the higher alcohol-modified silicone according to the present invention, just like many organic-modified silicones, forms a uniform film on the surface of the skin and hair, improves its tactile feel, and imparts a protective effect against, for example, drying. When, in particular, the higher alcohol-modified silicone according to the present invention is incorporated in a hair cosmetic, it provides a hair maintenance and repair effect and offers the advantages of preventing spit ends and hair breakage and of being able to maintain healthy and lustrous hair.

Similarly, the higher alcohol-modified silicone according to the present invention is useful as an ingredient for topical skin preparations, and its incorporation in a topical skin preparation as a replacement for all or a portion of a known higher alcohol such as stearyl alcohol or an oil such as a hydrocarbon oil such as petrolatum, provides a spreadability with a distinctive suede-like use sensation and provides an excellent sense of moistness on the skin, but without causing strong skin irritation or stickiness when coated on an affected part. Moreover, even when coated on an affected part that includes a delicate mucous membrane, the advantages accrue of a natural use sensation and the absence post-application of itching or an uncomfortable sensation.

The higher alcohol-modified silicone according to the present invention can be obtained by the addition reaction of an unsaturated higher alcohol compound having a carbon-carbon double bond at one terminal of the molecular chain to a polyorganopolysiloxane that has a reactive functional group and specifically an organopolysiloxane that has the silicon-hydrogen bond. Similarly, the higher alcohol-modified silicone according to the present invention can also be produced by a method in which the previously indicated organopolysiloxane that has the silicon-hydrogen bond is addition reacted with a compound that has a carbon-carbon double bond at one molecular chain terminal and an alkyl ester group or alkyl aldehyde group to synthesize a polyorganopolysiloxane having an alkyl ester group or alkyl aldehyde group, followed by conversion to a higher alcohol modifying group using hydrogen or any of various reducing agents. The type of addition reaction is not particularly limited, but the addition reaction is preferably run in the presence of a hydrosilylation reaction catalyst from the standpoints of the yield, purity, and reaction control.

For example, the higher alcohol-modified silicone according to the present application can be obtained by addition reacting, in the presence of a hydrosilylation reaction catalyst, an organohydrogenpolysiloxane with the following general formula (1') with an unsaturated higher alcohol compound with the following general formula (2') in an amount of substance that provides at least 1 molar equivalent per silicon-bonded hydrogen in the organohydrogenpolysiloxane.

general formula (1'):

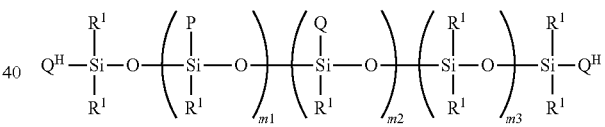

(1')

In the preceding formula, $R^1$ and P are the same groups as defined above and each $Q^H$ is independently $R^1$, P, or a silicon-bonded hydrogen atom Si—H wherein, when m2=0, at least one $Q^H$ is a silicon-bonded hydrogen atom. m1, m2, and m3 are the same numbers as defined above. This organohydrogenpolysiloxane is suitably an organohydrogenpolysiloxane that has silicon-bonded hydrogen in side chain and/or terminal position and that has from 0 to 30 disiloxane units and is particularly preferably 1,1,1,3,5,5,5-heptamethyltrisiloxane.

general formula (2'):

R'—OH

With the objective of, for example, improving the tactile feel of a cosmetic formulation and/or improving the compatibilities therein, a co-modification may also be performed by introducing the previously indicated functional group P into the silicon-hydrogen bond-containing organopolysiloxane by an addition reaction carried out before, during, or after the reaction described above, and this co-modification is preferred. Thus, production can be more favorably carried out specifically by setting up a state in which at least an unsaturated higher alcohol compound having a carbon-carbon double bond at a molecular chain terminal, is present with a functional group P precursor compound that has one reactive unsaturated group in each molecule and reacting them together with the organohydrogensiloxane that has silicon-bonded hydrogen in side chain and/or terminal position.

The hydrosilylation reaction is preferably run in the presence of a catalyst, for example, a compound of platinum, ruthenium, rhodium, palladium, osmium, iridium, and so forth, wherein platinum compounds are particularly effective due to their high catalytic activities. This platinum compound can be exemplified by chloroplatinic acid; platinum metal; platinum metal supported on a support such as alumina, silica, carbon black, and so forth; and platinum complexes such as a platinum-vinylsiloxane complex, a platinum-phosphine complex, a platinum-phosphite complex, a platinum-alcoholate complex, and so forth. When a platinum catalyst is used, the quantity of catalyst use is about 0.5 to 1000 ppm as platinum metal.

The higher alcohol-modified silicone according to the present invention may also be subjected to a hydrogenation treatment with the objective of ameliorating the post-reaction odor caused by residual unsaturated compound. The procedure for carrying out this hydrogenative deodorization treatment can be exemplified by methods that use pressurization with hydrogen gas and methods that employ a hydrogenating agent such as a metal hydride, and the hydrogenation reaction may be a homogeneous reaction or a heterogeneous reaction. These may be run as such by themselves or combinations of the preceding may be performed. However, when one considers the benefit of a lack of residual used catalyst in the product, a heterogeneously catalyzed hydrogenation reaction using a solid catalyst is most preferred.

Usable for the solid hydrogenation catalyst here are the usual noble metal catalysts, such as platinum-based catalysts and palladium-based catalysts, as well as nickel-based catalyst. Examples at a more specific level are nickel, palladium, platinum, rhodium, and cobalt by themselves and also catalysts that combine a plurality of metals, e.g., platinum-palladium, nickel-copper-chromium, nickel-copper-zinc, nickel-tungsten, and nickel-molybdenum. The optionally used catalyst support can be exemplified by active carbon, silica, silica-alumina, alumina, zeolite, and so forth. The copper-containing containing hydrogenation catalysts can be exemplified by Cu—Cr, Cu—Zn, Cu—Si, Cu—Fe—Al, and Cu—Zn—Ti. The configuration of the hydrogenation catalyst cannot be categorically specified because it will vary with the reactor type, but as a general matter it can be suitably selected from configurations such as powders, granules, tablets, and so forth. In addition, the platinum catalyst used for the synthesis step, i.e., the hydrosilylation reaction, can also be directly used as such. A single one of the previously described hydrogenation catalysts can be used or two or more can be used in combination.

A hydrogenation reaction may also be used to purify the crude higher alcohol-modified silicone product yielded by the previously described addition reaction. Specifically, purification can be performed by carrying out a hydrogenative deodorization treatment in the presence of a hydrogenation catalyst in the presence or absence of solvent, and the use of such a purified product is preferred in the case of application in cosmetics where reduced odor and compatibility with other cosmetic components are required. In addition, the crude co-modified organopolysiloxane product or the hydrogenate is preferably subjected to a stripping step, in which light substances are distilled out under reduced pressure while in contact with nitrogen gas; this stripping step may be run before or after the previously described deodorization treatment.

Similarly, the crude higher alcohol-modified silicone product yielded by the previously described addition reaction may also be conveniently deodorized by first adding an acid and hydrolyzing the unreacted unsaturated compound and then carrying out a stripping step in which the light substances are distilled out under reduced pressure while in contact with nitrogen gas.

The solvents, reaction conditions, vacuum conditions, and so forth, used for the purification of known organopolysiloxane copolymers and polyether-modified silicones can be used and selected without particular limitation for the hydrogenation reaction and stripping step under discussion.

The incorporation of at least one higher alcohol-modified silicone according to the present invention in a cosmetic or topical skin preparation can impart thereto a distinctive suede-like use sensation, as when a silicone elastomer powder is dispersed in an oil. This distinctive use sensation is more clearly recognized by the user as the quantity of incorporation of the higher alcohol-modified silicone according to the present invention increases. In particular, incorporation in a skin cosmetic, as typified by make-up cosmetics, or in a hair cosmetic that has a rinse action/hair treatment action can impart a distinctive material feel on the skin or to the hair that is clearly different from that for known modified silicones. The amount of incorporation here can be selected as appropriate in conformity with the type of cosmetic or topical skin preparation, and as a general matter the higher alcohol-modified silicone according to the present invention is used within the range from 0.05 to 50 mass % of the cosmetic or topical skin preparation as a whole and is preferably used in the range from 0.1 to 25 mass % from the standpoint of the perception of the distinctive suede-like use sensation described above.

With the goal of adjusting, for example, the viscosity, tactile feel, dispersion characteristics, and so forth, two or more higher alcohol-modified silicones according to the present invention can be used that have different modification rates by the higher alcohol modifying group, that have different polysiloxane chain lengths, or that have different bonding positions for the higher alcohol modifying group, i.e., side chain position/terminal position; these can also be used in different ratios. In order to improve the affinity with higher alcohol, infra, the higher alcohol-modified silicone according to the present invention may be incorporated as a composition prepared in advance by mixing at least one higher alcohol to uniformity with the higher alcohol-modified silicone and in particular may be incorporated into a cosmetic as a mixture of the higher alcohol-modified silicone according to the present invention with the unsaturated higher alcohol reactant or with the saturated higher alcohol that is the hydrogenate of the latter. The mixing ratio in such cases and the quantity of use for each component are selected as appropriate in conformity to the form desired for the cosmetic or topical skin preparation, and adjustments with respect to the use quantities of blend components such as powders, surfactants, and so forth, can also be readily made within the compositional design ranges for ordinary cosmetics and topical skin preparations.

The higher alcohol-modified silicone according to the present invention can be particularly favorably used in the present invention in that its particularly good technical effects with regard to its affinity with higher alcohols and its ability to inhibit their crystallization results in the formation of a very stable gel structure by the higher alcohol/water/surfactant system. These technical effects are believed to be due to the following: the higher alcohol modifying group that is introduced into the relatively short polysiloxane chain has a structure analogous to that of a higher alcohol, and due to this its compatibility and the intermolecular affinity are improved; in addition, the higher alcohol-modified silicone according to the present invention itself functions as a surfactant or co-surfactant.

The higher alcohol is particularly favorably (B) a $C_{10-30}$ higher alcohol that corresponds to the modifying group in the higher alcohol-modified silicone according to the present invention (this silicone is also referred to below as component (A)), as this provides a particularly good affinity with the higher alcohol-modified silicone according to the present invention.

The $C_{10-30}$ higher alcohol (B) is a monovalent saturated or unsaturated aliphatic alcohol, and its hydrocarbyl group moiety may be a straight chain or may be branched, but straight chain is more preferred. A higher alcohol having a melting point of at least 40° C. is also more preferred. The formation of a gel structure may not be possible when a higher alcohol having a melting point below 40° C. is used in combination with the higher alcohol-modified silicone according to the present invention. The $C_{10-30}$ higher alcohol used by the present invention can be exemplified by lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, sitosterol, phytosterol, lanosterol, lanolin alcohol, hydrogenated lanolin alcohol, and so forth. The use is more preferred in the present invention of a single higher alcohol having a melting point of 40 to 80° C. or a combination of a plurality of higher alcohols that provides a melting point of 40 to 70° C.

There is no particular limitation on the quantity of incorporation of the $C_{10-30}$ higher alcohol (B) in the cosmetic of the present invention, but, viewed from the perspective of the blend stability and the inhibition of crystallization for component (B) in the cosmetic, the incorporation of at least one $C_{10-30}$ higher alcohol (B) at from 5 to 1000 mass parts per 100 mass parts of the higher alcohol-modified silicone (A) is preferred and the incorporation of 10 to 500 mass parts is particularly preferred. When the quantity of component (B) incorporation is less than the lower limit, the function as an oil or surfactant may not be adequately realized when the higher alcohol is incorporated in the cosmetic. When, on the other, the quantity of component (B) incorporation exceeds the upper limit given above, the technical effect in particular of higher alcohol crystallization inhibition may be inadequate.

This higher alcohol crystallization is a phenomenon in which the higher alcohol, e.g., lauryl alcohol, incorporated in the cosmetic or topical skin preparation converts into a water-insoluble crystal during formulation or during storage and precipitates or solidifies, and is particularly prone to occur in formulations that contain the ionic surfactants generally used in cosmetics. This crystallized higher alcohol has a negative effect on the use sensation and blend stability of the cosmetic; due to its water insolubility, it is strongly resistant to wash off post-use and remains on the surface of the hair or skin, and, in the case of continual use, it can cause a deterioration in the tactile feel and can cause damage to cuticle-containing hair.

The higher alcohol-modified silicone (A) according to the present invention has a modifying group with a structure analogous to that of these higher alcohol molecules and has a relatively short polysiloxane main chain, which results in an improved affinity with higher alcohols and can effectively inhibit, during formulation of the cosmetic and during cosmetic storage, the crystallization of these higher alcohols and the precipitation of the solidified higher alcohol. This serves to improve the use sensation and blend stability of formulations that incorporate a higher alcohol. Moreover, even when a partial crystallization does occur, the higher alcohol-modified silicone according to the present invention, because it has excellent detergent characteristics for higher alcohols, prevents the higher alcohol from forming an aggregate with an ionic surfactant and becoming an insoluble solid and thus offers the advantages of facilitating wash out with water post-use and supporting the maintenance of an excellent use sensation.

In particular, the higher alcohol-modified silicone (A) according to the present invention, when used in a cosmetic or topical skin preparation that has a system comprising higher alcohol/water/surfactant, offers the advantage of making possible, at a very low quantity of use, the stable gelation of all or a portion of the cosmetic or topical skin preparation, and is particularly useful when the preparation of a stable cosmetic gel is desired. More specifically, when the cosmetic or topical skin preparation contains a $C_{10-30}$ higher alcohol (B), water (C), and a surfactant (D), a cosmetic or topical skin preparation can then be readily obtained that exhibits the characteristic feature that the system comprising the higher alcohol-modified silicone (A)/at least one $C_{10-30}$ higher alcohol (B)/water (C)/at least one surfactant (D) forms a gel structure.

More particularly, this gel structure is a gel structure in which a network structure comprising the higher alcohol-modified silicone (A)/at least one $C_{10-30}$ higher alcohol (B)/at least one surfactant (D) is swollen by the water (C), and is thermally stable and exhibits a distinctive use sensation. In addition, through the dissolution of a water-soluble component in the water it becomes possible to stably support water-soluble components in the gel structure. The network structure that is the skeleton of the gel would ordinarily form from the higher alcohol (B) and surfactant (D), but it is thought that the higher alcohol-modified silicone (A) of the present invention, because it exhibits an excellent compatibility with the higher alcohol (B) and has a substructure that is analogous to a higher alcohol, is able to contribute to the formation of a stable gel skeleton and to make possible the formation of a stable gel structure at a very small quantity of use.

From the standpoint of forming a stable gel structure, the quantity of higher alcohol-modified silicone (A) incorporation is in the range from 0.1 to 25 mass % of the cosmetic or topical skin preparation as a whole and preferably is in the range from 0.5 to 10 mass %. More specifically, letting the sum of the components (A) to (D) that form the gel structure be 100 mass %, the quantity of incorporation of each component in the cosmetic or topical skin preparation is preferably in the following ranges, i.e., a favorable cosmetic or topical skin preparation has a gel structure comprising the higher alcohol-modified silicone (A) at 0.5 to 10 mass %, the at least one $C_{10-30}$ higher alcohol (B) at 1 to 40 mass %, the water (C) at 60 to 98 mass %, and the surfactant (D) at 0.5 to 10 mass %. When the higher alcohol-modified silicone (A) according to the present invention in particular has the trisiloxane structure given by general formula (1-1-1), it can form a very stable gel structure comprising the higher alcohol-modified silicone (A)/at least one $C_{10-30}$ higher alcohol (B)/water (C)/at least one surfactant (D) at a quantity use for component (A) of about 0.5 to 5 mass %. The advantages accrue as a consequence, particularly in the case of incorporation in a water-based cosmetic, of engineering a desirable configuration or formulation and not impairing the distinctive suede-like tactile feel. The formation of this gel structure can be easily confirmed by visual inspection, but can also be confirmed by differential scanning calorimetry (DSC), while optical microscopy and small-angle x-ray scattering can be used to confirm the formation of a liquid crystal structure.

The water (C) should be clean and free of components toxic to humans and can be exemplified by tap water, purified water, and mineral water. The quantity of incorporation of the water (C) in the gel structure described above, letting the sum of the individual constituent components be 100 mass %, is preferably 70 to 98 mass %, and for a cosmetic gel or topical skin preparation gel this may also be an aqueous system in which optional water-soluble components have been incorporated. A cosmetic gel or topical skin preparation gel that incorporates the higher alcohol-modified silicone (A) of the present invention is useful as a stable water-containing cosmetic and as a stable water-containing topical skin preparation.

At least one or two or more surfactants selected from the group consisting of anionic surfactants, cationic surfactants, nonionic surfactants, and amphoteric surfactants can be selected for the at least one surfactant (D), and the use of an ionic surfactant that is an anionic surfactant or a cationic surfactant is particularly suitable with respect to gel structure formation. In addition, a silicone-type nonionic surfactant is suitably used because this can improve the stability of the formulation as a whole. The quantity of incorporation for these surfactants (D), in the case of formation of a thermally stable gel state, is in the range from 0.1 to 25 mass % of the cosmetic as a whole and is preferably in the range from 0.5 to 10 mass % of the cosmetic as a whole, and all or a portion of these surfactants may form the previously described gel structure. However, when the cosmetic or topical skin preparation according to the present invention is to be used for skin cleansing or hair cleansing service, then with the objective of improving the cleansing characteristics the surfactant (D) can be incorporated in the range from 0.1 to 90 mass % of the cosmetic or topical skin preparation as a whole, while the incorporation of at least 25 mass % surfactant component is also preferred from the perspective of the cleansing properties.

The anionic surfactant can be specifically exemplified by the following: saturated and unsaturated fatty acid salts, e.g., sodium laurate, sodium stearate, sodium oleate, sodium linolenate, and so forth; alkyl sulfate salts; alkylbenzenesulfonic acids, e.g., hexylbenzenesulfonic acid, octylbenzenesulfonic acid, dodecylbenzenesulfonic acid, and so forth, and their salts; polyoxyalkylene alkyl ether sulfate salts; polyoxyalkylene alkenyl ether sulfate salts; polyoxyethylene alkyl sulfate ester salts; the salts of alkyl sulfosuccinate esters; polyoxyalkylene sulfosuccinate alkyl ester salts; polyoxyalkylene alkylphenyl ether sulfate salts; octyltrimethylammonium hydroxide; dodecyltrimethylammonium hydroxide; alkylsulfonate; polyoxyethylene alkylphenyl ether sulfate salts; polyoxyalkylene alkyl ether acetate salts; alkyl phosphate salts; polyoxyalkylene alkyl ether phosphate salts; acylglutamic acid salts; α-acylsulfonic acid salts; alkylsulfonate salts; alkylallylsulfonate salts; α-olefinsulfonate salts; alkylnaphthalenesulfonate salts; alkanesulfonate salts; alkyl or alkenyl sulfate salts; alkylamide sulfate salts; alkyl or alkenyl phosphate salts; alkylamide phosphate salts; alkyloylalkyltaurine salts; N-acylamino acid salts; sulfosuccinate salts; alkyl ether carboxylate salts; amide ether carboxylate salts; α-sulfofatty acid ester salts; alanine derivatives; glycine derivatives; and arginine derivatives. The salts can be exemplified by alkali metal salts, e.g., sodium and so forth; alkaline-earth metal salts, e.g., magnesium and so forth; alkanolamine salts such as the triethanolamine salt and so forth; and ammonium salts.

The cationic surfactant can be exemplified by alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE)oleylmethylammonium chloride (2EO), benzalkonium chloride, alkylbenzalkonium chloride, alkyldimethylbenzalkonium chloride, benzethonium chloride, stearyldimethylbenzylammonium chloride, lanolin-derived quaternary ammonium salts, the diethylaminoethylamide of stearic acid, the dimethylaminopropylamide of stearic acid, behenamidepropyl dimethyl hydroxypropyl ammonium chloride, (stearoylcolaminoformylmethyl)pyridinium chloride, cetylpyridinium chloride, tall oil alkylbenzylhydroxyethylimidazolinium chloride, and benzylammonium salts.

The nonionic surfactant can be exemplified by polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene(hydrogenated) castor oils, polyoxyalkylene alkylphenols, polyoxyalkylene alkylphenyl ethers, polyoxyalkylene phenylphenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycols, diethylene glycol, polyoxyalkylene-modified silicones, polyglyceryl-modified silicones, glyceryl-modified silicones, saccharide-modified silicones, fluorosurfactants, polyoxyethylene-polyoxypropylene block polymers, and alkyl polyoxyethylene-polyoxypropylene block polymer ethers. The polyoxyalkylene-modified silicones, polyglyceryl-modified silicones, and glyceryl-modified silicones may also suitably have an alkyl branch, straight-chain silicone branch, siloxane dendrimer branch, and so forth, optionally provided therein along with the hydrophilic group.

Because it has a short-chain silicone moiety, the higher alcohol-modified silicone (A) according to the present invention can function—particularly when used in combination with a silicone-type nonionic surfactant—as a co-surfactant that improves the stability of the nonionic surfactant and can improve the stability of the formulation as a whole. Co-use with a polyoxyalkylene-modified silicone, polyglyceryl-modified silicone, or glyceryl-modified silicone is particularly favorable, wherein, in the case of incorporation in a cosmetic, the higher alcohol-modified silicone (A) is preferably mixed in advance with such a silicone-type nonionic surfactant.

The amphoteric surfactant can be exemplified by imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. Specific examples are imidazoline-type amphoteric surfactants such as sodium 2-undecyl-N,N,N-(hydroxyethylcarboxymethyl)-2-imidazoline and 2-cocoyl-2-imidazolinium hydroxide-1-carboxyethyloxy disodium salt; alkylbetaine-type amphoteric surfactants such as lauryldimethylaminoacetic acid betaine and myristyl betaine; amidobetaine-type amphoteric surfactants such as cocofatty acid amidopropyldimethylaminoacetic acid betaine, palm kernel oil fatty acid amidopropyldimethylaminoacetic acid betaine, beef tallow fatty acid amidopropyldimethylaminoacetic acid betaine, hydrogenated beef tallow fatty acid amidopropyldimethylaminoacetic acid betaine, lauric acid amidopropyldimethylaminoacetic acid betaine, myristic acid amidopropyldimethylaminoacetic acid betaine, palmitic acid amidopropyldimethylaminoacetic acid betaine, stearic acid amidopropyldimethylaminoacetic acid betaine, and oleic acid amidopropyldimethylaminoacetic acid betaine; alkylsulfobetaine-type amphoteric surfactants such as cocofatty acid dimethylsulfopropylbetaine; alkylhydroxysulfobetaine-type amphoteric surfactants such as lauryldimethylaminohydroxysulfobetaine; phosphobetaine-type amphoteric surfactants such as laurylhydroxyphosphobetaine; and amidoamino acid-type amphoteric surfactants such as sodium N-lauroyl-N'-hydroxyethyl-N'-carboxymethylethylenediamine, sodium N-oleoyl-N'-hydroxyethyl-N'-carboxymethylethylenediamine, sodium N-cocoyl-N'-hydroxyethyl-N'-carboxymethylethylenediamine, potassium N-lauroyl-N'-hydroxyethyl-N'-carboxymethylethylenediamine, potassium N-oleoyl-N'-hydroxyethyl-N'-carboxymethylethylenediamine, sodium N-lauroyl-N-hydroxyethyl-N'-carboxymethylethylenediamine, sodium N-oleoyl-N-hydroxyethyl-N'-carboxymethylethylenediamine, sodium N-cocoyl-N-hydroxyethyl-N'-carboxymethylethylenediamine, monosodium N-lauroyl-N-hydroxyethyl-N',N'-dicarboxymethylethylenediamine, monosodium N-oleoyl-N-hydroxyethyl-N',N'-dicarboxymethylethylenediamine, monosodium N-cocoyl-N-hydroxyethyl-N',N'-dicarboxymethylethylenediamine, disodium N-lauroyl-N-hydroxyethyl-N',N'-dicarboxymethylethylenediamine, disodium N-oleoyl-N-hydroxyethyl-N',N'-dicarboxymethylethylenediamine, and disodium N-cocoyl-N-hydroxyethyl-N',N'-dicarboxymethylethylenediamine.

The semi-polar surfactant can be exemplified by alkylamine oxide-type surfactants, for example, alkylamine oxides, alkylamidoamine oxides, and alkylhydroxyamine oxides, wherein $C_{10-18}$ alkyldimethylamine oxides and $C_{8-18}$ alkoxyethyldihydroxyethylamine oxides are preferably used. Specific examples are dodecyldimethylamine oxide, dimethyloctylamine oxide, diethyldecylamine oxide, bis(2-hydroxyethyl)dodecylamine oxide, dipropyltetradecylamine oxide, methylethylhexadecylamine oxide, dodecylamidopropyldimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, cocofatty acid alkyldimethylamine oxide, caprylic acid amidopropyldimethylamine oxide, capric acid amidopropyldimethylamine oxide, lauric acid amidopropyldimethylamine oxide, myristic acid amidopropyldimethylamine oxide, palmitic acid amidopropyldimethylamine oxide, stearic acid amidopropyldimethylamine oxide, isostearic acid amidopropyldimethylamine oxide, oleic acid amidopropyldimethylamine oxide, ricinoleic acid amidopropyldimethylamine oxide, 12-hydroxystearic acid amidopropyldimethylamine oxide, cocofatty acid amidopropyldimethylamine oxide, palm kernel oil fatty acid amidopropyldimethylamine oxide, castor oil fatty acid amidopropyldimethylamine oxide, lauric acid amidoethyldimethylamine oxide, myristic acid amidoethyldimethylamine oxide, cocofatty acid amidoethyldimethylamine oxide, lauric acid amidoethyldiethylamine oxide, myristic acid amidoethyldiethylamine oxide, cocofatty acid amidoethyldiethylamine oxide, lauric acid amidoethyldihydroxyethylamine oxide, myristic acid amidoethyldihydroxyethylamine oxide, and cocofatty acid amidoethyldihydroxyethylamine oxide.

The higher alcohol-modified silicone (A) according to the present invention, because it has a hydrophilic moiety and a hydrophobic moiety in the molecule, can function, like a higher alcohol, as a surfactant or as a co-surfactant that supports the emulsion stability provided by a surfactant. Due to this, when incorporated in a cosmetic it can function, like the surfactants described above, as a cleansing agent component and can also emulsify other oily ingredients. The emulsion state may be a water-in-oil emulsion-type cosmetic, an oil-in-water emulsion-type cosmetic, or their multilayer emulsions or microemulsions, wherein the use is particularly preferred of an oil-in-water emulsion-type cosmetic or an oil-in-water emulsion-type topical skin preparation in either case having a structure in which the continuous phase is an aqueous phase and the lipophilic component is dispersed in particulate form in the water.

The emulsion particles in the, for example, oil-in-water emulsion-type cosmetic, are emulsion particles provided by the emulsification by the previously described surfactant of the other oily ingredient components of the cosmetic, and the average particle size of the emulsion particles can be measured by a known measurement instrument using, for example, laser diffraction scattering. The oil-in-water emulsion-type cosmetic and oil-in-water emulsion-type topical skin preparation according to the present invention may be a transparent microemulsion having a measured average particle size of not more than 0.1 μm or may be a cloudy white, large-particle emulsion having an average particle size in excess of 10.0 μm. In addition, the emulsion particles can be microfine-sized with the goal of improving the stability of the emulsion and improving the transparency of the appearance. In particular, an emulsion with a particle size of 0.5 to 20 μm can be selected with the goal of improving the adherence to the hair or skin and improving the use sensation and is preferred.

The cosmetic of the present invention may also incorporate an oily ingredient other than the previously exemplified $C_{10-30}$ higher alcohols. Oils are a particularly suitable oily ingredient, and suitable examples thereof are at least one oil selected from silicone oils, hydrocarbon oils, and ester oils. This oil may be a solid oil such as a wax or may be a thick, high viscosity gum-like oil or paste-like oil as described below. In addition, the cosmetic of the present invention, for its additive components such as an oil and including the previously described surfactant, preferably uses a plant-derived ingredient for all or part of the structure thereof.

The quantity of oil incorporation is selected in conformity with the formulation, type, and site of application of the cosmetic and the properties that are to be emphasized, but can be in the range from 0.1 to 90 mass % of the cosmetic as a whole wherein the range of 0.5 to 70 mass % is particularly suitable. The incorporation of two or more oils that differ in viscosity and type is also favorable.

The silicone oil used as an oil component does not encompass the previously described higher alcohol-modified silicone (A) and silicone-type nonionic surfactants, is hydrophobic, and may have a cyclic, straight-chain, or branched molecular structure. The viscosity of the silicone oil at 25° C. is generally in the range from 0.65 to 100,000 mm$^2$/s and is preferably in the range from 0.65 to 10,000 mm$^2$/s.

This silicone oil can be specifically exemplified by cyclic organopolysiloxanes, straight-chain organopolysiloxanes, and branched organopolysiloxanes. Preferred thereamong are volatile straight-chain organopolysiloxanes, volatile branched organopolysiloxanes, and volatile cyclic organopolysiloxanes.

For example, an organopolysiloxane with the following general (3), (4), or (5) can be used for the silicone oil.

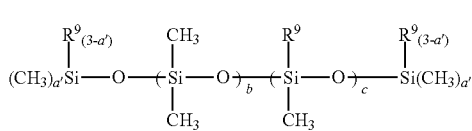 (3)

wherein:
$R^9$ is a group selected from the hydrogen atom, the hydroxyl group, monovalent $C_{1-30}$ unsubstituted or fluorine-substituted or amino-substituted alkyl groups, aryl groups, alkoxy groups, and groups represented by $(CH_3)_3SiO\{(CH_3)_2SiO\}_1Si(CH_3)_2CH_2CH_2-$ wherein 1 is an integer from 0 to 1000,
a' is an integer from 0 to 3,
b' is an integer from 0 to 1000, and
c' is an integer from 0 to 1000 with the proviso that $1 \le b' + c' \le 2000$

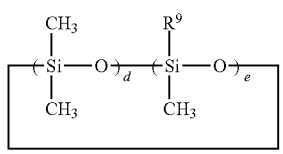 (4)

wherein:
$R^9$ is as defined above,
d is an integer from 0 to 8, and
e is an integer from 0 to 8 with the proviso that $3 \le d+e \le 8$ $R^9_{(4-f)}Si(OSiCH_3)_g$ (5)

wherein:
$R^9$ is as defined above,
f is an integer from 1 to 4, and
g is an integer from 0 to 500

The monovalent $C_{1-30}$ unsubstituted or fluorine-substituted or amino-substituted alkyl groups, aryl groups, and alkoxy groups can be exemplified by $C_{1-30}$ straight-chain or branched-chain alkyl groups such as methyl, ethyl, propyl, butyl, pentyl, hexyl, heptyl, octyl, decyl, dodecyl, and so forth; $C_{3-30}$ cycloalkyl groups such as cyclopentyl, cyclohexyl, and so forth; $C_{6-30}$ aryl groups such as phenyl, tolyl, xylyl, naphthyl, and so forth; $C_{1-30}$ alkoxy groups such as methoxy, ethoxy, propoxy, and so forth; and groups provided by replacing at least a portion of the carbon-bonded hydrogen in the preceding groups with fluorine or the amino group. Unsubstituted alkyl groups and aryl groups are preferred; unsubstituted $C_{1-6}$ alkyl groups and aryl groups are more preferred; and methyl, ethyl, and phenyl are particularly preferred.

More specifically, the silicone oils having the structures described above can be specifically exemplified by cyclic organopolysiloxanes such as hexamethylcyclotrisiloxane (D3), octamethylcyclotetrasiloxane (D4), decamethylcyclopentasiloxane (D5), dodecamethylcyclohexasiloxane (D6), 1,1-diethylhexamethylcyclotetrasiloxane, phenylheptamethylcyclotetrasiloxane, 1,1-diphenylhexamethylcyclotetrasiloxane, 1,3,5,7-tetravinyltetramethylcyclotetrasiloxane, 1,3,5,7-tetracyclohexyltetramethylcyclotetrasiloxane, tris(3,3,3-trifluoropropyl)trimethylcyclotrisiloxane, 1,3,5,7-tetra(3-methacryloxypropyl)tetramethylcyclotetrasiloxane, 1,3,5,7-tetra(3-acryloxypropyl)tetramethylcyclotetrasiloxane, 1,3,5,7-tetra(3-carboxypropyl)tetramethylcyclotetrasiloxane, 1,3,5,7-tetra(3-vinyloxypropyl)tetramethylcyclotetrasiloxane, 1,3,5,7-tetra(p-vinylphenyl)tetramethylcyclotetrasiloxane, 1,3,5,7-tetra[3-(p-vinylphenyl)propyl]tetramethylcyclotetrasiloxane, 1,3,5,7-tetra(N-acryloyl-N-methyl-3-aminopropyl)tetramethylcyclotetrasiloxane, and 1,3,5,7-tetra(N,N-bis(lauroyl)-3-aminopropyl)tetramethylcyclotetrasiloxane.

The straight-chain organopolysiloxanes can be exemplified by straight-chain organopolysiloxanes such as dimethylpolysiloxane endblocked at both molecular chain terminals by trimethylsiloxy, ranging from low viscosity dimethylsilicones at, for example, 2 mPa·s and 6 mPa·s, to high viscosity dimethylsilicones at, for example, 1,000,000 mPa·s, organohydrogenpolysiloxanes, methylphenylpolysiloxanes endblocked at both molecular chain terminals by trimethylsiloxy, dimethylsiloxane-methylphenylsiloxane copolymers endblocked at both molecular chain terminals by trimethylsiloxy, diphenylpolysiloxanes endblocked at both molecular chain terminals by trimethylsiloxy, dimethylsiloxane-diphenylsiloxane copolymers endblocked at both molecular chain terminals by trimethylsiloxy, trimethylpentaphenyltrisiloxane, phenyl(trimethylsiloxy)siloxane, methylalkylpolysiloxanes endblocked at both molecular chain terminals by trimethylsiloxy, dimethylpolysiloxane-methylalkylsiloxane copolymers endblocked at both molecular chain terminals by trimethylsiloxy, dimethylsiloxane-methyl(3,3,3-trifluoropropyl)siloxane copolymers endblocked at both molecular chain terminals by trimethylsiloxy, α,ω-dihydroxypolydimethylsiloxanes, α,ω-diethoxypolydimethylsiloxanes, 1,1,1,3,5,5,5-heptamethyl-3-octyltrisiloxane, 1,1,1,3,5,5,5-heptamethyl-3-dodecyltrisiloxane, 1,1,1,3,5,5,5-heptamethyl-3-hexadecyltrisiloxane, tristrimethylsiloxymethylsilane, tristrimethylsiloxyalkylsilane, tetrakistrimethylsiloxysilane, tetramethyl-1,3-dihydroxydisiloxane, octamethyl-1,7-dihydroxytetrasiloxane, hexamethyl-1,5-diethoxytrisiloxane, hexamethyldisiloxane, octamethyltrisiloxane, higher alkoxy-modified silicones, higher fatty acid-modified silicones, and dimethiconol.

The branched organopolysiloxanes can be exemplified by methyltristrimethylsiloxysilane, ethyltristrimethylsiloxysilane, propyltristrimethylsiloxysilane, tetrakistrimethylsiloxysilane, and phenyltristrimethylsiloxysilane.

When at least one of these silicone oils is incorporated in the cosmetic and topical skin preparation of the present invention, the incorporation of the higher alcohol-modified silicone (A) according to the present invention can then realize a suede-like tactile feel, in addition to the realization of the fresh tactile feel characteristic of silicone oils. For example, the use of the higher alcohol-modified silicone (A) in the range from 0.5 to 25 mass % of the cosmetic as a whole in combination with a low-viscosity organopolysiloxane makes it possible to impart a distinctive suede-like use sensation, as obtained when a silicone elastomer powder is dispersed in an oil, and to impart a fresh tactile feel when the cosmetic is spread on the skin. The quantity of use of the oil in this case is preferably in the range from 0.5 to 25 mass % of the cosmetic as a whole and is more preferably smaller than that of the higher alcohol-modified silicone from the standpoint of achieving a strong suede-like tactile feel.

The non-silicone oil is preferably a liquid at 5 to 100° C. A hydrocarbon oil and/or a fatty acid ester oil is preferred for the non-silicone oil. These oils in particular are the components widely used as bases for make-up cosmetics. The higher alcohol-modified silicone (A) according to the present invention, because it has a higher alcohol modifying group that contains a divalent hydrocarbyl group such as an alkylene group, also has an excellent compatibility with non-silicone oils, and this provides the advantage from a blend standpoint of making it possible to impart a suede-like tactile feel to the cosmetic or topical skin preparation while retaining the moisturizing characteristics of these hydrocarbon oils and/or fatty acid ester oils. Moreover, the higher alcohol-modified silicone (A) according to the present invention, because it functions as a surfactant or co-surfactant, has the advantage of being able to improve the blend stability and timewise stability for formulations of these oils.

With respect to formulations that do not use a non-silicone oil as the cosmetic base, such as a hair cosmetic or an oil-in-water emulsion-type cosmetic, the incorporation of a non-silicone oil at from 0.5 to 25 mass % of the cosmetic as a whole has the advantage of making it possible to impart the suede-like tactile feel that originates with the higher alcohol-modified silicone (A) according to the present invention and in addition to impart moisturizing characteristics, a moist feel, and a smooth use sensation to the cosmetic. With respect, on the other hand, to formulations that use an oil as a make-up cosmetic base, the incorporation of a non-silicone oil at from 0.1 to 95 mass % of the cosmetic as a whole has the advantage of making it possible to exploit the suede-like tactile feel that originates with the higher alcohol-modified silicone (A) according to the present invention while retaining the form and appearance of a stable cosmetic and improving the compatibility as a whole with other oily ingredients.

With regard to the relationship with components other than component (A), the use of a hydrocarbon oil and/or a fatty acid ester oil in combination with the previously described silicone oil can impart the fresh tactile feel characteristic of silicone oils; can hold the moisture fraction on the skin; can provide the cosmetic with a moisturizing sensation, also known as a moist tactile feel, as if the hair or skin were moistened; can provide the cosmetic with a smooth tactile feel; and also has the advantage of not impairing the timewise stability of the cosmetic and topical skin preparation. In addition, a cosmetic that incorporates both a silicone oil as described above and a hydrocarbon oil and/or a fatty acid ester oil has the advantages of improving the moisturizing effect of its moisturizing components on the skin by making possible a more stable and more uniform coating of these moisturizing components on the skin or hair and also of imparting a smoother and moister tactile feel than a cosmetic that contains only a non-silicone oil, i.e., a hydrocarbon oil or fatty acid ester oil.

The hydrocarbon oils can be exemplified by liquid paraffin, light liquid isoparaffin, heavy liquid isoparaffin, petrolatum, n-paraffins, isoparaffins, isododecane, isohexadecane, polyisobutylene, hydrogenated polyisobutylene, polybutene, ozokerite, ceresin, microcrystalline wax, paraffin wax, polyethylene wax, polyethylene-polypropylene wax, squalane, squalene, pristane, polyisoprene, and so forth.

The esters oils can be exemplified by hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-ethylhexanoate, trimethylolpropane tri-2-ethylhexanoate, ditrimethylolpropane triethylhexanoate, ditrimethylolpropane isostearate/sebacate, trimethylolpropane trioctanoate, trimethylolpropane tri isostearate, diisopropyl adipate, diisobutyl adipate, 2-hexyldecyl adipate, di-2-heptylundecyl adipate, diisostearyl malate, hydrogenated castor oil monoisostearate, n-alkylglycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentyl glycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, esters between dipentaerythritol and fatty acids, 2-hexyldecyl myristate, ethyl laurate, 2-octyldodecyl N-lauroyl-L-glutamate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, isopropyl N-lauroylsarcosinate, diisostearyl malate, neopentyl glycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethylpentanediol dineopentanoate acid, methylpentanediol dineopentanoate, octyldodecyl neodecanoate, 2-butyl-2-ethyl-1,3-propanediol dioctanoate, pentaerythrityl tetraoctanoate, pentaerythrityl hydrogenated rosin, pentaerythrityl triethylhexanoate, dipentaerythrityl(hydroxystearate/stearate/rosinate), polyglyceryl tetraisostearate, polyglyceryl-10 nonaisostearate, polyglyceryl-8 deca(erucate/isostearate/ricinoleate), diglyceryl(hexyldecanoate/sebacate)oligoester, glycol distearate (ethylene glycol distearate), diisopropyl dimer dilinoleate, diisostearyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensate, hydrogenated castor oil dimer dilinoleate, hydroxyalkyl dimer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri(caprylate/caprate), glyceryl tri(caprylate/caprate/myristate/stearate), hydrogenated rosin triglyceride (hydrogenated ester gum), rosin triglyceride (ester gum), glyceryl behenate eicosanedioate, glyceryl di-2-heptylundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl esters of macadamia nut oil fatty acids, phytosteryl esters of macadamia nut oil fatty acids, phytosteryl isostearate, cholesteryl esters of soft lanolin fatty acids, cholesteryl esters of hard lanolin fatty acids, cholesteryl esters of long-chain branched fatty acids, cholesteryl esters of long-chain α-hydroxyfatty acids, octyldodecyl ricinoleate, octyldodecyl esters of lanolin fatty acids, octyldodecyl erucate, hydrogenated castor oil isostearate, ethyl esters of avocado oil fatty acids, and isopropyl esters of lanolin fatty acids.

Besides the preceding, the cosmetic and topical skin preparation of the present invention may use, for example, an oil or fat, a higher fatty acid, a fluorooil, and so forth, as an oil, and combinations of two or more of the preceding may also be used. For example, two or more of the oils indicated below may be used in combination. Specific examples are provided below of oils other than silicone oils, hydrocarbon oils, and fatty acid ester oils that may be used by the present invention. In particular, when incorporated in a cosmetic or topical skin preparation, oils and fats of plant origin provide a healthy image deriving from natural substances and have an excellent moisturizing behavior and an excellent skin absorbability/compatibility and for these reasons are well suited for use in the cosmetic and topical skin preparation of the present invention. These oils are particularly preferably incorporated in the range from 0.5 to 25 mass % of the cosmetic or topical skin preparation as a whole. The co-use of the higher alcohol-modified silicone (A) and the higher alcohol (B) according to the present invention with these oils makes it possible to stably incorporate these oils in the cosmetic and topical skin preparation without impairing the distinctive suede-like tactile feel and has the additional advantage of realizing a moisturizing function, protection against drying, and so forth.

These oils and fats can be exemplified by plant and animal oils and fats of natural origin such as avocado oil, linseed oil, almond oil, *Ericerus pela* (Chavannes) wax, *perilla* oil, olive oil, cacao butter, Kapok tree wax, kaya oil, carnauba wax, cod liver oil, candelilla wax, beef tallow, hardened beef tallow, apricot kernel oil, spermaceti wax, hardened oils, wheat germ oil, sesame oil, rice germ oil, rice bran oil, sugarcane wax, camellia Kissi seed oil, safflower oil, shea butter, Paulownia oil, cinnamon oil, jojoba wax, olive squalane, shellac wax, turtle oil, soybean oil, tea seed oil, camellia oil, evening primrose oil, corn oil, lard, rape-seed oil, Japanese tung oil, bran wax, germ oil, horse fat, persic oil, palm oil, palm kernel oil, castor oil, hydrogenated castor oil, methyl esters of castor oil fatty acids, sunflower oil, grape seed oil, bayberry wax, jojoba oil, hydrogenated jojoba esters, macadamia nut oil, yellow beeswax, mink oil, cottonseed oil, cotton wax, Japan wax, sumac kernel oil, montan wax, palm oil, hardened palm oil, cocofatty acid triglycerides, mutton tallow, peanut oil, lanolin, liquid lanolin, reduced lanolin, lanolin alcohol, hardened lanolin, lanolin acetate, isopropyl esters of lanolin fatty acids, POE lanolin alcohol ethers, POE lanolin alcohol acetate, polyethylene glycol esters of lanolin fatty acids, POE hydrogenated lanolin alcohol ethers, POE cholesterol ethers, monostearyl glycerol ether (batyl alcohol), monooleyl glyceryl ether (selachyl alcohol), yolk oil, and so forth. Here, POE denotes polyoxyethylene.

The higher fatty acids can be exemplified by lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, 12-hydroxystearic acid, and so forth.

The fluorooil can be exemplified by perfluoropolyethers, perfluorodecalin, perfluorooctane, and so forth.

The cosmetic and topical skin preparation of the present invention may further contain at least one silicone resin (E). This silicone resin (E) is an organopolysiloxane that has a highly branched structure, a network structure, or a cage structure; is a liquid or solid at ambient temperature; and may be any silicone resin ordinarily used in cosmetics insofar as the objects of the present invention are not impaired. In the case of a solid, the silicone resin may be a particulate such as a spherical powder, scale-like powder, acicular powder, or flat flake-like powder including disk-shaped powders that generally have an appearance seen as disk-like and the aspect ratio of a particle, and a silicone resin powder that contains the monoorganosiloxy unit (T unit) and/or siloxy unit (Q unit) described below is particularly suitably used. The incorporation of a silicone resin (E) in combination with the higher alcohol-modified silicone (A) according to the present invention improves the compatibility and uniform dispersibility for an oil-based system as a whole that contains an oil and a higher alcohol and is useful, accompanying the incorporation of the silicone resin (E), from the standpoint of obtaining an improvement in the tactile feel of the cosmetic and an improvement in the use sensation in terms of a uniform adherence to the region of application.

The solid silicone resin includes, for example, an MQ resin, MDQ resin, MTQ resin, MDTQ resin, TD resin, TQ resin, or TDQ resin comprising any combination of the triorganosiloxy unit (M unit) wherein the organo group is only the methyl group or is the methyl group and vinyl or phenyl group; the diorganosiloxy unit (D unit) wherein the organo group is only the methyl group or is the methyl group and vinyl or phenyl group; the monoorganosiloxy unit (T unit) wherein the organo group is the methyl group, vinyl group, or phenyl group; and the siloxy unit (Q unit). Examples are trimethylsiloxysilicic acid, polyalkylsiloxysilicic acid, dimethylsiloxy unit-containing trimethylsiloxysilicic acid, and alkyl(perfluoroalkyl)siloxysilicic acid. The silicone resin is particularly preferably oil soluble and dissolvable in volatile silicone.

Preferred silicone resins (E) for the cosmetic and topical skin preparation of the present invention are silicone resins that contain at least the monoorganosiloxy unit (T unit) and/or the siloxy unit (Q unit); these silicone resins are preferably incorporated in the range from 0.1 to 10 mass % of the cosmetic as a whole. When these branching units are present, the network-structured silicone resin, when applied on the skin or hair, forms a uniform film and provides a protective effect against drying and low temperatures and can also stop the unwanted removal or disarrangement of a cosmetic in the presence of sebum due to sweating. In addition, a silicone resin powder having these branching units securely adheres on the skin or hair and can impart a glossy and transparent perception to the skin or hair. In particular, a high phenyl content, high refractive index phenylsilicone resin powder, for example, 217 Flake Resin from Dow Corning Toray Co., Ltd., can readily form a silicone resin flake powder and, when incorporated in a cosmetic, can impart a lustrous and transparent perception to the skin or hair while maintaining the suede-like tactile feel of the higher alcohol-modified silicone (A) according to the present invention.

The cosmetic and topical skin preparation of the present invention may also incorporate at least one particulate or liquid silicone elastomer (F). The higher alcohol-modified silicone (A) according to the present invention provides a cosmetic with a suede-like tactile feel, as when a silicone elastomer powder is dispersed in an oil, and has an excellent blendability with the ingredients of silicone systems. As a consequence, when a silicone elastomer (F) and the higher alcohol-modified silicone (A) are both incorporated, this improves the compatibility and uniform dispersibility for an oil-based system as a whole that contains an oil and a higher alcohol, and, when freshly spread on the skin, this also offers the advantages—which accrue without a loss of the distinctive suede-like tactile feel—of diminishing the appearance of peaks and valleys in the skin and, unlike an oil, providing a natural impression by inhibiting an oily sheen by the skin and an oily gloss.

The silicone elastomer (F) may be incorporated in the cosmetic and topical skin preparation in any form in conformity with the purpose of the silicone elastomer (F); however, incorporation as a spherical organopolysiloxane elastomer powder or crosslinked organopolysiloxane is preferred.

Spherical silicone elastomer powder is the crosslinked product from a straight-chain diorganopolysiloxane comprising mainly the diorganosiloxy unit (D unit) and can be suitably obtained by a crosslinking reaction in the presence of a hydrosilylation reaction catalyst between an organohydrogenpolysiloxane that has silicon-bonded hydrogen in side chain or terminal position and a diorganopolysiloxane that has an unsaturated hydrocarbyl group, e.g., an alkenyl group, in side chain or terminal position. This silicone elastomer powder is softer and more elastic than a silicone resin powder composed of the previously described T unit and/or Q unit; it also exhibits an excellent oil absorptivity and thus has the advantage of being able to absorb the sebum on the skin and prevent unwanted removal or disarrangement of the cosmetic. In addition, by carrying out surface treatment with the higher alcohol-modified silicone (A) according to the present invention, a moist tactile feel can be provided without reducing the suede-like tactile feel of the silicone elastomer powder. Furthermore, incorporation in combination with a silicone elastomer powder also accrues the advantages of improving the dispersion stability for the cosmetic as a whole and of making possible the preparation of a cosmetic composition that is timewise stable. The proportions for the surface treatment are preferably 0.1 to 10 mass parts of the higher alcohol-modified silicone (A) per 100 mass parts of the silicone elastomer powder. The effect due to the surface treatment may be inadequate when the treatment quantity is less than the indicated lower limit. At a treatment quantity above the indicated upper limit, there is no additional significant change in the texture or material feel and a uniform mixture of the higher alcohol-modified silicone with the silicone elastomer powder appears. Accordingly, there is no hindrance—when the objective is the preparation of a uniform dispersion—to the formation of a higher alcohol-modified silicone dispersion of the powder by carrying out surface treatment with a quantity of the higher alcohol-modified silicone in excess of the previously indicated upper limit.

The silicone elastomer powder may take various shapes, e.g., spherical, flattened, irregular, and so forth. It may also take the form of an oil dispersion that lacks a shape. Preferred for incorporation in the cosmetic and topical skin preparation of the present invention is a silicone elastomer powder that is a silicone elastomer having a particulate shape, that has a primary particle size by electron microscopic observation and/or an average primary particle size as measured by laser diffraction/scattering in the range from 0.1 to 50 µm, and that has a spherical primary particle shape. The silicone elastomer constituting the silicone elastomer powder has a Type A durometer hardness of preferably no more than 80 and more preferably no more than 65 according to JIS K 6253, "Rubber, vulcanized or thermoplastic—Determination of hardness".

The spherical organopolysiloxane elastomer powder may or may not be subjected to a surface treatment with, for example, a silicone resin or silica. Examples are described in JP 02-243612 A, JP 08-012545 A, JP 08-012546 A, JP 08-012524 A, JP 09-241511 A, JP 10-036219 A, JP 11-193331 A, JP 2000-281523 A, and so forth. Commercially available spherical organopolysiloxane elastomer powders that correspond to the crosslinked silicone powder listed in the "Japanese Cosmetic Ingredients Codex" can be exemplified by Trefil E-506S, Trefil E-508, 9701 Cosmetic Powder, and 9702 Powder, all from Dow Corning Toray Co., Ltd. These silicone elastomer powders may be subjected to a surface treatment. Examples of the surface treatment agent include methylhydrogenpolysiloxane; silicone resins; metal soaps; silane coupling agents; inorganic oxides such as silica, titanium oxide, and so forth; and fluorocompounds such as perfluoroalkylsilanes, perfluoroalkyl phosphate ester salts, and so forth.

The spherical organopolysiloxane elastomer powder may also be used in the cosmetic and topical skin preparation of the present invention in the form of a water-based dispersion. Commercially available water-based dispersions of this type can be exemplified by BY 29-129, PF-2001, and PIF Emulsion from Dow Corning Toray Co., Ltd. The incorporation of these water-based silicone elastomer powder dispersions or suspensions is very useful from the standpoint of further improving the use sensation of the cosmetic of the present invention and particularly the use sensation of the oil-in-water emulsion-type cosmetic.

The crosslinked organopolysiloxane preferably has a structure in which the organopolysiloxane chain has been three-dimensionally crosslinked by a reaction with a crosslinking component comprising a polyether unit, a $C_{4-20}$ alkylene unit, or an organopolysiloxane unit.

Specifically, this crosslinked organopolysiloxane can be obtained by reacting an organohydrogenpolysiloxane that contains silicon-bonded hydrogen with a polyether compound that has an unsaturated bond at both molecular chain terminals, an unsaturated hydrocarbon that has more than 1 double bond in the molecule, or an organopolysiloxane that has more than 1 double bond in the molecule. The crosslinked organopolysiloxane may or may not contain a modifying functional group, e.g., an unreacted silicon-bonded hydrogen, an aromatic hydrocarbyl group such as the phenyl group, a $C_{6-30}$ long-chain alkyl group such as the octyl group, a polyether group, the carboxyl group, a silylalkyl group having a carbosiloxane dendrimer structure as described above, and so forth, and can be used without limitation with regard to, for example, the method of production or physical state such as dilution, properties, and so forth.

For example, the crosslinked organopolysiloxane under consideration can be obtained by an addition reaction between an organohydrogenpolysiloxane that is composed of structural units selected from the group consisting of the $SiO_2$ unit, $HSiO_{1.5}$ unit, $R^b SiO_{1.5}$ unit, $R^b HSiO$ it, $R^b_2 SiO$ unit, $R^b_3 SiO_{0.5}$ unit, and $R^b_2 HSiO_{0.5}$ unit—wherein R is a substituted or unsubstituted $C_{1-30}$ monovalent hydrocarbyl group excluding aliphatically unsaturated groups and a portion of $R^b$ is a $C_{8-30}$ monovalent hydrocarbyl group—and that contains on average at least 1.5 silicon-bonded hydrogen atoms in the molecule and a crosslinking component selected from a polyether compound that is, for example, a polyoxyalkylene compound or polyglycerol compound or polyglycidyl compound that has an unsaturated hydrocarbyl group at both molecular chain terminals, an unsaturated hydrocarbon that is an α,ω-diene with the general formula $CH_2=CH-C_r H_{2r}-C=H=CH_2$ wherein r is an integer from 0 to 26, and an organopolysiloxane that is composed of structural units selected from the group consisting of the $SiO_2$ unit, $(CH_2=CH)SiO_{1.5}$ unit, $R^c SiO_{1.5}$ unit, $R^c(CH_2=CH)SiO$ unit, $R^c_2 SiO$ unit, $R^c_3 SiO_{0.5}$ unit, and $R^c_2(CH_2=CH)SiO_{0.5}$ unit wherein $R^c$ is a substituted or unsubstituted $C_{1-30}$ monovalent hydrocarbyl group excluding aliphatically unsaturated groups and that contains on average at least 1.5 silicon-bonded vinyl groups in the molecule. The previously indicated modifying functional groups can be introduced via an addition reaction at unreacted silicon-bonded hydrogen atoms. For example, the hexyl group, which is the $C_6$ alkyl group, can be introduced by reacting 1-hexene with a crosslinked organopolysiloxane that contains unreacted silicon-bonded hydrogen.

Crosslinked organopolysiloxanes as described above can be used without limitation with regard to, for example, the method of production or physical state such as dilution, properties, and so forth, but a particularly preferred crosslinked organopolysiloxane is the α,ω-diene-crosslinked silicone elastomer described in U.S. Pat. No. 5,654,362, available commercially as DC 9040 Silicone Elastomer Blend, DC 9041 Silicone Elastomer Blend, DC 9045 Silicone Elastomer Blend, and DC 9046 Silicone Elastomer Blend, all from the Dow Corning Corporation (US). Similarly, partially crosslinked organopolysiloxane polymers can be exemplified, using the labeling names according to the International Nomenclature of Cosmetic Ingredients (INCI), by (dimethicone/vinyldimethicone) crosspolymer, (dimethicone/phenylvinyldimethicone) crosspolymer, (PEG-8-30/C6-C30 alkyldimethicone) crosspolymer, (vinyldimethicone/C6-C60 alkyldimethicone) crosspolymer, and (dimethicone/polyglycerin) crosspolymer.

When an emulsifiable crosslinked organopolysiloxane that has been crosslinked by a polyether compound is incorporated as a component in the cosmetic or topical skin preparation, the higher alcohol-modified silicone (A) according to the present invention, because it functions as a surfactant or a co-surfactant, has the advantage of making possible the formation of a uniform emulsion system. Furthermore, for systems that contain a higher alcohol plus water, the ability of the crosslinked organopolysiloxane to function as a surfactant has the advantages of making possible, even at a small quantity of addition, the formation of a stable water-containing gel structure and the preparation of a water-containing cosmetic, water-containing topical skin preparation, or emulsion cosmetic that is soft and exhibits an excellent water retention.

When, on the other hand, a non-emulsifiable crosslinked organopolysiloxane that has been crosslinked by an organopolysiloxane or an unsaturated hydrocarbyl group such as a diene is incorporated as a component in the cosmetic, the elastomeric suede-like tactile feel possessed by the higher alcohol-modified silicone (A) according to the present invention is even more strongly supported and the perception of adherence to the skin is improved. Moreover, the compatibility with other oil system ingredients is excellent, which has the advantage of making possible the stable incorporation in the cosmetic or topical skin preparation with the generation of a uniform oil system as a whole.

One or two or more of these silicone elastomers can be incorporated in conformity with the objective therefor, and, depending on the objective therefor and the intent of the incorporation, incorporation in the range from 0.05 to 25 mass % of the cosmetic as a whole is preferred and incorporation in the range from 0.1 to 15 mass % is particularly preferred.

In addition to the components described in the preceding, the cosmetic and topical skin preparation of the present invention may contain various other cosmetic ingredients and physiologically active components. These ingredients preferably do not completely dissolve in water or are hydrophobic to the extent that the solubility of the particular component in 100 g water is less than 1 mass %. These cosmetic ingredients can be exemplified by powders, colorants, water-soluble polymers, oil-soluble gellants, organomodified clay minerals, silicone gums, organomodified silicones, ultraviolet protective components, and so forth.

The cosmetic of the present invention may incorporate without particular limitation the powders and/or colorants used in ordinary cosmetics as a cosmetic base material or substrate or used in ordinary cosmetics for the purpose, for example, of improving the tactile feel of the cosmetic or coloring the cosmetic. Any of these powders and/or colorants can be used regardless of shape, e.g., spherical, rod-shaped, needle-shaped, plate-shaped, irregular, spindle-shaped, and so forth; particle size, e.g., aerosol, microparticulate, pigment grade, and so forth; and particle structure, e.g., porous, non-porous, and so forth. However, when these powders and/or colorants are incorporated as pigments, the incorporation is preferred of one or two or more selections from inorganic pigment powders, organic pigment powders, and resin powders that have an average primary particle size in the range from 1 nm to 100 µm.

The powder and/or colorant can be exemplified by inorganic powders, organic powders, metal salt powder surfactants, i.e., metal soaps, colored pigments, pearlescent pigments, metal powder pigments, and so forth; composites of these pigments may also be used. In specific terms, the inorganic powder can be exemplified by titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic anhydride, aluminum silicate, sodium silicate, sodium magnesium silicate, magnesium silicate, aluminum magnesium silicate, calcium silicate, barium silicate, strontium silicate, metal salts of tungstic acid, hydroxyapatite, vermiculite, higilite, bentonite, montmorillonite, hectorite, zeolite, ceramic powders, calcium secondary phosphate, alumina, aluminum hydroxide, boron nitride, and so forth; the organic powder can be exemplified by polyamide powder, polyester powder, polyethylene powder, polypropylene powder, polystyrene powder, polyurethane powder, benzoguanamine powder, polymethylbenzoguanamine powder, polytetrafluoroethylene powder, polymethyl methacrylate powder, cellulose, silk powder, nylon powder, nylon 12, nylon 6, silicone powder, spherical polymethylsilsesquioxane powder, styrene-acrylic acid copolymer, divinylbenzene.styrene copolymer, vinyl resin, urea resin, phenolic resin, fluororesin, silicon resin, acrylic resin, melamine resin, epoxy resin, polycarbonate resin, microcrystalline fiber powder, starch powder, and lauroyllysine; the metal salt powder surfactant can be exemplified by zinc stearate, aluminum stearate, calcium stearate, magnesium stearate, zinc myristate, magnesium myristate, zinc palmitate, zinc laurate, zinc cetyl phosphate, calcium cetyl phosphate, and sodium zinc cetyl phosphate; the colored pigment can be exemplified by inorganic red pigments such as iron oxide red, iron oxide, iron hydroxide, and iron titanate, inorganic brown pigments such as γ-iron oxide, inorganic yellow pigments such as iron oxide yellow and ocher, inorganic black pigments such as iron oxide black and carbon black, inorganic purple pigments such as Manganese Violet and Cobalt Violet, inorganic green pigments such as chromium hydroxide, chromium oxide, cobalt oxide, and cobalt titanate, inorganic blue pigments such as Prussian blue and ultramarine blue, the lakes of tar dyes such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207, and the lakes of natural dyes such as carminic acid, laccaic acid, carthamin, brazilin, and crocin; the pearlescent pigment can be exemplified by titanium oxide-coated mica, titanium mica, iron oxide-treated titanium mica, bismuth oxychloride, titanium oxide-coated bismuth oxychloride, titanium oxide-coated talc, fish scale foil, and titanium oxide-coated colored mica; and the metal powder pigment can be exemplified by powders of metals such as aluminum, gold, silver, copper, platinum, and stainless steel.

All or a portion of the powder and/or colorant is particularly preferably subjected to a surface treatment such as a hydrophobing treatment or a hydrophilicizing treatment.

Composites may also be formed between/among these powders and/or colorants; a powder and/or colorant may be used that has been subjected to a surface treatment with, e.g., an ordinary oil, a silicone compound other than the organopolysiloxane copolymer according to the present invention, a fluorine compound, a surfactant, or a thickener; and as necessary a single powder or colorant can be used or two or more powders and/or colorants can be used. These powders and/or colorants are suitably incorporated at 0.1 to 99 mass % of the cosmetic as a whole. As a particular matter, the quantity of incorporation in the case of a solid powder-form cosmetic is suitably 80 to 99 mass % of the cosmetic as a whole since in this case the powder and/or colorant forms the base of the cosmetic.

Hydrophobing treatments other than the preceding can be exemplified by treatment of the previously described powder and/or colorant with various hydrophobing surface-treatment agents, for example, treatment with an organosiloxane such as treatment with a methylhydrogenpolysiloxane, treatment with a silicone resin, treatment with a silicone gum, treatment with an acrylsilicone, and treatment with a fluorosilicone; treatment with a metal soap such as treatment with zinc stearate; treatment with a silane such as treatment with a silane coupling agent and treatment with an alkylsilane; treatment with a fluorine compound such as treatment with a perfluoroalkylsilane, a perfluoroalkyl phosphate ester salt, or a perfluoropolyether; treatment with an amino acid such as treatment with N-lauroyl-L-lysine; treatment with an oil such as treatment with squalane; and an acrylic treatment such as treatment with an alkyl acrylate. Combinations of more than one of these may also be used.

These powders and/or colorants form a uniform dispersion when mixed in advance with the higher alcohol-modified silicone and are therefore preferably incorporated in the cosmetic by mixing to uniformity in advance with all or a portion of the higher alcohol-modified silicone.

The water-soluble polymer is incorporated for the purpose of producing a cosmetic in a desired formulation and/or for the purpose of improving the use sensation of the cosmetic, such as improving the tactile feel and conditioning effect with hair, and so forth. Any amphoteric, cationic, anionic, or nonionic water-soluble polymer or water-swellable clay mineral that is ordinarily used in cosmetics can be used as this water-soluble polymer, and a single water-soluble polymer may be used or two or more may be used in combination. Since these water-soluble polymers have a thickening effect on water-containing components, they are particularly useful for obtaining a water-containing cosmetic gel, a water-in-oil emulsion-type cosmetic, or an oil-in-water emulsion-type cosmetic. Natural water-soluble polymers can be exemplified by plant-derived polymers such as gum arabic, tragacanth gum, galactan, guar gum, carob gum, karaya gum, carrageenan, pectin, agar, quince seed (*Cydonia oblonga*), algae colloid (brown algae extract), starch, e.g., rice, corn, potato, and wheat, and glycyrrhizic acid; by microbial-derived polymers such as xanthan gum, dextran, succinoglucan, and pullulan; and by animal-derived polymers such as collagen, casein, albumin, and gelatin. Semisynthetic water-soluble polymers can be exemplified by starch-type polymers such as carboxymethyl starch and methylhydroxypropyl starch; cellulosic polymers such as methyl cellulose, nitrocellulose, ethyl cellulose, methylhydroxypropyl cellulose, hydroxyethyl cellulose, sodium cellulose sulfate, hydroxypropyl cellulose, sodium carboxymethyl cellulose (CMC), crystalline cellulose, and cellulose powder; and alginic acid-type polymers such as sodium alginate and propylene glycol alginate. Synthetic water-soluble polymers can be exemplified by vinyl-type polymers such as polyvinyl alcohol, polyvinyl methyl ether-type polymers, polyvinylpyrrolidone, and carboxyvinyl polymers (CARBOPOL 940 and 941 from Lubrizol Japan Limited); polyoxyethylene-type polymers such as polyethylene glycol 20,000, polyethylene glycol 6,000, and polyethylene glycol 4,000; copolymer-type polymers such as polyoxyethylene-polyoxypropylene copolymers and PEG/PPG methyl ether; acrylic polymers such as sodium polyacrylate, polyethyl acrylate, and polyacrylamide; as well as polyethyleneimine and cationic polymers. The water-swellable clay mineral is an inorganic water-soluble polymer and is a type of colloid-containing aluminum silicate having a three-layer structure and can be specifically exemplified by bentonite, montmorillonite, beidellite, nontronite, saponite, hectorite, aluminum magnesium silicate, and silicic anhydride. These may be either the natural or synthetic material.

Other cationic water-soluble polymers, and particularly components that can be suitably incorporated in hair cosmetics, can be exemplified by quaternary nitrogen-modified polysaccharides, for example, cation-modified cellulose, cation-modified hydroxyethyl cellulose, cation-modified guar gum, cation-modified locust bean gum, and cation-modified starch; dimethyldiallylammonium chloride derivatives, for example, dimethyldiallylammonium chloride-acrylamide copolymers and polydimethylmethylenepiperidinium chloride; vinylpyrrolidone derivatives, for example, vinylpyrrolidone-dimethylaminoethyl methacrylate copolymer salts, vinylpyrrolidone-methacrylamidopropyltrimethylammonium chloride copolymers, and vinylpyrrolidone-methylvinylimidazolium chloride copolymers; and methacrylic acid derivatives, for example, methacryloylethyldimethylbetaine-methacryloylethyltrimethylammonium chloride-2-hydroxyethyl methacrylate copolymer, and methacryloylethyldimethylbetaine-methacryloylethyltrimethylammonium chloride-methoxypolyethylene glycol methacrylate copolymer.

An amphoteric water-soluble polymer is a particular example of a component that can be favorably incorporated in a hair cosmetic and can be specifically exemplified by amphoterized starch; dimethyldiallylammonium chloride derivatives such as, for example, acrylamide-acrylic acid-dimethyldiallylammonium chloride copolymers and acrylic acid-dimethyldiallylammonium chloride copolymers; and methacrylic acid derivatives such as, for example, polymethacryloylethyldimethylbetaine, (methacryloyloxyethylcarboxybetaine/alkyl methacrylate) copolymers, (octylarylamide/hydroxypropyl acrylate/butylaminoethyl methacrylate) copolymers, and N-methacryloyloxyethyl-N,N-dimethylammonium-α-methylcarboxybetaine.alkyl methacrylate copolymers.

The higher alcohol-modified silicone (A) of the present invention forms a stable gel structure in a higher alcohol/water/surfactant system, while the incorporation of the previously described water-soluble polymer brings about an increase in the viscosity of the water-containing cosmetic as a whole—even for a system that does not contain a higher alcohol or for a system that has a low higher alcohol content—and has the advantage of making it possible to obtain a stable water-based cosmetic gel or emulsion cosmetic in which the separation of oily ingredients with elapsed time is inhibited.

In addition, when the cosmetic of the present invention is used as an oil-in-water emulsion-type cosmetic and particularly as a hair cosmetic, the incorporation of the previously described water-soluble polymer offers the advantages of providing a conditioning effect, i.e., the hair is flexible, smooth, and not stiff, and providing a velvety tactile feel for the foam.

These conditioning effects are effectively manifested in particular by the incorporation of a cationic water-soluble polymer and the incorporation of an amphoteric water-soluble polymer. For the cosmetic of the present invention, the incorporation of an ionic water-soluble polymer such as a cation-modified guar gum or an amphoteric water-soluble polymer also has the advantage of inhibiting the crystallization of the higher alcohol (B) just as for an ionic surfactant. Specifically, the incorporation of an ionic water-soluble polymer, a higher alcohol (B), and the higher alcohol-modified silicone (A) in a hair cosmetic enables a thorough rinsing out of the individual components and the realization of an excellent hair combability post-use and the good tactile feel of well-behaved hair as a whole—while providing the hair with the light, soft tactile feel and volume sensation that originate with the higher alcohol and higher alcohol modifying group.

Similarly, the co-use of these water-soluble polymers has the advantage of making possible further improvements in the hair-repair effect and split end-preventing effect that originate with the higher alcohol-modified silicone (A). In particular, the incorporation of a cationic water-soluble polymer and the higher alcohol-modified silicone (A) provides a smooth finger run when the hair is shampooed, keeps the hair soft during shampooing, and provides a well-balanced conditioning effect from the hair root to the hair end.

The quantity of incorporation of the previously described water-soluble polymer in the cosmetic of the present invention can be selected as appropriate in conformity with the type and purpose of the cosmetic, but is in the range from 0.01 to 5.0 mass % of the cosmetic as a whole and is more preferably in the range from 0.1 to 3.0 mass % to obtain a particularly good use sensation. When the quantity of water-soluble polymer incorporation exceeds the upper limit given above, a rough tactile feel may remain for the hair or skin depending on the type of the cosmetic. At below the previously indicated lower limit, the advantageous technical effects, e.g., the thickening effect, the conditioning effect, and so forth, may not be adequately realized.

The oil-soluble gellant is a gellant of the oily components, such as the previously described oils, and, when the cosmetic of the present invention is an oil-based cosmetic wherein the continuous phase is an oily component, is a component that can realize a desired formulation and tactile feel through thickening/gelation of the oily component. This oil-soluble gellant can be exemplified by metal soaps such as aluminum stearate, magnesium stearate, and zinc myristate; amino acid derivatives such as N-lauroyl-L-glutamic acid and α,γ-di-n-butylamine; dextrin fatty acid esters such as dextrin palmitate, dextrin stearate, and dextrin 2-ethylhexanoate palmitate; sucrose fatty acid esters such as sucrose palmitate and sucrose stearate; and the benzylidene derivatives of sorbitol such as monobenzylidene sorbitol and dibenzylidene sorbitol. A single one of the preceding or two or more can be used as necessary.

The quantity of incorporation of the oil-soluble gellant in the cosmetic of the present invention is in the range from 0.5 to 50 mass parts per 100 mass parts of the oily component, such as an oil, and more preferably is in the range from 1 to 30 mass parts. The incorporation of the oil-soluble gellant in the cosmetic of the present invention makes it possible—while maintaining the suede-like tactile feel that originates with the higher alcohol-modified silicone (A)—to make appropriate adjustments to the viscosity and hardness (softness) of the oil ingredient-containing cosmetic as a whole and to accrue the advantages of improving the handling properties of the cosmetic, improving the formulation spectrum (selectability), improving the timewise stability, improving the high-temperature stability, and improving the blend stability. In addition, when a cosmetic that incorporates an oil-based gel composition is applied to the skin or hair, a good subsidence is obtained during spreading and an excellent sensation stability and an excellent adherence are obtained. In addition to the characteristic use sensation of the higher alcohol-modified silicone (A), the advantages also accrue from a quality standpoint of inhibiting the oiliness, i.e., the oily sticky tactile feel, as a whole and improving the durability of the cosmetic.

The organomodified clay mineral can be used, like the previously described oil-soluble gellant, as a gellant for the oily component, e.g., an oil. This organomodified clay mineral can be exemplified by dimethylbenzyldodecylammonium montmorillonite clay, dimethyldioctadecylammonium montmorillonite clay, dimethylalkylammonium hectorite, benzyldimethylstearylammonium hectorite, and distearyldimethylammonium chloride-treated aluminum magnesium silicate. Commercially available products here are Bentone 27, a benzyldimethylstearylammonium chloride-treated hectorite from the National Lead Co., and Bentone 38, a distearyldimethylammonium chloride-treated hectorite from the National Lead Co.

The silicone gum is a straight-chain diorganopolysiloxane with an ultrahigh degree of polymerization and is also known as an organopolysiloxane gum. Due to its high degree of polymerization, a silicone gum has a measurable plasticity, which distinguishes it from the previously described silicone oils. The silicone gum can be incorporated in the cosmetic according to the present invention either directly or in the form of a liquid gum dispersion in which it is dispersed in a silicone oil, i.e., an oil dispersion of the silicone gum.

The silicone gum can be exemplified by substituted and unsubstituted organopolysiloxanes that contain the dialkylsiloxy unit (D unit), for example, dimethylpolysiloxanes, methylphenylpolysiloxanes, aminopolysiloxanes, methylfluoroalkylpolysiloxanes, and so forth, and also by the preceding having a very lightly crosslinked structure. A typical example has the general formula $R^{10}(CH_3)_2SiO\{(CH_3)_2SiO\}_s\{(CH_3)R^{11}SiO\}_tSi(CH_3)_2R^{10}$ wherein $R^{11}$ is a group selected from the vinyl group, phenyl group, $C_{6-20}$ alkyl groups, $C_{3-15}$ aminoalkyl groups, $C_{3-15}$ perfluoroalkyl groups, and $C_{3-15}$ quaternary ammonium salt-containing alkyl groups; the $R^{10}$ terminal group is a group selected from $C_{1-8}$ alkyl groups, the phenyl group, the vinyl group, $C_{3-15}$ aminoalkyl groups, the hydroxyl group, and $C_{1-8}$ alkoxy groups; s=2,000 to 6,000; t=0 to 1,000; and s+t=2,000 to 6,000. Preferred thereamong are dimethylpolysiloxane gums that have a degree of polymerization of 3,000 to 20,000. Also preferred are amino-modified methylpolysiloxane gums that have, for example, the 3-aminopropyl group or N-(2-aminoethyl)-3-aminopropyl group in side chain or terminal position in the molecule. A single silicone gum or a combination of two or more silicone gums may be used as necessary in the present invention.

Due to its ultrahigh degree of polymerization, the silicone gum forms a protective film on the skin or hair; this protective film exhibits an excellent residual behavior and an excellent air permeability. As a consequence, this component in particular can impart gloss and luster to hair and can impart resilience and body to the hair as a whole both during and after use. On the other hand, the incorporation of a silicone gum can result in the appearance of a rough feel by the hair surface, particularly after drying. However, in the cosmetic of the present invention, and particularly in the case of an oil-in-water emulsion-type hair cosmetic of the present invention, the higher alcohol-modified silicone (A) functions as a surfactant and also inhibits the crystallization of other higher alcohols, and as a consequence—while the unique use sensation originating with the higher alcohol-modified silicone (A) is maintained—the silicone gum becomes easy to wash out to a suitable degree and its conditioning effect is improved while a smooth, well-behaved state is also maintained for the hair after drying.

The quantity of silicone gum incorporation is in the range from 0.05 to 30 mass % of the cosmetic as a whole and is preferably in the range from 1 to 15 mass %. A silicone gum may be easily incorporated through the use of an emulsion composition prepared in advance via an emulsification process, which also includes emulsion polymerization, and can also be stably incorporated in various cosmetics in the present invention. A quantity of silicone gum incorporation below the previously indicated lower limit can result in an inadequate generation of the characteristic tactile feel and an inadequate generation of luster by the hair.

The organomodified silicone is a silicone compound in which a functional group has been introduced into a portion of the polysiloxane chain; this is an organomodified silicone other than the component (A) higher alcohol-modified silicone and is a component that can be incorporated in a cosmetic. Specific examples are amino-modified silicones, aminopolyether-modified silicones, epoxy-modified silicones, carboxyl-modified silicones, amino acid-modified silicones, acrylic-modified silicones, phenol-modified silicones, amidoalkyl-modified silicones, aminoglycol-modified silicones, alkoxy-modified silicones, and $C_{8-30}$ higher alkyl-modified silicones.

This organomodified silicone may have an alkylene chain, aminoalkylene chain, or polyether chain in the main chain in addition to the polysiloxane bond and thus encompasses so-called block copolymers. Moreover, the previously described organic modifying group may be present in side chain position and/or terminal position on the polysiloxane chain.

When the cosmetic of the present invention is used as a hair cosmetic, the higher alcohol-modified silicone (A) of the present invention can be favorably used in combination with an amino-modified silicone, e.g., amodimethicone or a high degree of polymerization amino gum, or an aminopolyether-modified silicone or an aminoglycol-modified silicone, wherein a typical example is an amino-modified silicone that contains, for example, the 3-aminopropyl group or N-(2-aminoethyl)-3-aminopropyl group.

A single one of these modified silicones or two or more of these modified silicones can be incorporated in conformity with the objective therefor. These modified silicones can function as the previously described silicone-type surfactant, and/or can function as a powder-treatment agent, and can manifest such functions as improving the smoothness and luster of hair and particularly improving the tactile feel post-rinse. The quantity of modified silicone incorporation in the cosmetic of the present invention is, in conformity with the objective and intent of incorporation therefor, preferably in the range from 0.05 to 25 mass % of the cosmetic as a whole and particularly preferably in the range from 0.1 to 15 mass %. The sought-after function of the organomodified silicone may not be adequately manifested when the quantity of modified silicone incorporation is less than the previously indicated lower limit, while the balance between, inter alia, the tactile feel and functionality of the cosmetic may be impaired at a quantity of incorporation above the previously indicated upper limit.

The ultraviolet protective component encompasses inorganic ultraviolet protective components and organic ultraviolet protective components. When the cosmetic of the present invention is a sunscreen cosmetic, it preferably contains at least one inorganic or organic ultraviolet protective component and particularly preferably at least one organic ultraviolet protective component.

The inorganic ultraviolet protective component may be, for example, an inorganic pigment powder or metal powder pigment as described above, incorporated as an agent that scatters ultraviolet radiation, and can be exemplified by metal oxides such as titanium oxide, zinc oxide, cerium oxide, low-order titanium oxide, and iron-doped titanium oxide; metal hydroxides such as iron hydroxide; metal flake such as iron oxide plates and aluminum flake; and ceramics such as silicon carbide. Particularly preferred thereamong is at least one selection from finely divided metal oxides and finely divided metal hydroxides that have an average particle size in the range from 1 to 100 nm and have a granular, plate, acicular, or fibrous shape. These powders are preferably subjected to a heretofore known surface treatment, for example, treatment with a fluorine compound and preferably treatment with a perfluoroalkyl phosphate ester, treatment with a perfluoroalkylsilane, treatment with a perfluoropolyether, treatment with a fluorosilicone, or treatment with a fluorinated silicone resin; treatment with a silicone and preferably treatment with a methylhydrogenpolysiloxane, treatment with a dimethylpolysiloxane, or treatment with tetramethyltetrahydrogencyclotetrasiloxane by a gas-phase method; treatment with a silicone resin and preferably treatment with a trimethylsiloxysilicic acid; pendant treatment, i.e., a method in which treatment with a silicone by a gas-phase method is followed by the addition of, e.g., an alkyl chain; treatment with a silane coupling agent; treatment with a titanium coupling agent; treatment with a silane and preferably treatment with an alkylsilane or alkylsilazane; treatment with an oil; treatment with an N-acylated lysine; treatment with a polyacrylic acid; treatment with a metal soap wherein a salt of stearic acid or myristic acid is preferred; treatment with an acrylic resin; treatment with a metal oxide; and so forth. Treatment with a plurality of these treatments is preferred. For example, the surface of a finely divided titanium oxide may be coated with a metal oxide such as silicon oxide or alumina followed by treatment of the surface with an alkylsilane. The amount of surface treatment is preferably in the range from 0.1 to 50 mass % as the total with reference to the powder.

The organic ultraviolet protective component is a lipophilic ultraviolet protective component, for example, benzoic acid-type ultraviolet absorbers such as para-aminobenzoic acid (PABA), the monoglycerol ester of PABA, the ethyl ester of N,N-dipropoxyPABA, the ethyl ester of N,N-diethoxyPABA, the ethyl ester of N,N-dimethylPABA, the butyl ester of N,N-dimethylPABA, the hexyl ester of 2-[4-(diethylamino)-2-hydroxybenzoyl]benzoate (trade name: Uvinul A Plus), and so forth; anthranilic acid-type ultraviolet absorbers such as homomenthyl N-acetylanthranilate and so forth; salicylic acid-type ultraviolet absorbers such as amyl salicylate, menthyl salicylate, homomenthyl salicylate, octyl salicylate, phenyl salicylate, benzyl salicylate, p-isopropanolphenyl salicylate, and so forth; cinnamic acid-type ultraviolet absorbers such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, mono-2-ethylhexanoylglyceryl di-p- methoxycinnamate, 3-methyl-4-[methylbis(trimethylsiloxy) silyl]butyl 3,4,5-trimethoxycinnamate, dimethicodiethylbenzalmalonate (trade name: Parsol SLX (INCI name: Polysilicone-15)), and so forth; benzophenone-type ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, the salt of 2-hydroxy-4-methoxybenzophenone-5-sulfonic acid, 4-phenylbenzophenone, 2-ethylhexyl 4'-phenylbenzophenone-2-carboxylate, hydroxy-4-n-octoxybenzophenone, 4-hydroxy-3-carboxybenzophenone, and so forth; as well as 3-(4'-methylbenzylidene)-d,l-camphor, 3-benzylidene-d,l-camphor, urocanic acid, ethyl urocanate, 2-phenyl-5-methyl-benzoxazole, 2,2'-hydroxy-5-methylphenylbenzotriazole, 2-(2'-hydroxy-5'-t-octylphenyl)benzotriazole, 2-(2'-hydroxy-5'-methylphenyl)benzotriazole, dibenzaladine, dianisoylmethane, 4-methoxy-4'-t-butyldibenzoylmethane, and 5-(3,3-dimethyl-2-norbornylidene)-3-pentan-2-one; benzotriazole-type ultraviolet absorbers such as 2,2'-methylenebis(6-(2H-benzotriazol-2-yl)-4-(1,1,3,3-teteramethylbutyl)phenyl (trade name: Tinosorb M (registered trademark)); triazine-type ultraviolet absorbers such as 2,4,6-tris[4-(2-ethylhexyloxycarbonyl)anilino]-1,3,5-triazine (INCI: Octyltriazone), 2,4-bis{[4-(2-ethylhexyloxy)-2-hydroxy]phenyl}-6-(4-methoxyphenyl)-1,3,5-triazine (INCI: bis-ethylhexyloxyphenol methoxyphenyl triazine, trade name: Tinosorb S (registered trademark)), and so forth; and 2-ethylhexyl 2-cyano-3,3-diphenylpropan-2-enoate (INCI: Octocrylene).

The previously described organic ultraviolet protective component may also be used contained in a hydrophobic polymer powder. The polymer powder may or may not be hollow; the average primary particle size is preferably in the range from 0.1 to 50 μm; and the particle size distribution may be broad or sharp. The type of polymer can be exemplified by acrylic resins, methacrylic resins, styrenic resins, polyurethane resins, polyethylenes, polypropylenes, polyethylene terephthalates, silicone resins, nylons, acrylamide resins, and silylated polypeptide resins. A polymer powder containing the organic ultraviolet protective component in the range from 0.1 to 30 mass % is preferred, and a polymer powder containing the UV-A absorber 4-tert-butyl-4'-methoxydibenzoylmethane is particularly preferred.

An ultraviolet protective component that can be favorably used in the cosmetic of the present invention is at least one selection from the group consisting of finely divided titanium oxide, finely divided zinc oxide, 2-ethylhexyl para-methoxycinnamate, 4-tert-butyl-4'-methoxydibenzoylmethane, benzotriazole-type ultraviolet absorbers, and triazine-type ultraviolet absorbers. These ultraviolet protective components are favorable for use because they are general purpose, are easily acquired, and have a high ultraviolet protective effect. The co-use of an inorganic ultraviolet protective component with an organic ultraviolet protective component is preferred, while the co-use of an ultraviolet protective component against UV-A with an ultraviolet protective component against UV-B is even more preferred.

The use of an ultraviolet protective component in combination with the higher alcohol-modified silicone (A) in the cosmetic of the present invention makes it possible, while maintaining the unique suede-like tactile feel thereof, to stably disperse the ultraviolet protective component in the cosmetic and impart an excellent ultraviolet protective function to the cosmetic. The previously described ultraviolet protective component is particularly preferably incorporated in the cosmetic of the present invention in the range from 0.1 to 40.0 mass % in total with respect to the cosmetic as a whole, while the range of 0.5 to 15.0 mass % in total with respect to the cosmetic as a whole is more preferred.

In addition to the higher alcohol-modified silicone (A), at least one selection from the group consisting of acrylic silicone dendrimer copolymers, polyamide-modified silicones, alkyl-modified silicone waxes, and alkyl-modified silicone resin waxes can be used in the cosmetic of the present invention.

The acrylic silicone dendrimer copolymer is a vinyl polymer that has a carbosiloxane dendrimer structure in side chain position, and the vinyl polymer described in JP 4,009,382 B (JP 2000-063225 A) is a particularly preferred example. Examples of commercially available products are FA 4001 CM Silicone Acrylate and FA 4002 ID Silicone Acrylate, both from Dow Corning Toray Co., Ltd., and this may also be an acrylic silicone dendrimer copolymer that has a $C_{8-30}$ and preferably a $C_{14-22}$ long-chain alkyl group in, for example, side chain position. This acrylic silicone dendrimer copolymer exercises an excellent film-forming performance when incorporated by itself, and its incorporation in a cosmetic according to the present invention therefore makes possible the formation of a strong cosmetic film on the coated region and substantially improves the cosmetic durability, e.g., the resistance to sebum, resistance to abrasion, and so forth.

Through the combined use, on the other hand, of the higher alcohol-modified silicone (A) with an acrylic silicone dendrimer copolymer, the surface protective characteristics, such as the resistance to sebum and so forth, are improved due to the strong water repellency provided by the carbosiloxane dendrimer structure, and, in combination with this, the advantages accrue upon application of the generation of a lustrous perception and the suede-like tactile feel characteristic of the higher alcohol-modified silicone and the effective masking of elevations and depressions, e.g., wrinkles, pores, and so forth, in the coated skin. In particular, since the higher alcohol-modified silicone (A) according to the present invention brings about a favorable compatibility between the acrylic silicone dendrimer copolymer and powders, colorants, and other oils, the advantages accrue of an inhibition of the disarrangement or unwanted removal of the cosmetic on the skin and of supporting a long-term persistence of the suede-like tactile feel. Moreover, the treatment of a powder or colorant using a known method and the combination of the higher alcohol-modified silicone (A) and acrylic silicone dendrimer copolymer makes possible the preparation of a cosmetic powder composition that exhibits an excellent blend stability.

The quantity of incorporation of the acrylic silicone dendrimer copolymer is selected as appropriate in conformity with the objective and intent of incorporation therefor, but is preferably in the range from 1 to 99 mass % of the cosmetic as a whole and particularly preferably is in the range from 30 to 70 mass %.

The polyamide-modified silicone can be exemplified by the siloxane-based polyamide compound described in U.S. Pat. No. 5,981,680 (JP 2000-038450 A) and JP 2001-512164 A. Examples of commercially available products are 2-8178 Gellant and 2-8179 Gellant from the Dow Corning Corporation (US). Like the previously described oil-soluble gellant, the polyamide-modified silicone is useful as a thickener/gellant for oily ingredients and particularly for silicone oils.

The co-use of the polyamide-modified silicone with the higher alcohol-modified silicone provides additional improvements in the affinity for oils such as silicone oils, and as a consequence the cosmetic according to the present invention, when coated on the skin or hair, will exhibit good subsidence when spread and an excellent sensation stability and an excellent adherence. In addition, while maintaining the suede-like tactile feel, the advantages also accrue from a quality standpoint of obtaining an excellent lustrous transparent presentation and an excellent gloss, of making possible appropriate adjustments to the viscosity and hardness (softness) of the oil ingredient-containing cosmetic as a whole, and of inhibiting the oiliness, i.e., the oily sticky tactile feel, as a whole. In addition, the dispersion stability of, for example, a fragrance, powder, and so forth, is improved by the use of the higher alcohol-modified silicone, and as a consequence a uniform and silky smooth cosmetic feel will characteristically persist long term.

The quantity of incorporation of the polyamide-modified silicone is selected as appropriate in conformity with the objective and intent of incorporation therefor, but in the case of use as a gellant for oily ingredients is in the range from 0.5 to 80 mass parts and more preferably in the range from 1 to 50 mass parts, in each case per 100 mass parts of the oily component, e.g., oils and so forth.

The alkyl-modified silicone wax is a component useful as a portion of the base of an oil-based solid cosmetic, and alkyl-modified silicones that are waxes at room temperature can be used without particular limitation in the cosmetic of the present invention. This alkyl-modified silicone wax can be exemplified by methyl(long-chain alkyl)polysiloxanes endblocked by trimethylsiloxy at both molecular chain terminals, dimethylpolysiloxane-methyl(long-chain alkyl)siloxane copolymers endblocked by trimethylsiloxy at both molecular chain terminals, and dimethylpolysiloxanes modified by long-chain alkyl at both molecular chain terminals. Examples of commercially available products are AMS-C30 Cosmetic Wax and 2503 Cosmetic Wax from the Dow Corning Corporation (US).

The higher alcohol-modified silicone according to the present invention contains a divalent hydrocarbyl group, e.g., a long-chain alkylene group, which results in an excellent affinity with alkyl-modified silicone waxes and makes possible the formation of a uniform oil phase. In addition, through co-use with the higher alcohol-modified silicone according to the present invention, the affinity with oily ingredients is improved and a cosmetic can be obtained that exhibits an excellent moldability and, due to an excellent uniformity of dispersion by the individual components, an excellent long-term storage stability. In particular, in the case of a system that contains a powder or colorant, the advantage accrues from a quality standpoint that a system containing the alkyl-modified silicone wax will resist separation; also, an oil-based cosmetic can be obtained that exhibits an excellent shape-retention performance and that when applied spreads smoothly and uniformly.

The alkyl-modified silicone wax used in the present invention preferably has a melting point of at least 60° C. from the standpoints of the cosmetic durability and high-temperature stability. Its quantity of incorporation is selected as appropriate in conformity with the objective and intent of incorporation therefor, and it can generally be incorporated in the range from 1 to 50 mass % with respect to the cosmetic as a whole. Incorporation in the range from 5 to 40 mass % is preferred in order to achieve improvements in the moldability and cosmetic durability for oil-based cosmetics. In addition, since the alkyl-modified silicone wax under consideration has a high affinity with crosslinked organopolysiloxanes and long-chain alkyl-containing silicone oils, such as the previously described alkyl-modified silicones and the like, it is preferably also used in combination with these optional components.

The alkyl-modified silicone resin wax is a component that provides a cosmetic with resistance to sebum, a moisturizing behavior, and a silky smooth tactile feel, and a preferred example is the silsesquioxane resin wax described in JP 2007-532754 A. Commercial products here can be exemplified by SW-8005 C30 RESIN WAX from the Dow Corning Corporation (US).

The higher alcohol-modified silicone according to the present invention contains a divalent hydrocarbyl group, e.g., a long-chain alkylene group, which results in an excellent affinity with alkyl-modified silicone resin waxes, just as with the alkyl-modified silicone waxes, and makes possible the formation of a uniform oil phase. In addition, an oil phase that contains this alkyl-modified silicone resin wax can be stably emulsified with other surfactants, improving the conditioning effect for the skin and hair and providing a silky smooth and moist tactile feel. Another advantage is that the suede-like tactile feel of the higher alcohol-modified silicone is not impaired.

The quantity of incorporation of the alkyl-modified silicone resin wax in the present invention is selected as appropriate in conformity with the objective and intent of incorporation therefor, but from 0.5 to 50 mass % with respect to the cosmetic as a whole can generally be incorporated. The range of 1 to 30 mass % is particularly preferred in order to realize sebum resistance and a silky smooth tactile feel for a cosmetic.

Other components as used in ordinary cosmetics and topical skin preparations may be added to the cosmetic and topical skin preparation of the present invention within a range that does not impair the effects of the present invention. These other components can be exemplified by alcohols, organic resins, humectants, thickeners, preservatives, antibacterials, fragrances, salts, antioxidants, pH adjusters, chelating agents, algefacients, antiinflammatories, physiologically active components (whiteners, cell activators, agents for ameliorating skin roughness, circulation promoters, skin astringents, antiseborrheics, and so forth), vitamins, amino acids, nucleic acids, hormones, inclusion compounds, and so forth. There is no particular limitation to the preceding.

One or more polyhydric alcohols and/or lower monohydric alcohols can be used as the alcohol. The lower alcohols can be exemplified by ethanol, isopropanol, n-propanol, t-butanol, s-butanol, and so forth. The polyhydric alcohols can be exemplified by dihydric alcohols such as 1,3-propanediol, 1,3-butylene glycol, 1,2-butylene glycol, propylene glycol, trimethylene glycol, tetramethylene glycol, 2,3-butylene glycol, pentamethylene glycol, 2-buten-1,4-diol, dibutylene glycol, pentyl glycol, hexylene glycol, octylene glycol, and so forth; trihydric alcohols such as glycerol, trimethylolpropane, 1,2, 6-hexanetriol, and so forth; tetrahydric and higher hydric polyhydric alcohols such as pentaerythritol, xylitol, and so forth; and sugar alcohols such as sorbitol, mannitol, maltitol, maltotriose, sucrose, erythritol, glucose, fructose, degraded starch, maltose, xylitose, reducing alcohols provided by starch degradation, and so forth. Polyhydric alcohol polymers are another example in addition to the previously cited low molecular weight polyhydric alcohols, and these polyhydric alcohol polymers can be exemplified by diethylene glycol, dipropylene glycol, triethylene glycol, polypropylene glycol, tetraethylene glycol, diglycerol, polyethylene glycol, triglycerol, tetraglycerol, polyglycerol, and so forth. Particularly preferred among the preceding are 1,3-propanediol, 1,3-butylene glycol, sorbitol, dipropylene glycol, glycerol, and polyethylene glycol. The quantity of incorporation is suitably in the range from 0.1 to 50 mass % of the cosmetic as a whole. These polyhydric alcohols can be incorporated at from approximately 5 to 30 mass % with the goal of improving the storage stability of the cosmetic, and this is a preferred embodiment of the present invention.

For the cosmetic of the present invention, a uniformly solubilized emulsion premix can be formed by mixing the higher alcohol-modified silicone (A) to uniformity in an alcohol as described above, e.g., ethanol, together with another surfactant and an oil. This provides the following advantage: this emulsion premix can then be mixed with water to form a uniform oil-in-water emulsion-type cosmetic. Furthermore, the higher alcohol-modified silicone (A) according to the present invention, because it has an alcoholic hydroxyl group, can improve the storage stability of the aforementioned solubilized product, while the obtained oil-in-water emulsion-type cosmetic accrues the advantages from a quality standpoint of an excellent timewise stability and an excellent blend stability with other water-soluble components.

The organic resin can be exemplified by polyvinyl alcohol, polyvinylpyrrolidone, and alkyl polyacrylate copolymers. Due to its excellent film-forming behavior, this component, through its incorporation in the cosmetic according to the present invention, makes possible the formation of a strong cosmetic film on the coated region, resulting in an improved cosmetic persistence, e.g., resistance to sebum, resistance to abrasion, and so forth.

The humectant can be exemplified by hyaluronic acid, chondroitin sulfate, salts of pyrrolidonecarboxylic acid, polyoxyethylene methyl glucoside, polyoxypropylene methyl glucoside, and so forth. Of course, the previously described polyhydric alcohols exhibit humectancy on the skin and hair. The advantage for the cosmetic of the present invention is that these humectant components can be stably taken into the gel structure comprising the higher alcohol-modified silicone/higher alcohol/water/surfactant. Moreover, the moisturizing characteristics of these humectants can be improved by co-use with another good moisturizing oily ingredient, or by the selection of the formulation of the cosmetic gel, or by co-use with a film-forming component.

The preservative can be exemplified by alkyl para-hydroxybenzoate esters, benzoic acid, sodium benzoate, sorbic acid, potassium sorbate, phenoxyethanol, and so forth, while antibacterials can be exemplified by benzoic acid, salicylic acid, carbolic acid, sorbic acid, alkyl para-hydroxybenzoate esters, p-chloro-m-cresol, hexachlorophene, benzalkonium chloride, chlorhexidine chloride, trichlorocarbanilide, triclosan, photosensitive ingredients, isothiazolinone compounds such as 2-methyl-4-isothiazolin-3-one and 5-chloro-2-methyl-4-isothiazolin-3-one, and amine oxides such as dimethyllaurylamine oxide and dihydroxyethyllaurylamine oxide.

Other antibacterial preservative components in addition to the preceding are apolactoferrin; phenolic compounds such as resorcinol; antibacterial or antiseptic basic proteins and peptides such as iturin-type peptides, surfactin-type peptides, and protamine and its salts such as protamine sulfate; polyysines such as $\epsilon$-polylysine and its salts; antibacterial metal compounds that are metal compounds capable of producing, for example, the silver ion, copper ion, and so forth; and antibacterial enzymes such as proteases, lipases, oxidoreductases, carbohydrases, transferases, phytases, and so forth.

The fragrance can be exemplified by fragrances extracted from, inter alia, the flower, seed, leaf, and root of plants; fragrances extracted from seaweed; fragrances extracted from various animal parts and secretions, e.g., musk and incense; and artificially synthesized fragrances, e.g., menthol, musk, acetate esters, and vanilla. The fragrance is incorporated in order to impart fragrance or aroma to the cosmetic or to mask an unpleasant odor. A known fragrance can be selected as appropriate and can be incorporated in a suitable quantity in conformity with the cosmetic formulation. The higher alcohol-modified silicone (A) according to the present invention also exhibits an excellent fragrance retention.

The higher alcohol-modified silicone (A) in the cosmetic and topical skin preparation of the present invention is substantially odorless and thus does not impair the scent of the fragrance, and the combination with the higher alcohol-modified silicone that has been deodorized by a hydrogenation reaction is particularly suitably used. The incorporation of the higher alcohol-modified silicone in combination with a fragrance has the advantage of improving the persistence of the added fragrance for both oil-based and water-based cosmetics. More favorably, the persistence of the fragrance is substantially improved in a formulation in which the fragrance component is incorporated in a water-based gel structure composed of the higher alcohol-modified silicone/higher alcohol/water/surfactant or in an oil-based gel structure obtained by the combination with an oily gellant such as an amide-modified silicone.

The antioxidant can be exemplified by tocopherol, butylhydroxyanisole, dibutylhydroxytoluene, phytic acid, and so forth.

The pH adjuster can be exemplified by lactic acid, citric acid, glycolic acid, succinic acid, tartaric acid, dl-malic acid, potassium carbonate, sodium bicarbonate, ammonium bicarbonate, and so forth.

The chelating agent can be exemplified by alanine, sodium edetate, sodium polyphosphate, sodium meta-phosphate, phosphoric acid, and so forth.

The algefacient can be exemplified by 1-menthol, camphor, and so forth.

The physiologically active component can be exemplified by vitamins; amino acids; nucleic acids; hormones; natural plant extract components; seaweed extract components; herbal medicine components; whiteners such as placental extract, arbutin, glutathione, *Saxifraga sarmentosa* extract, and so forth; cell activators such as royal jelly; agents for ameliorating skin roughness; circulation promoters such as nonylic acid valenylamide, benzyl nicotinate, $\beta$-butoxyethyl nicotinate, capsaicin, zingerone, Cantharides tincture, ichthammol, caffeine, tannic acid, $\alpha$-borneol, tocopherol nicotinate, inositol hexanicotinate, cyclandelate, cinnarizine, tolazoline, acetylcholine, verapamil, cepharanthine, $\gamma$-oryzanol, and so forth; skin astringents such as zinc oxide, tannic acid, and so forth; antiseborrheics such as sulfur, thianthrol, and so forth; and antiinflammatories such as $\epsilon$-aminocaproic acid, glycyrrhizic acid, $\beta$-glycyrrhetinic acid, lysozyme chloride, guaiazulene, hydrocortisone, allantoin, tranexamic acid, azulene, and so forth.

The vitamins can be exemplified by vitamin A species such as vitamin A oil, retinol, retinol acetate, and retinol palmitate; vitamin B species such as vitamin B2 species such as riboflavin, riboflavin butyrate, and flavin adenine nucleotide, vitamin B6 species such as pyridoxine hydrochloride, pyridoxine dioctanoate, and pyridoxine tripalmitate, vitamin B12 and derivatives thereof, and vitamin B15 and derivatives thereof; vitamin C species such as L-ascorbic acid, L-ascorbic acid dipalmitic acid ester, sodium L-ascorbic acid-2-sulfate, and dipotassium L-ascorbic acid phosphoric acid diester; vitamin D species such as ergocalciferol and cholecalciferol; vitamin E species such as $\alpha$-tocopherol, $\beta$-tocopherol, $\gamma$-tocopherol, dl-$\alpha$-tocopherol acetate, dl-$\alpha$-tocopherol nicotinate, and dl- α-tocopherol succinate; vitamin H; nicotinic acids such as vitamin P, nicotinic acid, and benzyl nicotinate; and pantothenic acids such as calcium pantothenate, D-pantothenyl alcohol, pantothenyl ethyl ether, and acetylpantothenyl ethyl ether.

The amino acid can be exemplified by glycine, valine, leucine, isoleucine, serine, threonine, phenylalanine, arginine, lysine, aspartic acid, glutamic acid, cystine, cysteine, methionine, and tryptophan.

The nucleic acid can be exemplified by deoxyribonucleic acid and so forth.

The hormone can be exemplified by estradiol, ethenylestradiol, and so forth.

Examples of the natural plant extract component, seaweed extract component, and herbal medicine component are provided below. The selection and incorporation of at least one of these components having an effect such as a whitening action, anti-aging action, aging reversing action, skin beautifying action, antibacterial action, preservative action, and so forth, is particularly preferred.

Specific components can be exemplified by *Angelica keiskei* extract, avocado extract, *Hydrangea serrata* extract, althea extract, arnica extract, aloe extract, apricot extract, apricot kernel extract, *Gingko biloba* extract, fennel fruit extract, turmeric root extract, oolong tea extract, *Rosa multiflora* extract, *Echinacea angustifolia* leaf extract, *Scutellaria baicalensis* root extract, *Phellodendron amurense* extract, *coptis* rhizome extract, *Hordeum vulgare* seed extract, *Hypericum perforatum* extract, *Lamium album* extract, *Nasturtium officinale* extract, orange extract, dried sea water, seaweed extract, hydrolyzed elastin, hydrolyzed wheat flour, hydrolyzed silk, chamomile extract, carrot extract, *Artemisia capillaris* flower extract, licorice extract, karkade extract, *Pyracantha fortuneana* extract, kiwi extract, cinchona extract, cucumber extract, guanosine, *Gardenia florida* extract, *Sasa veitchii* extract, *Sophora angustifolia* extract, walnut extract, grapefruit extract, *Clematis vitalba* leaf extract, chlorella extract, *Morus alba* root extract, *Gentiana lutea* extract, black tea extract, yeast extract, burdock extract, fermented rice bran extract, rice germ oil, comfrey extract, collagen, *Vaccinum vitis idaea* extract, *asiasarum* root extract, *Bupleurum falcatum* extract, umbilical extract, *Salvia* extract, soapwort extract, *sasa* bamboo grass extract, *Crataegus cantata* fruit extract, *Zanthoxylum piperitum* extract, shiitake extract, *rehmannia* root extract, *Lithospermum erythrorhizone* root extract, *Perilla ocymoides* extract, *Talia cordata* flower extract, Spire ulmaria extract, Peoria albiflora extract, *Acores calamus* root extract, *Betula alba* extract, *Equisetum arvense* extract, *Hedera helix* extract, *Crataegus oxyacantha* extract, Sawbucks nigra extract, *Achillea millefolium* extract, Mentha pipe Rita leaf extract, sage extract, *Malva sylvestris* extract, *Cnidium officinale* root extract, *Swertia japonica* extract, soybean extract, *Zizyphus jujube* fruit extract, thyme extract, tea extract, *Eugenia caryophyllus* flower extract, *Imperata cylindrica* extract, *Citrus unshiu* Marc extract, *angelica* root extract, *Calendula officinalis* extract, Prunes persica stone extract, *Citrus aurantium* peel extract, *Houttuynia cordata* extract, tomato extract, natto extract, carrot extract, garlic extract, Rosa canine fruit extract, hibiscus extract, *Ophiopogon* extract, *Nelumbo nucifera* extract, parsley extract, honey, witch hazel extract, *Parietaria officinalis* extract, *Isodon trichocarpus* extract, bisabolol, *Eriobotrya japonica* extract, coltsfoot flower extract, *Petasites japonicus* extract, Peoria cocos extract, butcher's broom extract, grape extract, propolis, *Luffa cylindrica* fruit extract, safflower flower extract, peppermint extract, Tillie miquellana extract, Peoria suffruticosa root extract, hops extract, *Pinus sylvestris* cone extract, horse chestnut extract, Japanese skunk cabbage extract, Sap Indus mukurossi peel extract, *Melissa* extract, peach extract, Centaurea cyan's flower extract, *Eucalyptus* extract, *Saxifraga sarmentosa* extract, *Citrus juncos* extract, coix seed extract, *Artemisia princes* extract, lavender extract, apple extract, lettuce extract, lemon extract, *Astragals sinicus* extract, rose extract, rosemary extract, Roman chamomile extract, and royal jelly extract. These may be water soluble or oil soluble.

The cosmetic and topical skin preparation of the present invention may also contain, in conformity with the formulation and purpose thereof, for example, water such as purified water, mineral water, and so forth, as well as a solvent such as light isoparaffin, an ether, LPG, N-methylpyrrolidone, hydrofluorocarbons, and so forth.

The cosmetic and topical skin preparation of the present invention may also take any of the following forms: liquid, emulsion, cream, solid, paste, gel, powder, multilayer configuration, mousse, spray, and sheet form.

The cosmetic of the present invention can be exemplified by ultraviolet protective products such as sunscreens and so forth; skin care products such as facial lotions, milky lotions, creams, cleansing cosmetics, massage products, cleansers, and so forth; make-up products such as foundations, make-up bases, rouges, eye shadows, mascaras, eyeliners, lipsticks, and so forth; hair products such as shampoos, rinses, treatments, and so forth; antiperspirants; and deodorants. Accordingly, these products can be selected from various forms, such as liquids, emulsions, solids, pastes, gels, sprays, and so forth.

Similarly, the topical skin preparation of the present invention can be exemplified by ointments, hair-restoring agents, hair-growth agents, analgesics, antiseptics, antiinflammatories, algefacients, and skin ageing inhibitors, but is not limited to the preceding. In addition, these products can be selected from various configurations, e.g., liquids, emulsions, solids, pastes, gels, sprays, and so forth.

Because the mixture of the previously described higher alcohol-modified silicone (A) with a hydrophilic medium achieves a uniform dispersion of the individual components in the case of the cosmetic and topical skin preparation of the present invention, the cosmetic and topical skin preparation of the present invention are well suited in particular for use as a water-containing cosmetic or a water-containing topical skin preparation, and the configuration of a water-containing gel or an emulsion such as an oil-in-water emulsion is suitably selected. Here, the composition, particle size, and so forth, of suitable gel structures, suitable water-containing cosmetics such as emulsion cosmetics, and suitable water-containing topical skin preparations are as described above.

Using the previously described higher alcohol-modified silicone (A) or a gel containing same as an ingredient of the cosmetic, the aforementioned water-containing cosmetic and so forth can be produced by mixing with water using mechanical force and using a device such as, for example, a homomixer, paddle mixer, Henschel mixer, Homo Disper, colloid mill, propeller stirrer, homogenizer, inline continuous emulsifier, ultrasound emulsifier, or vacuum kneader. In addition, in other methods of producing these water-containing cosmetics, the quantity of use and the proportion of incorporation for the water (C) are not limited and are preferably suitably selected in the range from 1 to 99 mass % of the cosmetic as a whole.

Otherwise, the cosmetic and topical skin preparation of the present invention can be produced in accordance with the configuration of the desired product; however, because the higher alcohol-modified silicone (A) has an excellent affinity with various oils and in particular with the higher alcohol (B), the cosmetic and topical skin preparation of the present invention are also favorably obtained by a production step in which a system comprising these components and other cosmetic ingredients is mixed and heated. The execution of this step of heating a mixture of these cosmetic ingredients has the advantage of improving the uniformity, stability, and use sensation of the obtained cosmetic and topical skin preparation.

More specifically, a preferred method of producing the previously described cosmetic and topical skin preparation contains a step in which a system prepared by blending 100 mass parts of at least one higher alcohol-modified silicone (A) with general formula (1) and 10 to 1,000 mass parts of at least one $C_{10-30}$ higher alcohol (B) is heated to 50° C. to 150° C. In addition to these components, this system may incorporate other cosmetic ingredients as appropriate. Moreover, this production method may be a step in which a mixture containing the higher alcohol-modified silicone (A) and a mixture containing the higher alcohol (B) are separately mixed to uniformity and the two are then mixed and the resulting system is heated. It is preferred in this cosmetic production method that mixing be carried out using mechanical force while the system as a whole is heated. This heating can be performed by heating the system as a whole using a known method, for example, a heater, hot water line, steam line, and so forth. In addition, the whole system can also be heated by the latent heat accompanying stirring due to the continuous application to the whole system of a strong shear force using, for example, a power mixer. The heating temperature will vary with the ingredients, composition, and type of cosmetic, but heating in the range from 50° C. to 150° C. is preferred and the range from 50° C. to 120° C. is particularly preferred because this enables uniform mixing even for ingredients that are highly viscous to semisolid at room temperature (25° C.).

The topical skin preparation of the present invention can also be prepared by a production method other than the preceding without particular limitation. In this case, for example, considering a pharmacopeial topical skin preparation that is a formulation containing an oil such as a higher alcohol such as stearyl alcohol and/or a hydrocarbon oil such as petrolatum, a topical skin preparation of the present invention can be produced by blending using the higher alcohol-modified silicone (A) for all or a portion of this oil. In particular, since the higher alcohol-modified silicone (A) according to the present invention exhibits an excellent compatibility with higher alcohols and the like, just incorporation by mixing with these oils may be sufficient for the formulation design. Similarly, the advantages accrue of a high timewise stability for the obtained topical skin preparation and a high degree of freedom for incorporation in the topical skin preparation.

Because the incorporation of the higher alcohol-modified silicone (A), in addition to providing a strong improvement in the tactile feel, also has a pronounced ability to impart gloss to the applied film, the cosmetic and topical skin preparation of the present invention can also be very suitably used for lipsticks, lip glosses, and hair products. Because the higher alcohol-modified silicone used in the cosmetic of the present invention functions as a surfactant or co-surfactant, diffusion to the corneum of the skin is excellent and there is a high potential for the percutaneous absorptivity seen with known nonionic surfactants. This higher alcohol-modified silicone is therefore also effective for use as an ointment, drug, or topical skin preparation that contains a physiologically active component such as a whitening agent or ageing inhibitor. In addition, the higher alcohol-modified silicone (A) characteristically has a very high affinity with various oils and also has a strong function as a cleansing or washing substance. In the case of products such as lotions, creams, emulsions, and sheets, the cosmetic removal behavior is excellent and a film with a good tactile feel remains on the skin, and due to this a product is characteristically obtained that also has an excellent skin tactile feel post-cleansing.

EXAMPLES

The present invention is more particularly illustrated by the examples and comparative examples provided below, but the present invention is not limited to the examples. Below, the indication of "%" by itself denotes mass % and the indication of "parts" by itself denotes mass parts. The structures of the organopolysiloxanes were identified by assignment of the peaks measured by $^{13}$C-nuclear magnetic resonance analysis ($^{13}$C-NMR below) and $^{29}$Si-nuclear magnetic resonance analysis ($^{29}$Si-NMR below). SiH % is used to indicate the content, in mass %, of the silicon-bonded hydrogen per organohydrogenpolysiloxane molecule.

The higher alcohol-modified silicones in Table 1 below were first synthesized according to Synthesis Examples 1 to 10, also below. Silicone No. 9 was used in the comparative experimental examples and comparative examples for the present invention. The following conventions are used in the compositional formulas to describe organopolysiloxane structure: the trimethylsiloxy unit (($CH_3$)$_3$SiO—) is indicated by "M"; the dimethylhydrogensiloxy unit (H($CH_3$)$_2$SiO—) is indicated by "$M^H$"; the dimethylhydroxysiloxy unit (HO($CH_3$)$_2$SiO—) is indicated by "$M^{OH}$"; the dimethylsiloxy unit (—($CH_3$)$_2$SiO—) is indicated by "D"; the methylhydrogensiloxy unit (—H($CH_3$)SiO—) is indicated by "$D^H$"; and units provided by changing one of the methyl groups in M and D to a particular substituent —R* other than hydrogen are indicated by "$M^{R*}$" and "$D^{R*}$". The structures of the functional groups in Table 1 are given below.

$R^{*1}$=—$C_{11}H_{22}$—OH $R^{*2}$=—$C_{12}H_{25}$ $R^{*3}$=—$C_2H_4$—Si{OSi($CH_3$)$_3$}$_3$ $R^{*4}$=—$C_{22}H_{44}$—OH

Table 1 also reports the relationship with the disiloxane unit subscripts in general formula (1).

TABLE 1

| higher alcohol-modified silicone | average compositional formula | relationship to general formula (1) |
|---|---|---|
| No. 1 (trisiloxane type) | $MD^{R*1}M$ | m1 = m3 = 0, m2 = 1 |
| No. 2 (modification at both terminals) | $M^{R*1}D_{14}M^{R*1}$ | m1 = 0, m2 = 0, m3 = 14 |

TABLE 1-continued

| higher alcohol-modified silicone | average compositional formula | relationship to general formula (1) |
|---|---|---|
| No. 3 (side chain modification) | $MD_{19}D^{R*1}{}_2M$ | m1 = 0, m2 = 2, m3 = 19 |
| No. 4 (modification at both terminals and side chain modification) | $M^{R*1}D_{19}D^{R*1}{}_3M^{R*1}$ | m1 = 0, m2 = 3, m3 = 19 |
| No. 5 (side chain co-modification by C12 alkyl and dendrimer) | $MD_{14}D^{R*1}{}_1D^{R*2}{}_1D^{R*3}{}_3M$ | m1 = 4, m2 = 1, m3 = 14 |
| No. 6 (side chain co-modification by C12 alkyl) | $MD_{14}D^{R*1}{}_1D^{R*2}{}_4M$ | m1 = 4, m2 = 1, m3 = 14 |
| No. 7 (side chain co-modification by dendrimer) | $MD_{14}D^{R*1}{}_2D^{R*3}{}_3M$ | m1 = 3, m2 = 2, m3 = 14 |
| No. 8 (no. of D units = 55) | $MD_{35}D^{R*1}{}_{20}M$ | m1 = 0, m2 = 20, m3 = 35 |
| No. 9 (no. of D units = 60) *comparative compound | $M^{R*1}D_{60}M^{R*1}$ | m1 = m2 = 0, m3 = 60 |
| No. 10 (C22 higher alcohol modifying group, modification at both terminals) | $M^{R4}D_{14}M^{R4}$ | m1 = 0, m2 = 0, m3 = 14 |

Synthesis Example 1

Higher Alcohol-Modified Silicone No. 1

89.0 g undecenyl alcohol was introduced into a reactor fitted with a stirrer, thermometer, reflux condenser, and dropping funnel and was heated to 70° C. while stirring under a nitrogen current. 27 mg of a platinum catalyst was added followed by the gradual addition from the dropping funnel of 127.8 g of a methylhydrogentrisiloxane with the average compositional formula $MD^HM$ to start the reaction. After the completion of addition, ageing was carried out for 1 hour and the completion of the reaction was confirmed by gas chromatography. Under reduced pressure, the unreacted siloxane was removed at 70° C. followed by heating to 150° C. and removal of the internally converted and excess undecenyl alcohol to obtain higher alcohol-modified silicone No. 1. The yield was 168.1 g or 82%. The product had a refractive index of 1.431 and a kinematic viscosity of 38.0 mm²/s and was a light yellow transparent liquid.

Synthesis Example 2

Higher Alcohol-Modified Silicone No. 2

50.0 g undecenyl alcohol was introduced into a reactor fitted with a stirrer, thermometer, reflux condenser, and dropping funnel and was heated to 70° C. while stirring under a nitrogen current. 60 mg of a platinum catalyst was added followed by the gradual addition from the dropping funnel of 192.6 g of a methylhydrogenpolysiloxane with the average compositional formula $M^HD_{14}M^H$ (0.122 SiH %) to start the reaction. After the completion of addition, ageing was carried out for 4 hours. After confirmation of the development of the reaction by confirmation of the extinction of the Si—H from the IR spectrum, heating was carried out to 150° C. under reduced pressure and the internally converted and excess undecenyl alcohol was removed to obtain higher alcohol-modified silicone No. 2. The yield was 230.4 g or 73%. The product had a refractive index of 1.419 and a kinematic viscosity of 107.5 mm²/s and was a light brown transparent liquid.

Synthesis Example 3

Higher Alcohol-Modified Silicone No. 3

55.0 g undecenyl alcohol was introduced into a reactor fitted with a stirrer, thermometer, reflux condenser, and dropping funnel and was heated to 70° C. while stirring under a nitrogen current. 124 mg of a platinum catalyst was added followed by the gradual addition from the dropping funnel of 199.2 g of a methylhydrogenpolysiloxane with the average compositional formula $MD_{19}D^H{}_2M$ (0.118 SiH %) to start the reaction. After the completion of addition, ageing was carried out for 5 hours. After confirmation of the development of the reaction by confirmation of the extinction of the silicon-bonded hydrogen atom (indicated by "Si—H" below) from the IR spectrum, heating was carried out to 150° C. under reduced pressure and the internally converted and excess undecenyl alcohol was removed to obtain higher alcohol-modified silicone No. 3. The yield was 207.9 g or 87%. The product had a refractive index of 1.421 and a kinematic viscosity of 123.7 mm²/s and was a light brown transparent liquid.

Synthesis Example 4

Higher Alcohol-Modified Silicone No. 4

50.0 g undecenyl alcohol was introduced into a reactor fitted with a stirrer, thermometer, reflux condenser, and dropping funnel and was heated to 70° C. while stirring under a nitrogen current. 66 mg of a platinum catalyst was added followed by the gradual addition from the dropping funnel of 81.0 g of a methylhydrogenpolysiloxane with the average compositional formula $M^HD_{19}D^H{}_3M^H$ (0.29 SiH %) to start the reaction. After the completion of addition, ageing was carried out for 5 hours. After confirmation of the development of the reaction by confirmation of the extinction of the Si—H from the IR spectrum, heating was carried out to 150° C. under reduced pressure and the internally converted and excess undecenyl alcohol was removed to obtain silicone compound No. 4. The yield was 97 g or 80%. The product had a refractive index of 1.420 and a kinematic viscosity of 145.4 mm$^2$/s and was a light brown transparent liquid.

Synthesis Example 5

Higher Alcohol-Modified Silicone No. 5

30 g of a methylhydrogenpolysiloxane with the average compositional formula $MD_{14}D^H{}_5M$ was introduced into a reactor fitted with a stirrer, thermometer, and reflux condenser and was heated to 70° C. 2.1 g undecenyl alcohol, 2.1 g 1-dodecene, 16.8 g vinyltristrimethylsiloxysilane, and 127 mg of a platinum catalyst were added dropwise at 70° C. while stirring under nitrogen. The reaction was continued at 100° C. after the completion of addition. After confirmation of the development of the reaction by confirmation of the extinction of the Si—H from the IR spectrum, the internally converted and excess undecenyl alcohol was removed under reduced pressure to obtain the target higher alcohol-modified silicone No. 5. The yield was 45 g or 88%. The product had a refractive index of 1.414 and a kinematic viscosity of 80.5 mm$^2$/s and was a colorless transparent liquid.

Synthesis Example 6

Higher Alcohol-Modified Silicone No. 6

30 g of a methylhydrogenpolysiloxane with the average compositional formula $MD_{14}D^H{}_5M$ was introduced into a reactor fitted with a stirrer, thermometer, and reflux condenser and was heated to 70° C. 2.1 g undecenyl alcohol, 10.9 g 1-dodecene, and 107 mg of a platinum catalyst were added dropwise at 70° C. while stirring under nitrogen. The reaction was continued at 100° C. after the completion of addition. After confirmation of the development of the reaction by confirmation of the extinction of the Si—H from the IR spectrum, the internally converted and excess undecenyl alcohol was removed under reduced pressure to obtain the target higher alcohol-modified silicone No. 6. The yield was 37.4 g or 87%. The product had a refractive index of 1.422 and a kinematic viscosity of 51.5 mm$^2$/s and was a colorless transparent liquid.

Synthesis Example 7

Higher Alcohol-Modified Silicone No. 7

30 g of a methylhydrogenpolysiloxane with the average compositional formula $MD_{14}D^H{}_5M$ was introduced into a reactor fitted with a stirrer, thermometer, and reflux condenser and was heated to 70° C. 4.2 g undecenyl alcohol, 16.8 g vinyltristrimethylsiloxysilane, and 127 mg of a platinum catalyst were added dropwise at 70° C. while stirring under nitrogen. The reaction was continued at 100° C. after the completion of addition. After confirmation of the development of the reaction by confirmation of the extinction of the Si—H from the IR spectrum, the internally converted and excess undecenyl alcohol and the vinyltristrimethylsiloxysilane were removed under reduced pressure to obtain higher alcohol-modified silicone No. 7. The yield was 43.9 g or 86%. The product had a refractive index of 1.415 and a kinematic viscosity of 117.0 mm$^2$/s and was a colorless transparent liquid.

Synthesis Example 8

Higher Alcohol-Modified Silicone No. 8

50 g of a methylhydrogenpolysiloxane with the average compositional formula $MD_{35}D^H{}_{20}M$ was introduced into a reactor fitted with a stirrer, thermometer, and reflux condenser and was heated to 70° C. 28.4 g undecenyl alcohol and 19.6 mg of a platinum catalyst were added dropwise at 70° C. while stirring under nitrogen. The reaction was continued at 100° C. after the completion of addition. After confirmation of the development of the reaction by confirmation of the extinction of the Si—H from the IR spectrum, the internally converted and excess undecenyl alcohol was removed under reduced pressure to obtain higher alcohol-modified silicone No. 8. The yield was 60.7 g or 80%. The product had a refractive index of 1.413 and a kinematic viscosity of 520 mm$^2$/s and was a colorless transparent liquid.

Synthesis Example 9

Higher Alcohol-Modified Silicone No. 9

50 g of a methylhydrogenpolysiloxane with the average compositional formula $MD_{60}M^H$ was introduced into a reactor fitted with a stirrer, thermometer, and reflux condenser and was heated to 70° C. 2.0 g undecenyl alcohol and 13.0 mg of a platinum catalyst were added dropwise at 70° C. while stirring under nitrogen. The reaction was continued at 100° C. after the completion of addition. After confirmation of the development of the reaction by confirmation of the extinction of the Si—H from the IR spectrum, the internally converted and excess undecenyl alcohol was removed under reduced pressure to obtain higher alcohol-modified silicone No. 9. The yield was 44.0 g or 85%. The product had a refractive index of 1.412 and a kinematic viscosity of 350 mm$^2$/s and was a colorless transparent liquid.

Synthesis Example 10

Higher Alcohol-Modified Silicone No. 10

Higher alcohol-modified silicone No. 10, which contained a $C_{22}$ higher alcohol modifying group, was obtained by proceeding as in the previously described Synthesis Example 2, but in this case using, in place of the 50.0 g undecenyl alcohol used as a starting material in Synthesis Example 2, 95.3 g of the carbon-carbon double bond-terminated higher alcohol $CH_2$=CH—$(CH_2)_{20}$—OH.

Each of the compounds from the synthesis examples and the comparative compound were subjected to an evaluation of various properties in the examples and test examples that follow. In order to ensure objectivity, the following criteria were used to evaluate the properties (evaluated items) that were evaluated by sensory testing in the following examples and test examples.

<Evaluation Criteria>

The use sensation for the particular evaluated item was evaluated by a 10-member panel using the composition to be evaluated. Using a questionnaire format to elicit a response from each panelist, a score of 5 was entered when the particular evaluated item was determined to be excellent; a score of 1 was entered when a determination of poor was made; and a score of 2, 3, or 4 was entered for intermediate determinations. The resulting average score was used as the result of the use sensation evaluation. When a hair cosmetic was being tested, the test was carried out after the components applied to the hair had first been thoroughly washed using a cleansing shampoo.

Examples

Hair Treatment Creams

Examples 1 to 4 and Comparative Examples 1 to 6

Hair cosmetics in the form of hair treatment creams were prepared using the compositions shown in Table 2 below and the following were evaluated: the suede-like tactile feel, hair luster, post-drying smoothness, suede-like tactile feel after the brushing test, moisturizing effect on the hair, and split end-preventing effect. With regard to the tactile feel after the brushing test, the tactile feel was evaluated after the cosmetic had been used and brushing had then been done 10 times. The split end-preventing effect was evaluated from the degree of split end production after the brushing test. The method of producing the cosmetic is provided below; component 6) is either the higher alcohol-modified silicone according to the present invention or its comparative compound.

<Method of Producing the Hair Treatment Cream>

Components 1) to 9) in Table 2 were heated and mixed and were gradually added with stirring to components 10) to 17), which had already been heated and dissolved to uniformity. The product was then obtained by filling into a container.

TABLE 2

| | component (unit: mass parts) | examples | | | | comparative examples | | | | | |
|---|---|---|---|---|---|---|---|---|---|---|---|
| | | 1 | 2 | 3 | 4 | 1 | 2 | 3 | 4 | 5 | 6 |
| 1) | behenyltrimethylammonium chloride | | | | | 3 | | | | | |
| 2) | cetostearyl alcohol | | | | | 4.5 | | | | | |
| 3) | behenyl alcohol | | | | | 2 | | | | | |
| 4) | dimethylpolysiloxane (6 mm²/s) | | | | | 20 | | | | | |
| 5) | (bisisobutyl PEG-14/ amodimethicone) copolymer | | | | | 6 | | | | | |
| 6) | higher alcohol-modified silicone No. 1 | 2 | | | | | | | | | |
| | higher alcohol-modified silicone No. 2 | | 2 | | | | | | | | |
| | higher alcohol-modified silicone No. 3 | | | 2 | | | | | | | |
| | higher alcohol-modified silicone No. 4 | | | | 2 | | | | | | |
| | higher alcohol-modified silicone No. 9 (comparative compound) | | | | | | 2 | | | | |
| | carbinol-modified silicone*[1] | | | | | | | 2 | | | |
| | dimethicone (50 mm²/s)*[2] | | | | | | | | 2 | | |
| | phenyltrimethicone*[3] | | | | | | | | | 2 | |
| | caprylylmethicone*[4] | | | | | | | | | | 2 |
| | dimethiconol (50 mm²/s) | | | | | | | | | | 2 |
| 7) | stearyl alcohol | | | | | 2 | | | | | |
| 8) | polyoxyethylene derivative of hydrogenated castor oil (60 mol EO adduct) | | | | | 0.3 | | | | | |
| 9) | polyoxyethylene stearyl ether (4 mol EO adduct) | | | | | 1 | | | | | |
| 10) | soy lecithin | | | | | 0.5 | | | | | |
| 11) | glycerol | | | | | 10 | | | | | |
| 12) | dipropylene glycol | | | | | 5 | | | | | |
| 13) | Yellow No. 4 | | | | | 5 | | | | | |
| 14) | fragrance | | | | | suitable amount | | | | | |
| 15) | preservative | | | | | suitable amount | | | | | |
| 16) | EDTA-3Na | | | | | suitable amount | | | | | |
| 17) | ion-exchanged water | | | | | balance | | | | | |

*[1] product name: DC5562 Carbinol Fluid, from Dow Corning Toray Co., Ltd.
*[2] product name: SH200-50cs, from Dow Corning Toray Co., Ltd.
*[3] product name: SH556, from Dow Corning Toray Co., Ltd.
*[4] product name: FZ3196, from Dow Corning Toray Co., Ltd.

Example

Hair Treatment Cream (Example 5)

The hair treatment cream of Example 5 was prepared proceeding as in Example 1, but in this case using 2 mass parts higher alcohol-modified silicone No. 8 in place of the higher alcohol-modified silicone No. 1 used in Example 1. The same evaluations as above were performed.

The sensory test results are reported in Table 3 below for the hair treatment creams of Examples 1 to 5 and Comparative Examples 1 to 6. The heat treatment creams of Examples 1 to 5 and particularly the hair treatment creams of Examples 1 to 4 gave strong impressions of the distinctive suede-like tactile feel and also provided excellent results for the other evaluated items. On the other hand, in the case of Comparative Examples 1 to 6, the suede-like tactile feel was either entirely or almost entirely absent and the other evaluated items were either the same as or inferior to the examples.

TABLE 3

| evaluated items | examples | | | | | comparative examples | | | | | |
|---|---|---|---|---|---|---|---|---|---|---|---|
| | 1 | 2 | 3 | 4 | 5 | 1 | 2 | 3 | 4 | 5 | 6 |
| suede-like tactile feel | 4.7 | 4.3 | 4.2 | 4.5 | 4.0 | 3.1 | 2.2 | 1.0 | 1.1 | 2.3 | 2.2 |
| hair luster | 4.8 | 4.5 | 4.3 | 4.4 | 4.0 | 3.0 | 1.6 | 1.9 | 2.3 | 2.7 | 1.5 |
| post-drying smoothness | 4.2 | 4.3 | 4.2 | 4.3 | 4.2 | 3.3 | 2.9 | 2.3 | 2.8 | 2.8 | 3.1 |
| suede-like tactile feel after brushing test | 4.3 | 4.0 | 4.3 | 4.2 | 3.7 | 2.6 | 1.7 | 1.0 | 1.0 | 2.0 | 1.3 |

TABLE 3-continued

|  | examples | | | | | comparative examples | | | | | |
|---|---|---|---|---|---|---|---|---|---|---|---|
| evaluated items | 1 | 2 | 3 | 4 | 5 | 1 | 2 | 3 | 4 | 5 | 6 |
| moisturizing effect on the hair | 4.6 | 4.2 | 4.1 | 4.5 | 4.3 | 3.4 | 2.9 | 1.7 | 2.0 | 2.3 | 2.4 |
| split end-preventing effect | 4.5 | 4.2 | 4.3 | 4.1 | 4.1 | 3.4 | 2.1 | 3.0 | 1.9 | 2.0 | 2.9 |

Examples

Powder Foundations

Examples 6 to 9 and Comparative Examples 7 to 12

Powder foundations with the compositions in Table 4 were prepared and were evaluated for the suede-like tactile feel, spreading on the skin, smoothness when applied, perception of adherence to the skin, and moisturizing sensation. The method of producing the cosmetic is given below. Among the individual components, component 14 is the higher alcohol-modified silicone according to the present invention or its comparative compound.

Production Method

Step 1. Mix and dissolve components 12 to 19.

Step 2. Mix components 1 to 11 to uniformity.

Step 3. Add the mixture obtained in step 1 to the step 2 mixture with stirring and grind.

Step 4. The ground powder obtained in step 3 is press molded into a metal tray using a die to yield the product.

TABLE 4

| | component (unit: mass parts) | examples | | | | comparative examples | | | | | |
|---|---|---|---|---|---|---|---|---|---|---|---|
| | | 6 | 7 | 8 | 9 | 7 | 8 | 9 | 10 | 11 | 12 |
| 1 | octylsilane-treated talc | balance | | | | | | | | | |
| 2 | octylsilane-treated sericite | 23 | | | | | | | | | |
| 3 | dimethicone/vinyldimethicone crosspolymer/silica (Note 1) | 1 | | | | | | | | | |
| 4 | silicone-treated titanium oxide | 9 | | | | | | | | | |
| 5 | finely divided silicone-treated zinc oxide | 5 | | | | | | | | | |
| 6 | finely divided silicone-treated titanium oxide | 5 | | | | | | | | | |
| 7 | octylsilane-treated iron oxide red | 0.2 | | | | | | | | | |
| 8 | octylsilane-treated iron oxide yellow | 1.4 | | | | | | | | | |
| 9 | octylsilane-treated iron oxide black | 0.3 | | | | | | | | | |
| 10 | octylsilane-treated barium sulfate plates (average particle size = 30 μm) | 10 | | | | | | | | | |
| 11 | polymethyl methacrylate | 7.5 | | | | | | | | | |
| 12 | paraben | 0.2 | | | | | | | | | |
| 13 | phenylmethylsilicone | 2 | | | | | | | | | |
| 14 | higher alcohol-modified silicone No. 1 | 5 | | | | | | | | | |
| | higher alcohol-modified silicone No. 2 | | 5 | | | | | | | | |
| | higher alcohol-modified silicone No. 3 | | | 5 | | | | | | | |
| | higher alcohol-modified silicone No. 4 | | | | 5 | | | | | | |
| | higher alcohol-modified silicone No. 9 (comparative compound) | | | | | 5 | | | | | |
| | carbinol-modified silicone*[1] | | | | | | 5 | | | | |
| | dimethicone (50 mm$^2$/s)*[2] | | | | | | | 5 | | | |
| | phenyltrimethicone*[3] | | | | | | | | 5 | | |
| | caprylylmethicone*[4] | | | | | | | | | 5 | |
| | dimethiconol (50 mm$^2$/s) | | | | | | | | | | 5 |
| 15 | 2-ethylhexyl para-methoxycinnamate | 1 | | | | | | | | | |
| 16 | diisostearyl malate | 1 | | | | | | | | | |
| 17 | white petrolatum | 1 | | | | | | | | | |
| 18 | 1,3-butylene glycol | 0.1 | | | | | | | | | |
| 19 | fragrance | suitable amount | | | | | | | | | |

Note 1.

DC9701, from Dow Corning Toray Co., Ltd.

*[1]product name: DC5562 Carbinol Fluid, from Dow Corning Toray Co., Ltd.

*[2]product name: SH200-50cs, from Dow Corning Toray Co., Ltd.

*[3]product name: SH556, from Dow Corning Toray Co., Ltd.

*[4]product name: FZ3196, from Dow Corning Toray Co., Ltd.

Example

Powder Foundation (Example 10)

The powder foundation of Example 10 was prepared proceeding as in Example 6, but in this case using 5 mass parts higher alcohol-modified silicone No. 8 in place of the higher alcohol-modified silicone No. 1 used in Example 6. The same evaluations as above were performed.

The sensory test results are reported in Table 5 below for the powder foundations of Examples 6 to 10 and Comparative Examples 7 to 12. The powder foundations of Examples 6 to 10 and particularly of Examples 6 to 9 gave strong impressions of the distinctive suede-like tactile feel and also provided excellent results for the other evaluated items. On the other hand, in the case of Comparative Examples 7 to 12, the suede-like tactile feel was either entirely or almost entirely absent and the other evaluated items were either the same as or inferior to the examples.

higher alcohol comparative compound was 1:1 in these compatibility tests, and the solubility was evaluated from the appearance of the mixture based on the presence/absence of separation. The specific cosmetic ingredients 1 to 9 are given below.

cosmetic ingredient 1: decamethylcyclopentasiloxane
cosmetic ingredient 2: dimethylpolysiloxane (6 mm$^2$/s)
cosmetic ingredient 3: dimethylpolysiloxane (100 mm$^2$/s)
cosmetic ingredient 4: liquid paraffin
cosmetic ingredient 5: cetyl 2-ethylhexanoate
cosmetic ingredient 6: trioctanoin
cosmetic ingredient 7: glycerol
cosmetic ingredient 8: 1,3-butylene glycol
cosmetic ingredient 9: ethanol

TABLE 5

| evaluated items | examples | | | | | comparative examples | | | | | |
|---|---|---|---|---|---|---|---|---|---|---|---|
|  | 6 | 7 | 8 | 9 | 10 | 7 | 8 | 9 | 10 | 11 | 12 |
| suede-like tactile feel | 4.4 | 4.2 | 4.2 | 4.4 | 4.0 | 3.1 | 2.0 | 1.3 | 1.6 | 2.0 | 1.8 |
| spreading on the skin | 4.3 | 4.0 | 4.2 | 4.2 | 4.1 | 2.8 | 2.3 | 2.5 | 3.1 | 3.0 | 2.8 |
| smoothness when applied | 4.5 | 4.3 | 4.1 | 4.0 | 4.2 | 3.0 | 3.1 | 3.2 | 2.9 | 3.3 | 2.7 |
| perception of adherence to the skin | 4.2 | 4.2 | 4.2 | 4.1 | 4.2 | 3.3 | 3.0 | 2.0 | 2.9 | 3.0 | 2.9 |
| moisturizing sensation | 4.2 | 4.3 | 4.2 | 4.3 | 4.2 | 3.3 | 3.1 | 2.2 | 2.1 | 2.9 | 3.0 |

Test Example 1

Test of Compatibility with Other Cosmetic Ingredients

The higher alcohol-modified silicone according to the present invention exhibits a better compatibility with cosmetic ingredients and particularly oils than is exhibited by higher alcohols in general and thus is a very useful cosmetic ingredient from the standpoint of the capacity for incorporation in a broad range of cosmetic formulations. Therefore, in order to objectively demonstrate the usefulness of the higher alcohol-modified silicone, tests were carried out on the compatibility between cosmetic ingredients 1 to 9, which are widely used in various cosmetics, and the higher alcohol-modified silicones obtained in Synthesis Examples 1 to 4 or a higher alcohol comparative compound. The mixing ratio between the oil and the higher alcohol-modified silicone or The test results are reported in Table 6 below. Excluding anomalies such as glycerol, it was confirmed that the higher alcohol-modified silicone according to the present invention gave a uniform mixture with almost all of the oils and had an excellent compatibility with oily cosmetic ingredients.

TABLE 6

| cosmetic ingredient | 1 | 2 | 3 | 4 | 5 | 6 | 7 | 8 | 9 |
|---|---|---|---|---|---|---|---|---|---|
| higher alcohol-modified silicone |  |  |  | diss. |  |  |  | sep. | diss. |
| No. 1 |  |  |  |  |  |  |  |  |  |
| No. 2 |  |  |  |  |  |  |  |  |  |
| No. 3 |  |  |  |  |  |  |  |  |  |
| No. 4 |  |  |  |  |  |  |  |  |  |
| isostearyl alcohol | diss. | sep. | sep. | diss. | diss. | diss. | sep. | diss. | diss. | abbreviations used:
diss. = dissolution;
sep. = separation

Test Example 2

Test of the Improvement in Higher Alcohol Crystallinity Due to the Use of the Higher Alcohol-Modified Silicone When used in combination with a higher alcohol, the higher alcohol-modified silicone according to the present invention is a useful cosmetic ingredient because it can effectively inhibit crystallization of the higher alcohol and can thereby improve the use sensation presented by the cosmetic. Therefore, in order to objectively demonstrate the usefulness of the higher alcohol-modified silicone, the higher alcohol-modified silicone according to the present invention was blended with a higher alcohol using the compositions shown below in Table 7; complete dissolution was brought about at 80° C.; and the status of crystallization was evaluated based on the presence/absence of solidification. The results obtained for the evaluation of crystallinity are also shown in Table 7.

inventive product and the higher alcohol, heated to 70° C., was added. The gel was obtained after stirring and cooling.

The thermal behavior of the obtained gel was measured by differential scanning calorimetric analysis (DSC). The presence/absence of gel formation in this test example is given in Table 8 for each composition. The results of the DSC measurements are shown in FIG. 1.

TABLE 7

| test example (unit: mass parts) | | 2-1 | 2-2 | 2-3 | comparative test example | comparative test example |
|---|---|---|---|---|---|---|
| cetanol | | 10 | 10 | 10 | 100 | 10 |
| higher alcohol-modified silicone | | | | | | |
| No. 1 | | 90 | 0 | 0 | 0 | 0 |
| No. 2 | | 0 | 90 | 0 | 0 | 0 |
| No. 3 | | 0 | 0 | 90 | 0 | 0 |
| C12 alkyl-modified trisiloxane (comparative compound)*1 | | 0 | 0 | 0 | 0 | 90 |
| crystallization status | after 30 minutes | liquid | liquid | liquid | solidification (after 10 min) | solidification (after 30 min) |
| | after 1 hour | liquid | solidification | solidification | solidification | solidification |
| | after 3 days | solidification, fluidity recovered by percussion | solidification | solidification | solidification | solidification |

*1: modified trisiloxane given by $MD^{R*}M$; the modifying group R is the dodecyl group.

As may be understood from the results given in Table 7, the higher alcohol-modified silicone according to the present invention inhibits the crystallization of cetanol, a higher alcohol. In the particular case of the higher alcohol-modified silicone No. 1, which has a trisiloxane structure, it was found that the crystallization of cetanol was effectively inhibited and solidification, i.e., crystallization, did not occur for a long period of time at room temperature, and that even after crystallization occurred the fluidity could be recovered by the application of physical percussion. On the other hand, the higher alcohol-containing compositions of the comparative test example solidified within 30 minutes and almost no inhibition of crystallization was obtained.

Test Example 3

(1) Formation of a Gel Structure Using the Higher Alcohol-Modified Silicone

The higher alcohol-modified silicone according to the present invention forms a very stable gel structure when added in small quantities to a gel structure comprising surfactant/higher alcohol/water and is thus a cosmetic ingredient that can be utilized in a broad range of cosmetic formulations and forms. Therefore, in order to objectively demonstrate the usefulness of the higher alcohol-modified silicone, gels were prepared from cationic surfactant/higher alcohol/higher alcohol-modified silicone according to the present invention/water based on the compositions given in Table 8 below and the generation of changes in the gel structure due to the addition of the higher alcohol-modified silicone was checked.

The specific method for forming the gel was as follows. A mixed solution of water and the cationic surfactant, heated to 70° C., was stirred using a homomixer and a mixture of the The instrument used for the differential scanning calorimetric analysis (DSC) was a DSC6200 from Seiko Instruments Inc.

TABLE 8

| Gel compositions using cationic surfactant | | | |
|---|---|---|---|
| gel composition (unit: mass parts) | test example 3-1 | test example 3-2 | comparative test example |
| stearyltrimethylammonium chloride | 1 | 1 | 1 |
| cetanol | 2 | 2.5 | 3 |
| higher alcohol-modified silicone No. 1 | 1 | 0.5 | — |
| ion-exchanged water | 96 | 96 | 96 |
| total | 100 | 100 | 100 |
| presence/absence of gel structure | present | present | present |

Test Example 4

(2) Formation of a Gel Structure Using the Higher Alcohol-Modified Silicone

Proceeding as in Test Example 2, gels were prepared from anionic surfactant/higher alcohol/higher alcohol-modified silicone according to the present invention/water based on the compositions given in Table 9 below in order to check for the generation of changes in the gel structure due to the addition of the higher alcohol-modified silicone. The anionic surfactant used is the potassium stearate generated from the stearic acid and potassium hydroxide.

The gel production method was according to that for the previously described cationic surfactant.

Figure 2:
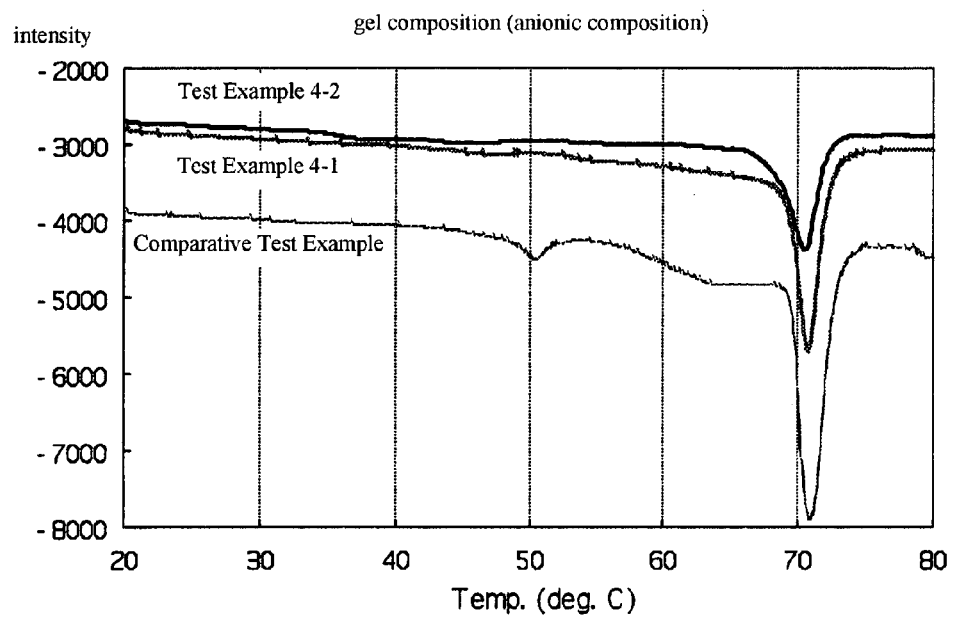
FIG. 2 gives the results of differential scanning calorimetric (DSC) measurements on Test Examples 4-1 and 4-2 and their comparative test example: "Gel composition comprising an anionic surfactant (potassium stearate)/cetanol/water"

The thermal behavior of the obtained gel was measured by differential scanning calorimetric analysis (DSC). The presence/absence of gel formation in this test example is given in Table 9 for each composition. The results of the DSC measurements are shown in FIG. 2.

TABLE 9

Gel compositions using anionic surfactant

| gel composition (unit: mass parts) | test example 4-1 | test example 4-2 | comparative test example |
|---|---|---|---|
| stearic acid | 3.3 | 3.3 | 3.3 |
| cetanol | 13.9 | 11.1 | 16.7 |
| higher alcohol-modified silicone No. 1 | 2.8 | 5.6 | — |
| potassium hydroxide | 0.62 | 0.62 | 0.62 |
| ion-exchanged water | 79.38 | 79.38 | 79.38 |
| total | 100 | 100 | 100 |
| presence/absence of gel structure | present | present | present |

As shown in Tables 8 and 9 and FIGS. 1 and 2, the formation of a stable gel structure was confirmed for the addition of the higher alcohol-modified silicone according to the present invention to a system of cationic surfactant+higher alcohol+water and to a system of anionic surfactant+higher alcohol+water. As shown in Test Example 2 above, the higher alcohol-modified silicone according to the present invention inhibits the crystallization of higher alcohol, but, surprisingly, does not interfere with the formation of a stable gel structure regardless of the type of surfactant, and thus can be regarded as capable of stable incorporation even in cosmetics that are higher alcohol-containing gel systems.

Example

Emulsions (Examples 11 to 13 and Comparative Examples 13 to 15)

Oil-in-water emulsion-type cosmetics (skin cosmetics) using the higher alcohol-modified silicone according to the present invention were prepared in the form of emulsions that used a dimethylpolysiloxane (6 mm$^2$/s) and decamethylcyclopentasiloxane (D5) in accordance with the compositions given in Table 10, and the stability and tactile feel of the emulsions were evaluated for different higher alcohols. The method of producing the emulsion and the method of evaluating the stability are given below. The previously described method and criteria were used for the method of evaluating the tactile feel and the evaluation criteria.

Emulsion Preparation Method
1) The water and potassium hydroxide are heated to 70° C. and stirred with a homomixer at 5000 rpm.
2) The surfactant heated to 70° C. is mixed at 70° C. with the inventive product, higher alcohol, and oil and the aqueous phase is gradually added.
3) Stirring is performed for 5 minutes after the addition and cooling is carried out to 30° C. while stirring.

Emulsion Stability

The emulsions prepared in Examples 11 to 13 and Comparative Example 13 were filled into clear glass jars, which were sealed. After holding for 1 month in a 50° C. oven, the status of the emulsion was visually evaluated.

TABLE 10

| | | examples | | | comparative examples | | |
|---|---|---|---|---|---|---|---|
| components (unit: mass parts) | | 11 | 12 | 13 | 13 | 14 | 15 |
| surfactant | stearic acid | 3.3 | 3.3 | 3.3 | 3.3 | 3.3 | 3.3 |
| higher alcohol | cetanol | 2.75 | 1.375 | 0 | 3.3 | 0 | 0 |
| | stearyl alcohol | 0 | 1.375 | 1.375 | 0 | 3.3 | 0 |
| | behenyl alcohol | 0 | 0 | 1.375 | 0 | 0 | 3.3 |
| higher alcohol-modified silicone | higher alcohol-modified silicone No. 1 | 0.55 | 0.55 | 0.55 | 0 | 0 | 0 |
| oil | dimethylsiloxane (6 mm$^2$/s) | 5 | 5 | 5 | 5 | 5 | 5 |
| | decamethyl-cyclopentasiloxane | 5 | 5 | 5 | 5 | 5 | 5 |
| water | ion-exchanged water | 82.78 | 82.78 | 82.78 | 82.78 | 82.78 | 82.78 |
| | potassium hydroxide | 0.62 | 0.62 | 0.62 | 0.62 | 0.62 | 0.62 |
| emulsion stability (50° C./1 month) | | stable | stable | stable | partial separation | partial separation | partial separation |
| quality of the use sensation for the emulsion | | 4.6 | 4.4 | 4.3 | 2.3 | 2.0 | 2.0 |
| quality of the water resistance of the emulsion | | 4.3 | 4.4 | 4.4 | 1.6 | 1.4 | 1.5 |
| quality of the suede-like tactile feel | | 4.2 | 4.1 | 4.2 | 1.0 | 1.0 | 1.0 |

As the preceding makes clear, the incorporation of the higher alcohol-modified silicone according to the present invention makes possible the stable incorporation of silicone oils, which are typically refractory to emulsification, and thus makes possible the preparation of an oil-in-water emulsion-type cosmetic that exhibits an excellent tactile feel.

Example 14

Emulsion

| | | |
|---|---|---|
| 1) ion-exchanged water | balance | |
| 2) para-hydroxybenzoate ester | 0.1 | part |
| 3) phenoxyethanol | 0.2 | part |
| 4) 1,3-butylene glycol | 7 | parts |
| 5) glycerol | 5 | parts |
| 6) carboxyvinyl polymer | 0.04 | part |
| 7) xanthan gum | 0.02 | part |
| 8) potassium hydroxide | 0.04 | part |
| 9) stearic acid | 0.8 | part |
| 10) self-emulsifying glycerol monostearate | 0.8 | part |
| 11) polyethylene glycol monostearate | 1.1 | parts |
| 12) cetostearyl alcohol | 0.5 | part |
| 13) higher alcohol-modified silicone No. 1 | 0.1 | part |
| 14) decamethylcyclopentasiloxane | 3 | parts |
| 15) dimethylpolysiloxane (6 mm$^2$/s) | 3 | parts |
| 16) trioctanoin | 2 | parts |
| 17) squalane | 2 | parts |

Production Method

The oil phase of 9) to 17) heated to 75° C. was gradually added to the aqueous phase of 1) to 8) heated to 75° C.; emulsification was carried out followed by cooling and filling into a container to obtain the product.

The resulting emulsion exhibited a stable emulsified state and a moderate suede-like tactile feel; lacked stickiness for the skin; and exhibited an excellent moist tactile feel.

Example 15

Skin Care Cream

| | | |
|---|---|---|
| 1) stearic acid | 2 | parts |
| 2) cetostearyl alcohol | 1.5 | parts |
| 3) higher alcohol-modified silicone No. 1 | 0.3 | part |
| 4) glycerol monostearate | 1.5 | parts |
| 5) sorbitan stearate | 0.5 | part |
| 6) polyoxyethylene sorbitan (20 EO) monooleate | 0.5 | part |
| 7) liquid paraffin | 10 | parts |
| 8) decamethylcyclopentasiloxane | 5 | parts |
| 9) dimethylpolysiloxane (6 mm$^2$/s) | 1 | part |
| 10) glycerol trioctanoate | 3 | parts |
| 11) triethanolamine | 1.5 | parts |
| 12) 1,3-butylene glycol | 10 | parts |
| 13) purified water | balance | |

Production Method 11) to 13) heated to 70° C. was gradually added with emulsification to 1) to 10), which had been dissolved by heating to 70° C.; cooling was performed and the product was obtained by filling into a container.

The resulting skin care cream was stable with elapsed time and had a suede-like tactile feel; it exhibited an excellent spreadability and a good skin absorbability/compatibility and lacked stickiness; and it provided an excellent emollient sensation by bringing about a moisturizing sensation and a moist skin feel.

Example 16

Cleansing Cream

| | | |
|---|---|---|
| 1) acrylic acid-alkyl methacrylate copolymer (Note 1) | 0.25 | part |
| 2) 1% aqueous sodium hydroxide solution | 7.0 | parts |
| 3) dipropylene glycol | 5.0 | parts |
| 4) glycerol | 15.0 | parts |
| 5) purified water | balance | |
| 6) sucrose fatty acid ester | 0.5 | part |
| 7) polyoxyethylene (2 EO) cocofatty acid monoethanolamide | 0.5 | part |
| 8) tocopherol acetate | 0.1 | part |
| 9) preservative | suitable quantity | |
| 10) fragrance | suitable quantity | |
| 11) ethanol | 4.5 | parts |
| 12) higher alcohol-modified silicone No. 2 | 0.5 | part |

(Note 1):
Pemulen TR-1 from Lubrizol Japan Limited

Production Method

Components 1) to 5) were mixed to uniformity; components 6) to 12) were mixed and dissolved to uniformity; and the preceding were combined with mixing, followed by filling into a container to obtain the product.

The resulting cleansing cream had an excellent cleansing performance and during use provided a suede-like feel; after washing off, an excellent moist skin feel and smoothness were present, while a fresh tactile feel persisted.

Example 17

Make-Up Remover (Weakly Emulsified Type)

| | | |
|---|---|---|
| 1) acrylic acid · alkyl methacrylate copolymer (Note 1) | 0.1 | part |
| 2) triethanolamine | 0.05 | part |
| 3) methyltrimethicone | 7 | parts |
| 4) squalane | 1 | part |
| 5) higher alcohol-modified silicone No. 3 | 2 | parts |
| 6) vitamin E acetate | 0.2 | part |
| 7) polyether-modified silicone | 0.5 | part |
| 8) sodium hyaluronate | 1 | part |
| 9) disodium edetate | 0.1 | part |
| 10) propylene glycol | 7 | parts |
| 11) phenoxyethanol | suitable quantity | |
| 12) purified water | balance | |

(Note 1):
Pemulen TR-1 from Lubrizol Japan Limited

Production Method

Components 1) and 2) and 6) to 12) were mixed to uniformity; the mixture of components 3) to 7) was added; emulsification was performed; and the product was obtained by filling into a container.

The resulting make-up remover had an excellent emulsion stability and an excellent cleansing action for a variety of make-up cosmetics, did not cause an oily or sticky sensation during or after use, and had a fresh use sensation. In addition, after the skin had been wiped off with a towel or handkerchief, the skin was not taut and the smoothness and moist feel were intact.

Example 18

Cleansing Oil

| | | |
|---|---|---|
| 1) cetyl octanoate | 1 part | |
| 2) squalane | 10 parts | |
| 3) trioctanoin | balance | |
| 4) trimethylolpropane triisostearate | 20 parts | |
| 5) jojoba oil | 3 parts | |
| 6) macadamia nut oil | 2 parts | |
| 7) decamethylcyclopentasiloxane | 4 parts | |
| 8) dimethylsilicone (6 mm$^2$/s) | 1 part | |
| 9) caprylmethicone | 1.0 part | |
| 10) fragrance | 0.1 part | |
| 11) dibutylhydroxytoluene | 0.1 part | |
| 12) heavy liquid isoparaffin | 4.0 parts | |
| 13) higher alcohol-modified silicone No. 4 | 3.5 parts | |
| 14) polyoxyethylene sorbitol tetraoleate (HLB 11.5) | 2.5 parts | |
| 15) diglyceryl diisostearate | 5.0 parts | |

Production Method

Components 1 to 14 were mixed to uniformity and filled into a container to obtain the product.

The resulting cleansing oil had a good absorbability/compatibility for the skin and exhibited an excellent dirt removal activity when wiped off with dirt with a tissue or cotton; cleansing could be conveniently carried out; there was no oily or sticky feel after use; and the tactile feel post-use was also excellent.

Example 19

Oil-in-Water Emulsion

| | |
|---|---|
| 1) stearic acid | 1 part |
| 2) polysorbate 80 | 0.3 part |
| 3) sorbitan sesquioleate | 0.2 part |
| 4) glyceryl stearate | 0.2 part |
| 5) stearyl alcohol | 0.5 part |
| 6) behenyl alcohol | 0.5 part |
| 7) higher alcohol-modified silicone No. 1 | 1.0 part |
| 8) pentaerythrityl tetraoctanoate | 2 parts |
| 9) methyltrimethicone | 4.5 parts |
| 10) mineral oil | 1 part |
| 11) water | balance |
| 12) DPG | 8 parts |
| 13) glycerol | 4 parts |
| 14) preservative | suitable quantity |
| 15) triethanolamine | 0.5 part |
| 16) carboxyvinyl polymer | 21 parts |
| 17) *camellia* oil | 0.5 part |
| 18) *Paeonia albiflora* extract | 0.5 part |

Production Method
1. Mix and dissolve components 1 to 10 at 70° C. to uniformity.
2. Mix and dissolve components 11 to 18 at 70° C. to uniformity.
3. The aqueous liquid obtained in step 2 is gradually added at 70° C. with stirring to the oily liquid obtained in step 1; filling into a container then provides the product.

The resulting oil-in-water emulsion had an excellent storage stability and maintained a stable emulsion state without the occurrence of changes in the appearance with elapsed time and without the occurrence of viscosity changes when the temperature was changed. In addition, there was a suede-like sensation when used and there was no sticky sensation on the skin and the use sensation was excellent.

Example 20

Lipstick

| | |
|---|---|
| 1) microcrystalline wax | 10.0 parts |
| 2) paraffin wax | 15.0 parts |
| 3) carnauba wax | 5.0 parts |
| 4) petrolatum | 5.0 parts |
| 5) diisostearyl malate | 7.0 parts |
| 6) glyceryl triisostearate | 11.5 parts |
| 7) propylene glycol dicaprate | 7.0 parts |
| 8) inulin stearate (product name: Rheopearl ISL2 from Chiba Flour Milling Co., Ltd.) | 2.0 parts |
| 9) higher alcohol-modified silicone No. 7 | 3.0 parts |
| 10) decamethylcyclopentasiloxane | 10.0 parts |
| 11) FA 4001 CM, Note 1) | 3.0 parts |
| 12) DC 593, Note 2) | 2.0 parts |
| 13) Red No. 201 | 1.0 part |
| 14) Red No. 202 | 1.0 part |
| 15) Yellow No. 4 | 2.0 parts |
| 16) titanium oxide | 4.0 parts |
| 17) iron oxide black | 0.5 part |
| 18) iron oxide titanium mica | 3.0 parts |
| 19) titanium mica | 2.0 parts |
| 20) purified water | 5.0 parts |
| 21) 1,3-butylene glycol | 1.0 part |
| 22) preservative | suitable quantity |
| 23) fragrance | suitable quantity |

Note 1)
a decamethylcyclopentasiloxane solution of an acrylates/polytrimethylsiloxy-methacrylate copolymer, with an effective component content of 30%
Note 2)
a dimethylpolysiloxane (100 mm$^2$/s) solution of a trimethylsiloxysilicic acid, containing 33% effective component Production Method Heat and dissolve components 1) to 19); mix a mixture of components 20) to 22) to uniformity; then combine and mix. Add component 23) and fill into an airtight container to obtain the product.

The lipstick of this example is a formulation prepared by incorporating higher alcohol-modified silicone No. 7, which is a siloxane dendrimer+higher alcohol co-modified silicone, into a lipstick, which is an oil-based solid cosmetic that takes the form of a stick cosmetic. The lipstick provided by this formulation gave a suede-like material feel and a high-quality feel when applied on the lips; the spreadability was excellent and a uniform application on the lips was obtained; and a finish with an excellent gloss and transparency was provided. In addition, no stickiness was perceived on the lips post-application, and the storage stability was also excellent when the product was executed as a stick.

Example 21

Lip Gloss (Components)

| | |
|---|---|
| 1) higher alcohol-modified silicone No. 5 | 10.0 parts |
| 2) silicic anhydride (average primary particle size = 10 nm) | 1.5 parts |
| 3) diisostearyl malate | 15.0 parts |
| 4) stearyl alcohol | 4.0 parts |
| 5) methyltrimethicone | 1.0 part |
| 6) phenyltrimethicone | 3.0 parts |

| | |
|---|---|
| 7) heavy liquid isoparaffin | balance |
| 8) trimethylpentaphenyltrisiloxane | 1.0 part |
| 9) squalane | 9.0 parts |
| 10) sunflower oil | 5.0 parts |
| 11) tricaprylylglyceryl (=glyceryl tricaprate) | 5.0 parts |
| 12) petrolatum | 5.0 parts |
| 13) microcrystalline wax | 2.0 parts |
| 14) Red No. 202 | 0.8 part |
| 15) titanium mica | 3.0 parts |

Production Method

The listed components were mixed at 90° C., filled into a container, and cooled to provide the product.

The lip gloss of this example is a formulation made by the incorporation in a lip gloss, which is an oil-based make-up cosmetic, of higher alcohol-modified silicone No. 5, in which a co-modification has been implemented using three different functional groups, i.e., a long-chain alkyl group, siloxane dendrimer, and a higher alcohol modifying group. The lip gloss provided by this example gave a suede-like material feel and a high-quality feel when applied on the lips; with regard to cosmetic effect, its cosmetic film exhibited an excellent persistence with regard to color, gloss, and an attractive sparkly appearance; in addition, the spreadability was excellent and a uniform finish was provided. Moreover, when the product was executed as a stick, there was no separation between the oil phase and powder phase and the storage stability was also excellent.

Example 22

Sunscreen Emulsion (W/O Type)

(Components)

| | |
|---|---|
| 1) 2-ethylhexyl para-methoxycinnamate | 4.0 parts |
| 2) hexyl diethylaminohydroxybenzoylbenzoate | 1.0 part |
| 3) silicone-treated finely divided titanium oxide | 5.0 parts |
| 4) silicone-treated finely divided zinc oxide | 9.0 parts |
| 5) squalane | 15.0 parts |
| 6) dioctyl succinate | 5.0 parts |
| 7) higher alcohol-modified silicone No. 6 | 5.0 parts |
| 8) dimethicone (2 mm$^2$/s) | 10 parts |
| 9) decamethylcyclopentasiloxane | 8.0 parts |
| 10) decamethylcyclopentasiloxane/ (acrylates/polytrimethylsiloxy- methacrylate) copolymer (Note 1) | 2 parts |
| 11) glycerol diisostearate | 2.0 parts |
| 12) polyether-modified silicone (Note 2) | 0.5 part |
| 13) organomodified montmorillonite | 0.5 part |
| 14) purified water | balance |
| 15) 1,3-butylene glycol | 5 parts |

(Note 1):
FA 4001 CM Silicone Acrylate from Dow Corning Toray Co., Ltd., was used.
(Note 2):
SS-2910 from Dow Corning Toray Co., Ltd., was used.

Production Method

1. Components 3 and 4 were mixed with components 7 to 10 and very finely ground. This was added with thorough stirring to a solution prepared by heating components 1, 2, 5, 6, 11, 12, and 13 to 60° C. and mixing to uniformity.
2. A solution of components 14 and 15 was gradually added with stirring to the oil phase obtained in step 1; emulsification was performed; and the product was obtained by filling into a container.

The sunscreen emulsion according to Example 22 is a formulation made by the incorporation in a sunscreen emulsion, i.e., a water-in-oil emulsion-type cosmetic, of higher alcohol-modified silicone No. 6, which has been co-modified by a long-chain alkyl group and a higher alcohol modifying group. When applied to the skin, the sunscreen emulsion obtained in this example had a suede-like feel, exhibited an excellent spreadability, had an excellent use sensation with a reduced stickiness, was not irritating to the skin, and provided a persistent ultraviolet protective effect. Moreover, separation did not occur even at the high temperatures expected for the summertime, and the timewise stability was excellent notwithstanding the content of an inorganic ultraviolet protective component and a large amount of an aqueous phase component. In addition, when used as a cosmetic foundation, an improved cosmetic durability was obtained for subsequently applied make-up cosmetics.

Example 23

Sunscreen Emulsion (W/O Type)

| | |
|---|---|
| 1) finely divided titanium oxide slurry (decamethylcyclopentasiloxane solution, 30% solids fraction) | 10 parts |
| 2) finely divided zinc oxide slurry (decamethylcyclopentasiloxane solution, 35% solids fraction) | 30 parts |
| 3) 2-ethylhexyl para-methoxycinnamate | 8 parts |
| 4) hexyl diethylaminohydroxybenzoylbenzoate | 2 parts |
| 5) higher alcohol-modified silicone No. 5 | 4 parts |
| 6) caprylmethicone | 3 parts |
| 7) trimethylsiloxysilicic acid solution | 7.5 parts |
| 8) dimethicone (6 mm$^2$/s) | 4.5 parts |
| 9) PEG-10 dimethicone (Note 1) | 1 part |
| 10) isodecyl isononanoate | 1 part |
| 11) silica | 2.5 parts |
| 12) purified water | balance |
| 13) preservative | suitable quantity |
| 14) 1,3-propanediol | 2 parts |
| 15) aloe extract | 1 part |

(Note 1):
SS-2910 from Dow Corning Toray Co., Ltd., was used.

Production Method
1. Components 1 to 10 are mixed and dispersed to uniformity.
2. Components 11 to 15 are mixed and dissolved.
3. The aqueous phase obtained in 2 is added with stirring to the oil-based dispersion obtained in step 1; emulsification is carried out; and filling into a container provides the product.

The sunscreen emulsion obtained in this example, when applied to the skin, had a suede-like feel, exhibited an excellent spreadability, had an excellent use sensation with a reduced stickiness, was not irritating, and provided a persistent ultraviolet protective effect. Moreover, separation did not occur even at the high temperatures expected for the summertime, and the timewise stability was excellent notwithstanding the content of an inorganic ultraviolet protective component and a large amount of an aqueous phase component.

Example 24

Sunscreen (O/W) Cream

| | |
|---|---|
| 1) PEG/PPG-30/10 dimethicone, other dimethicones (Note 1) | 10 parts |
| 2) sodium tri(POE)lauryl ether phosphate | 0.05 part |
| 3) hexyl diethylaminohydroxybenzoylbenzoate | 2 parts |
| 4) 2-ethylhexyl para-methoxycinnamate | 6 parts |

-continued

| | |
|---|---|
| 5) higher alcohol-modified silicone No. 2 | 3 parts |
| 6) dimethicone (6 mm²/s) | 2 parts |
| 7) phenyltrimethicone | 2 parts |
| 8) carbomer (2 mass % aqueous solution) | 22.5 parts |
| 9) purified water | balance |
| 10) sodium hydroxide (1 mass % aqueous solution) | 10.5 parts |
| 11) polyoxypropylene methyl glucoside | 0.4 part |
| 12) ethanol | 2 parts |
| 13) 1,3-butylene glycol | 5 parts |
| 14) glycerol | 5 parts |
| 15) preservative | suitable quantity |
| 16) (dimethicone/vinyldimethicone) crosspolymer (Note 2) | 2.5 parts |

(Note 1):
FB-2540 from Dow Corning Toray Co., Ltd., was used.
(Note 2):
BY29-129 from Dow Corning Toray Co., Ltd., was used.

Production Method
1. Components 8 to 15 are mixed to uniformity.
2. Components 1 to 7 are mixed to uniformity.
3. The oil layer of step 2 is added to the aqueous phase of step 1 and emulsification is carried out.
4. Component 16 is added with stirring and filling into a container then provides the product.

The sunscreen (O/W emulsion-type cream) obtained in this example, when applied to the skin, had a suede-like feel and had an excellent ultraviolet protective effect due to the incorporation of the organic ultraviolet protective components. On the other hand, separation of the oil phase and changes in appearance did not occur and the timewise stability was excellent. The use sensation was excellent and free of stickiness.

Example 25

Lip Gloss

| | |
|---|---|
| 1) polyamide-modified silicone (Note 1) | 19 parts |
| 2) higher alcohol-modified silicone No. 5 | 10 parts |
| 3) methylphenyl-modified silicone | 28 parts |
| 4) isononyl isononanoate | 38 parts |
| 5) trioctanoin | 2 parts |
| 6) titanium mica | 3 parts |

Note 1:
2-8178 Gellant from the Dow Corning Corporation was used.

Production Method

The individual components were mixed and heated at 100° C. and then filled into a container to provide the product.

The lip gloss of this example is a formulation made by the incorporation of higher alcohol-modified silicone No. 5—in which a co-modification has been implemented using three different functional groups, i.e., a long-chain alkyl group, siloxane dendrimer, and a higher alcohol modifying group—and by the incorporation of a polyamide-modified silicone, which also functions as an oil-soluble gellant. The lip gloss provided by this example is a paste, exhibits an excellent compatibility for the oily ingredients, and has an excellent storage stability when the product is executed as a stick. Furthermore, when used it gave a suede-like, thick film feel and with regard to its cosmetic effect its cosmetic film exhibited an excellent persistence with regard to color, gloss, and an attractive sparkly appearance; in addition, the spreadability was excellent and a uniform finish was provided. Moreover, no irritation was shown when used and the safety was therefore also excellent.

Example 26

Solid Eye Shadow Powder

| | |
|---|---|
| 1) metal soap | 20 parts |
| 2) mica | 30 parts |
| 3) nylon powder | 5 parts |
| 4) colored pigment | 10 parts |
| 5) titanium mica | 20 parts |
| 6) dimethylpolysiloxane (20 mm²/s) | 5 parts |
| 7) squalane | 2 parts |
| 8) liquid paraffin | 5 parts |
| 9) higher alcohol-modified silicone No. 4 | 3 parts |

Production Method
Components 1) to 5) were thoroughly mixed and components 6) to 9) were dissolved to uniformity and these were then added to the powder with mixing followed by pressing into a tray using a die to obtain the product.

When used, the solid eye shadow powder obtained in this example had a suede-like feel, spread smoothly, and also had an excellent color. It also characteristically resisted unwanted removal or disarrangement of the cosmetic.

Example 27

Powder Foundation (Treated Pigment Type)

| | |
|---|---|
| 1) higher alcohol-modified silicone-treated talc | balance |
| 2) higher alcohol-modified silicone-treated mica | 3 parts |
| 3) dimethicone/vinyldimethicone crosspolymer/silica (Note 1) | 1 part |
| 4) higher alcohol-modified silicone-treated titanium oxide | 9 parts |
| 5) silicone-treated finely divided zinc oxide | 5 parts |
| 6) silicone-treated finely divided titanium oxide | 5 parts |
| 7) higher alcohol-modified silicone-treated iron oxide red | 0.2 part |
| 8) higher alcohol-modified silicone-treated iron oxide yellow | 1.4 parts |
| 9) higher alcohol-modified silicone-treated iron oxide black | 0.3 part |
| 10) barium sulfate plates (average particle size = 30 μm) | 7.5 parts |
| 11) polymethyl methacrylate | 7.5 parts |
| 12) paraben | 0.2 part |
| 13) phenylmethylsilicone | 2 parts |
| 14) higher alcohol-modified silicone No. 7 | 5 parts |
| 15) 2-ethylhexyl para-methoxycinnamate | 1 part |
| 16) diisostearyl malate | 3 parts |
| 17) dimethylpolysiloxane (350 mm²/s) | 2 parts |
| 18) fragrance | suitable quantity |

(Note 1):
9701 Cosmetic Powder from Dow Corning Toray Co., Ltd., was used.

Production Method
1. Components 12 to 18 are mixed and dissolved.
2. Components 1 to 11 are mixed.
3. The mixture obtained in step 1 is added to the mixture obtained in step 2 with mixing and grinding is carried out.
4. The ground powder obtained in step 3 is pressed into a metal tray using a die to yield the product.

The powder foundation of this example is a formulation that incorporates a higher alcohol-modified silicone and a powder treated by higher alcohol-modified silicone No. 1 and has a suede-like feel and a strong moisturizing feel, and notwithstanding this is resistant to unwanted removal or disarrangement of the cosmetic; color dulling is also inhibited.

Example 27

Emulsion

| | | |
|---|---|---|
| 1) dimethylpolysiloxane (2 mm$^2$/s) | 2 parts |
| 2) decamethylcyclopentasiloxane | 15 parts |
| 3) polyether-modified silicone (Note 1) | 5 parts |
| 4) cetyl isooctanoate | 5 parts |
| 5) trioctanoin | 9 parts |
| 6) higher alcohol-modified silicone No. 6 | 1 part |
| 7) para-hydroxybenzoate ester | 0.1 part |
| 8) sodium lactate | 0.5 part |
| 9) purified water | balance |

(Note 1):
DC5200 from the Dow Corning Corporation was used.

Production Method
1. Components 1) to 6) were mixed and dispersed.
2. A mixture of components 7) to 9) was added to 1; emulsification was performed at room temperature; and the product was obtained by filling into a container.

The emulsion of this example had a suede-like tactile feel, did not make the skin sticky, and had an excellent moist tactile feel. The storage stability, and particularly the storage stability at high temperatures of 50° C. and higher, was excellent.

Example 28

Base Cream

| | | |
|---|---|---|
| 1) dimethylpolysiloxane (2 mm$^2$/s) | 2 parts |
| 2) decamethylcyclopentasiloxane | 10 parts |
| 3) polyether-modified silicone (Note 1) | 3 parts |
| 4) cetyl isooctanoate | 5 parts |
| 5) higher alcohol-modified silicone No. 4 | 5 parts |
| 6) 2-ethylhexyl para-methoxycinnamate | 2 parts |
| 7) silicone elastomer (Note 2) | 4 parts |
| 8) organomodified bentonite | 0.5 part |
| 9) barium sulfate | 2 parts |
| 10) talc | 1 part |
| 11) nylon powder | 3 parts |
| 12) preservative | suitable quantity |
| 13) xanthan gum | 0.1 part |
| 14) magnesium L-ascorbate phosphate ester | 0.3 part |
| 15) purified water | balance |

(Note 1):
SS-2910 from Dow Corning Toray Co., Ltd., was used.
(Note 2):
9045 Silicone Elastomer Blend from the Dow Corning Corporation was used.

Production Method
1. Components 1) to 11) were mixed and dispersed.
2. A mixture of components 12) to 15) was added to 1; emulsification was performed at room temperature; and the product was obtained by filling into a container.

The obtained base cream gave a suede-like feel, exhibited an excellent spreadability, and exhibited an excellent uniformity by its cosmetic film and an excellent adherence to the skin. The appearance of skin texture, wrinkles, and pores was also minimized. In addition, a stable emulsified state was present.

Example 29

Water-in-Oil Foundation (Gel)

| | | |
|---|---|---|
| 1) titanium oxide | 5 parts |
| 2) iron oxide (yellow, red, black) | 0.5 part |
| 3) spherical polystyrene (particle size = 3 μm) | 3 parts |
| 4) sorbitan sesquioleate | 1 part |
| 5) cyclopentasiloxane/(acrylates/polytrimethylsiloxymethacrylate) copolymer (Note 1) | 20 parts |
| 6) trimethylsiloxysilicic acid solution | 4 parts |
| 7) polyether-modified silicone (Note 2) | 4 parts |
| 8) higher alcohol-modified silicone No. 6 | 1 part |
| 9) isodecyl neopentanoate | 5 parts |
| 10) isopropyl palmitate | 2 parts |
| 11) vitamin E acetate | 0.1 part |
| 12) fragrance | suitable quantity |
| 13) ethanol | 10 parts |
| 14) dipropylene glycol | 5 parts |
| 15) preservative | suitable quantity |
| 16) 1,3-propanediol | 3 parts |
| 17) purified water | balance |

(Note 1):
FA 4001 CM Silicone Acrylate from Dow Corning Toray Co., Ltd., was used.
(Note 2):
SS-2910 from Dow Corning Toray Co., Ltd., was used.

Production Method

1: Components 1 to 3 were thoroughly stirred and mixed with a mixer.

2: Components 4 to 11 were thoroughly mixed. To this was added the mixture of step 1 with stirring.

3: Components 12 to 17 were dissolved to uniformity; the mixture of step 2 was added with stirring; and the product was obtained by filling into a container.

The obtained foundation had a fresh tactile feel. The skin texture was covered over; the spreadability was excellent; and the stability of the formulation was also excellent.

Example 30

W/O Liquid Foundation

| | | |
|---|---|---|
| 1) decamethylcyclopentasiloxane | 15 parts |
| 2) dimethylpolysiloxane (6 mm$^2$/s) | 8 parts |
| 3) pentaerythritol rosinate | 2 parts |
| 4) di-2-ethylhexyl succinate | 8 parts |
| 5) polyether-modified silicone | 3 parts |
| 6) decamethylcyclopentasiloxane, dimethicone crosspolymer (Note 1) | 2 parts |
| 7) higher alcohol-modified silicone No. 1 | 2 parts |
| 8) higher alcohol-modified silicone No. 2 | 2 parts |
| 9) silicone-treated finely divided titanium oxide | 5 parts |
| 10) silicone-treated titanium oxide | 7 parts |
| 11) silicone-treated spherical silica | 2 parts |
| 12) silicone-treated iron oxide red | 0.5 part |
| 13) silicone-treated iron oxide yellow | 1.4 parts |
| 14) silicone-treated titanium oxide black | 0.1 part |
| 15) 1,3-butylene glycol | 3 parts |

-continued

| | | |
|---|---|---|
| 16) ethanol | 7 parts | |
| 17) preservative | suitable quantity | |
| 18) purified water | balance | |
| 19) fragrance | suitable quantity | |

(Note 1):
DC 9040 from the Dow Corning Corporation was used.

Production Method

Components 1 to 8 were mixed to uniformity. To this was added a mixture of components 9 to 14 prepared by thorough mixing using a mixer. An aqueous phase prepared by mixing components 15 to 19 was added; emulsification was performed; and the product was obtained by filling into a container.

The W/O liquid foundation of this example is a formulation that uses both higher alcohol-modified silicone No. 2, which is modified at both terminals and has a disiloxane unit degree of polymerization of 14, and higher alcohol-modified silicone No. 1, which has a trisiloxane for the main chain. The W/O liquid foundation obtained in this example had a suede-like feel when used; had an excellent water resistance and cosmetic persistence; masked creases and wrinkles; and had an excellent spreadability and attachment. In addition, the W/O liquid foundation formed a uniform emulsified system as a whole and demonstrated a very good storage stability with elapsed time.

Example 31

Mascara

| | | |
|---|---|---|
| 1) paraffin wax | 5 parts | |
| 2) light liquid isoparaffin | balance | |
| 3) caprylmethicone | 0.5 part | |
| 4) higher alcohol-modified silicone No. 10 | 0.5 part | |
| 5) trioctanoin | 13 parts | |
| 6) decamethylcyclopentasiloxane | 20 parts | |
| 7) inulin stearate | 5 parts | |
| 8) cyclopentasiloxane, dimethicone crosspolymer (Note 1) | 10 parts | |
| 9) iron oxide black, surface treated with a fluorine compound | 6 parts | |
| 10) sucrose fatty acid ester | 4 parts | |
| 11) beeswax | 5 parts | |
| 12) pentaerythritol rosinate | 5 parts | |
| 13) preservative | suitable quantity | |
| 14) purified water | 5 parts | |

(Note 1):
DC 9040 from the Dow Corning Corporation was used.

Production Method

Components 1) to 12) were heated and dissolved followed by thorough mixing and dispersion; a mixture of components 13) and 14) was added; emulsification was performed; and the product was obtained by filling into a container.

The mascara according to this example is a formulation that incorporates higher alcohol-modified silicone No. 10, which contains a $C_{22}$ alkylene group. The mascara obtained in this example had a deep black appearance when used as well as an excellent gloss. In addition, the adherence to the eyelashes was excellent; the curling and volumizing effect for the eyelashes was excellent; and the persistence was also excellent.

Example 32

Shampoo

| | | |
|---|---|---|
| 1) water | balance | |
| 2) polyquaternium-10 | 10.0 parts | |
| 3) citric acid | suitable quantity | |
| 4) EDTA-2Na | 0.10 part | |
| 5) glycerol | 1.50 parts | |
| 6) cocamide MEA | 2.0 parts | |
| 7) glycol distearate | 2.0 parts | |
| 8) Na laureth sulfate | 30.0 parts | |
| 9) Na laureth-6 carboxylate | 10.0 parts | |
| 10) cocamide propylbetaine, NaCl | 10.0 parts | |
| 11) polyquaternium-7 | 3.0 parts | |
| 12) methyl isothiazolinone | suitable quantity | |
| 13) dimethicone | 0.1 part | |
| 14) higher alcohol-modified silicone No. 1 | 1.0 part | |
| 15) cocamide MEA | 1.0 part | |
| 16) (bisisobutyl PEG-14/amodimethicone) copolymer (Note 1) | 0.5 part | |

(Note 1):
SILSTYLE104 from Dow Corning Toray Co., Ltd., was used.

Production Method
1. Components 1) to 7) were heated and dissolved to uniformity (80° C.).
2. A mixture of components 8) to 10) was added to 1 and emulsification was performed (80° C., 5 minutes).
3. After cooling 2, a mixture of components 11) to 16) was added; mixing was carried out with thorough stirring; and the product was obtained by filling into a container.

The shampoo of this example is an oil-in-water emulsion-type hair cleanser that contains higher alcohol-modified silicone No. 1. The shampoo obtained in this example had an excellent foam generation performance, foam quality, and foam persistence and had a high cleansing effect. In addition, when applied it had a very thick body feel; there was no slimy feel (slimy tactile feel) when washing was finished; the hair was not stiff after use; and an excellent flexibility was obtained after drying.

Example 33

Hair Conditioner

| | | |
|---|---|---|
| 1) cetyltrimethylammonium chloride | 0.6 part | |
| 2) cetostearyl alcohol | 2.0 parts | |
| 3) (bisisobutyl PEG-14/amodimethicone) copolymer | 3.0 parts | |
| 4) decamethylcyclopentasiloxane | 14.0 parts | |
| 5) higher alcohol-modified silicone No. 1 | 1.0 part | |
| 6) glyceryl stearate | 1.0 part | |
| 7) stearic acid | 0.5 part | |
| 8) glycerol | 5.0 parts | |
| 9) propylene glycol | 5.0 parts | |
| 10) Yellow No. 4 (dye) | suitable quantity | |
| 11) fragrance | suitable quantity | |
| 12) preservative | suitable quantity | |
| 13) EDTA-3Na | suitable quantity | |
| 14) ion-exchanged water | balance | |

Production Method

Components 10) to 14) were mixed and dissolved to uniformity. Components 1) to 9) were mixed and heated (70° C.)

to uniformity and were added; emulsification was performed; and the product was then obtained by filling into a container.

The hair conditioner of this example is an oil-in-water emulsion-type hair conditioner that contains higher alcohol-modified silicone No. 1. The hair conditioner obtained according to this example, when applied to the air, had a thick-body, suede-like feel. When it was washed out, the smoothness, luster, and springy.resilient feel were excellent. After drying, the hair was provided with flexibility and an excellent combability. Furthermore, because the cetostearyl alcohol+cationic surfactant+water system formed a stable gel structure, the use sensation was good, the storage stability was excellent, and crystallization of the higher alcohol was inhibited. After washing, the hair had a fresh feel and a light, well-behaved tactile feel. Another advantage was that there was no cuticle damage even after repeated rinsing. Moreover, the pleasant scent of the fragrance that had been incorporated in the hair conditioner was subtly persistent even after washing was finished, which thus demonstrated that the retention of the fragrance had been improved.

When this hair conditioner was used in combination with the shampoo of Example 32, which contained the same higher alcohol-modified silicone, the finish and luster of the hair post-drying was particularly good.

Example 34

Hair Oil

| | | |
|---|---|---|
| 1) light liquid isoparaffin | balance | |
| 2) dimethylpolysiloxane (6 mm$^2$/s) | 20.0 parts | |
| 3) higher alcohol-modified silicone No. 4 | 1.0 part | |
| 4) hydrogenated polyisobutene, polysilicone 13 * | 9.0 parts | |
| 5) fragrance | suitable quantity | |

* FZ-2250 from Dow Corning Toray Co., Ltd.

Production Method

Components 1) to 5) were dissolved and mixed by stirring at 70 to 80° C. and the product was obtained by filling into a container.

The obtained hair oil had the appearance of a viscous and highly transparent oil. When applied, a suede-like feel was present and the spreadability on the hair as a whole was excellent. After finishing, excellent effects were obtained with regard to hair flexibility, emollient feel, gloss, and luster. Another characteristic feature was well-behaved hair after drying.

Production examples for cosmetics and topical skin preparations are provided below.

Example 35

Sheet Mask

A sheet mask cosmetic was produced by impregnating a nonwoven fabric that was approximately face shaped and that had holes cut in it for the eyes, nose, and mouth, with about 10-fold, based on the mass of the nonwoven fabric, of a water-based composition, i.e., a lotion, produced by the method described below.

Water-based composition, i.e., lotion, used in the sheet mask of Example 35:

| | |
|---|---|
| 1) dipropylene glycol | 8.0 parts |
| 2) 1,3-butylene glycol | 10.0 parts |
| 3) lactic acid | 0.05 part |
| 4) sodium lactate | 0.1 part |
| 5) polyethylene glycol 20000 | 0.5 part |
| 6) ethanol | 5.0 part |
| 7) methyl para-hydroxybenzoate | 0.1 part |
| 8) fragrance | 0.05 part |
| 9) higher alcohol-modified silicone No. 1 | 0.5 part |
| 10) polyoxyethylene sorbitan (20 EO) monooleate | 1.0 part |
| 11) carboxyvinyl polymer | 1.4 parts |
| 12) pH adjuster | suitable quantity |
| 13) purified water | balance |

Production
1. Components 6) to 10) were mixed and dissolved.
2. Components 1) to 5) and components 11) to 13) were mixed and dissolved.
3. The mixture of step 1. was added and mixed into the mixture of step 2. to obtain the water-based composition, i.e., lotion.

Example 36

Sheet Pack

A sheet pack cosmetic was produced by impregnating a nonwoven fabric that was approximately face shaped and that had holes cut in it for the eyes, nose, and mouth, with about 10-fold, based on the mass of the nonwoven fabric, of a water-based composition, i.e., a cosmetic lotion, produced by the method described below.

Water-based composition, i.e., cosmetic lotion, used in the sheet pack of Example 36:

| | |
|---|---|
| 1) polyoxyethylene hydrogenated castor oil | 0.5 part |
| 2) glycerol monostearate | 0.1 part |
| 3) cetostearyl alcohol | 0.1 part |
| 4) dimethicone | 0.1 part |
| 5) higher alcohol-modified silicone No. 1 | 0.1 part |
| 6) fragrance | suitable quantity |
| 7) methyl para-hydroxybenzoate | suitable quantity |
| 8) ethanol | 5.0 parts |
| 9) 1,3-butylene glycol | 10.0 parts |
| 10) polyethylene glycol 6000 | 5.0 parts |
| 11) carboxyvinyl polymer | 1.0 part |
| 12) pH adjuster | suitable quantity |
| 13) purified water | balance |

Production Method
1. Components 7) to 13), already heated and dissolved at 70° C., were added to components 1) to 6), already heated and dissolved at 70° C., and emulsification was carried out by stirring by the application of mechanical force.
2. The emulsion of 1. was cooled to room temperature to obtain the water-based composition, i.e., a cosmetic lotion.

Example 37

Massage Cosmetic

| | |
|---|---|
| 1) POE (20) cetyl ether | 2.0 part |
| 2) lipophilic glycerol monostearate | 4.0 part |
| 3) cetostearyl alcohol | 2.0 part |
| 4) white petrolatum | 4.0 part |
| 5) higher alcohol-modified silicone No. 1 | 0.5 part |

| | |
|---|---|
| 6) squalane | 3.5 part |
| 7) dimethicone | 0.5 part |
| 8) methyl para-hydroxybenzoate | suitable quantity |
| 9) 1,3-butylene glycol | 10.0 part |
| 10) xanthan gum | 0.05 part |
| 11) carboxyvinyl polymer | 0.4 part |
| 12) pH adjuster | suitable quantity |
| 13) purified water | balance |

Production Method

Components 1) to 7) and components 8) to 13) were both heated to 80° C. and were emulsified while stirring. Cooling to room temperature while mixing then gave a massage cosmetic.

Example 38

Body Soap

| | |
|---|---|
| 1) triethanolamine laurate | 20.0 parts |
| 2) sodium PEO (3) lauryl sulfate | 2.0 parts |
| 3) lauryldimethylaminoacetic acid betaine | 2.0 parts |
| 4) diethanolamide of cocofatty acids | 3.0 parts |
| 5) higher alcohol-modified silicone No. 1 | 0.1 part |
| 6) hydroxypropylmethyl cellulose | 0.1 part |
| 7) purified water | balance |
| 8) preservative | suitable quantity |
| 9) fragrance | suitable quantity |

Production Method

Component 6) was swollen with component 7) and components 1) to 9) were thereafter mixed to provide the body soap.

Example 39

Hand Soap

| | |
|---|---|
| 1) potassium laurate | 5.0 parts |
| 2) potassium myristate | 10.0 parts |
| 3) potassium palmitate | 3.0 parts |
| 4) lauryldimethylaminoacetic acid betaine | 0.5 part |
| 5) diethanolamide of cocofatty acids | 3.0 parts |
| 6) higher alcohol-modified silicone No. 1 | 0.1 part |
| 7) purified water | balance |
| 8) preservative | suitable quantity |

Production Method

Components 1) to 8) were heated and dissolved; cooling to room temperature then yielded the hand soap.

Example 40

Hair Spray

A hair spray precursor solution prepared by the method described below and a propellant (liquefied petroleum gas) were filled into an aerosol can at a mixing ratio of precursor solution/propellant=70/30 to give the hair spray product.
precursor solution used in the hair spray of Example 40:

| | |
|---|---|
| 1) 1,3-butylene glycol | 0.2 part |
| 2) 2-ethylhexyl palmitate | 1.0 part |
| 3) polyoxyethylene (20) sorbitan monooleate | 0.5 part |
| 4) stearyltrimethylammonium chloride | 0.5 part |
| 5) higher alcohol-modified silicone No. 1 | 1.0 part |
| 6) dimethylpolysiloxane | 1.0 part |
| 7) amphoteric polymer (*1) | 4.0 parts (*2) |
| 8) ethanol | 90.0 parts |
| 9) fragrance | suitable quantity |
| 10) preservative | suitable quantity |
| 11) purified water | balance |

(*1): Product name: Yukafoamer R205 from Mitsubishi Chemical Corporation, a 30% ethanol solution of N-methacryloylethyl-N,N-dimethylammonium-α-N-methylcarboxybetaine · butyl methacrylate copolymer
(*2): The number of parts in the composition is the value for the pure resin in component 7).

Production Method

Components 1) to 11) are mixed to uniformity to provide the hair spray precursor solution.

Example 41

Nail Enamel (Components)

| | |
|---|---|
| 1) nitrocellulose | 10.0 parts |
| 2) silicic anhydride | 3.0 parts |
| 3) acetyltributyl citrate | 3.0 parts |
| 4) alkyl acrylate copolymer | 2.0 parts |
| 5) sucrose acetate isobutyrate | 2.0 parts |
| 6) isopropyl alcohol | 5.0 parts |
| 7) higher alcohol-modified silicone No. 1 | 0.5 part |
| 8) ethyl acetate | balance |
| 9) butyl acetate | 31.5 parts |
| 10) butanol | 5.0 parts |
| 11) 5% Silicone-treated iron oxide red | 0.5 part |
| 12) 5% Silicone-treated titanium oxide | 0.5 part |
| 13) 5% Silicone-treated ultramarine pink | 2.0 parts |
| 14) 5% Silicone-treated iron oxide red-coated titanium mica | 5.0 parts |

Production Method

1. Components 1) to 4) were pre-dispersed using a two-roll mill and processed into chips.
2. The chips of step 1. and components 5) to 10) were mixed to uniformity and components 11) to 14) were then added and dispersion to uniformity was carried out. The obtained dispersion was filled into a container to provide the nail enamel.

Example 42

Ointment

| | |
|---|---|
| 1) "White Petrolatum" per the Japanese Pharmacopoeia | 25.0 parts |
| 2) "Stearyl Alcohol" per the Japanese Pharmacopoeia | 20.0 parts |
| 3) higher alcohol-modified silicone No. 1 | 4.0 parts |
| 4) "Propylene Glycol" per the Japanese Pharmacopoeia | 12.0 parts |
| 5) "Polyoxyethylene Hydrogenated Castor Oil 60" per the Japanese Pharmacopoeia | 4.0 parts |
| 6) "Glyceryl Monostearate" per the Japanese Pharmacopoeia | 1.0 part |
| 7) "Methyl para-Hydroxybenzoate" per the Japanese Pharmacopoeia | 0.1 part |
| 8) "Propyl para-Hydroxybenzoate" per the Japanese Pharmacopoeia | 0.1 part |
| 9) "Purified Water" per the Japanese Pharmacopoeia | balance |

Production Method

An ointment was prepared according to the "Hydrophilic Ointment" production method of the Japanese Pharmacopoeia. The higher alcohol-modified silicone No. 1 was processed with the "White Petrolatum", "Stearyl Alcohol", "Polyoxyethylene Hydrogenated Castor Oil 60", and "Glyceryl Monostearate".

Example 43

Ointment

| | |
|---|---|
| 1) "*Scopolia* Extract" per the Japanese Pharmacopoeia | 10.0 parts |
| 2) "Tannic Acid" per the Japanese Pharmacopoeia | 3.0 parts |
| 3) "dl-Camphor" per the Japanese Pharmacopoeia | 1.0 part |
| 4) "Ichthammol" per the Japanese Pharmacopoeia | 10.0 parts |
| 5) ointment prepared in Example 42 | balance |

Production Method

An ointment was prepared based on the "Compound *Scopolia* Extract and Tannic Acid Ointment" per the Japanese Pharmacopoeia.

The ointment of Example 43 was soft and had a moist tactile feel and when applied it had a moderate suede-like tactile feel; it was well suited in particular for the treatment of hemorrhoids. There was also little itching after application to an affected part.

The invention claimed is:

1. A cosmetic and topical skin preparation comprising a higher alcohol-modified silicone (A) with general formula (1-1-1), general formula (1-1-1):

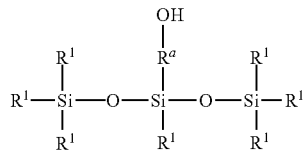

(1-1-1)

wherein each $R^1$ is independently a $C_{1-10}$ alkyl group, $C_{6-10}$ aryl group, or a —OH group; $R^a$ is a branched or straight-chain $C_{10-30}$ alkylene group or an arylene group; and at least one $C_{10-30}$ higher alcohol (B) at from 5 to 1000 mass parts per 100 mass parts of the higher alcohol-modified silicone (A).

2. The cosmetic and topical skin preparation according to claim 1 further containing water (C) and a surfactant (D), wherein the preparation forms a gel structure.

3. The cosmetic and topical skin preparation according to claim 1, wherein the preparation is an oil-in-water emulsion cosmetic.

4. The cosmetic and topical skin preparation according to claim 1 further containing a silicone resin (E).

5. The cosmetic and topical skin preparation according to claim 1 further containing a silicone elastomer (F).

6. A method of producing a cosmetic and topical skin preparation comprising:

a step of heating 100 mass parts of at least one higher alcohol-modified silicone (A) with general formula (1-1-1), general formula (1-1-1):

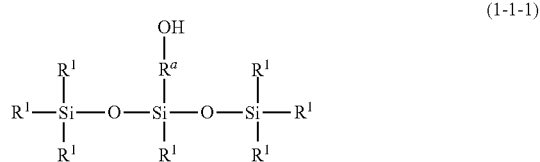

(1-1-1)

wherein each $R^1$ is independently a $C_{1-10}$ alkyl group, $C_{6-10}$ aryl group, or a —OH group; $R^a$ is a branched or straight-chain $C_{10-30}$ alkylene group or an arylene group, and 10 to 1000 mass parts of at least one $C_{10-30}$ higher alcohol (B), at from 50° C. to 150° C.

7. The method according to claim 6, further comprising:

a step of mixing the at least one higher alcohol-modified silicone (A) and the at least one $C_{10-30}$ higher alcohol (B) before the step of heating.

8. The cosmetic and topical skin preparation according to claim 4 wherein the silicone resin (E) is an organopolysiloxane having a network structure.

9. The cosmetic and topical skin preparation according to claim 5 wherein the silicone elastomer (F) is a liquid silicone elastomer.

\* \* \* \* \*